(12) United States Patent
Guzman et al.

(10) Patent No.: US 7,642,287 B2
(45) Date of Patent: Jan. 5, 2010

(54) STATIN PHARMACEUTICAL COMPOSITIONS AND RELATED METHODS OF TREATMENT

(75) Inventors: Hector Guzman, Jamaica Plain, MA (US); Julius Remenar, Framingham, MA (US); Orn Almarsson, Shrewsbury, MA (US)

(73) Assignee: Transform Pharmaceuticals, Inc., Lexington, MA (US)

( * ) Notice: Subject to any disclaimer, the term of this patent is extended or adjusted under 35 U.S.C. 154(b) by 325 days.

(21) Appl. No.: 11/197,880

(22) Filed: Aug. 5, 2005

(65) Prior Publication Data

US 2006/0034815 A1 Feb. 16, 2006

Related U.S. Application Data

(60) Provisional application No. 60/599,543, filed on Aug. 6, 2004, provisional application No. 60/623,518, filed on Oct. 29, 2004, provisional application No. 60/655,982, filed on Feb. 24, 2005.

(51) Int. Cl.
*A01N 37/06* (2006.01)
(52) U.S. Cl. ........................... 514/547; 514/571
(58) Field of Classification Search ................. 549/292; 514/547, 571
See application file for complete search history.

(56) References Cited

U.S. PATENT DOCUMENTS

| 3,536,809 A | 10/1970 | Allpezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,231,938 A | 11/1980 | Monaghan et al. |
| 4,346,227 A | 8/1982 | Terahara et al. |
| 4,444,784 A | 4/1984 | Hoffman et al. |
| 5,030,447 A | 7/1991 | Joshi et al. |
| 5,059,595 A | 10/1991 | Le Grazie |
| 5,073,543 A | 12/1991 | Marshall et al. |
| 5,120,548 A | 6/1992 | McClelland et al. |
| 5,177,080 A | 1/1993 | Angerbauer et al. |
| 5,223,415 A | 6/1993 | Conder et al. |
| 5,273,995 A | 12/1993 | Roth |
| 5,354,556 A | 10/1994 | Sparks et al. |
| 5,354,772 A | 10/1994 | Kathawala |
| 5,356,896 A | 10/1994 | Kabadi et al. |
| 5,366,738 A | 11/1994 | Rork et al. |
| 5,506,248 A | 4/1996 | Nikfar et al. |
| 5,591,767 A | 1/1997 | Mohr et al. |
| 5,639,476 A | 6/1997 | Oshlack et al. |
| 5,674,533 A | 10/1997 | Santus et al. |
| 5,686,104 A | 11/1997 | Mills et al. |
| 5,733,566 A | 3/1998 | Lewis |
| 5,861,399 A | 1/1999 | Seed et al. |
| 6,126,971 A | 10/2000 | Mills et al. |
| 6,284,268 B1 | 9/2001 | Mishra et al. |
| 6,365,185 B1 | 4/2002 | Ritschel et al. |
| 6,531,507 B1 | 3/2003 | Pflaum et al. |
| 6,534,088 B2 | 3/2003 | Guivarc'h et al. |
| 6,558,659 B2 | 5/2003 | Fox et al. |
| 6,569,461 B1 | 5/2003 | Tillyer et al. |
| 6,583,295 B1 | 6/2003 | Pflaum |
| 6,649,775 B2 | 11/2003 | Lee et al. |
| 6,740,775 B1 | 5/2004 | Pflaum |
| 6,777,552 B2 | 8/2004 | Niddam-Hildesheim et al. |
| 2002/0044981 A1 | 4/2002 | Surette |
| 2002/0068095 A1 | 6/2002 | Qi et al. |
| 2003/0086571 A1 | 5/2003 | Audebert et al. |
| 2003/0114685 A1 | 6/2003 | Niddam-Hildesheim et al. |
| 2003/0120086 A1 | 6/2003 | Pflaum |
| 2003/0175338 A1 | 9/2003 | Singh et al. |
| 2003/0216596 A1 | 11/2003 | Sugio et al. |
| 2004/0009986 A1 | 1/2004 | Ohsawa et al. |
| 2004/0018248 A1 | 1/2004 | Bendich |
| 2004/0058024 A1 | 3/2004 | Surette |
| 2004/0072894 A1 | 4/2004 | Kerc |
| 2004/0235935 A1 | 11/2004 | Vanderbist et al. |
| 2004/0259216 A1 | 12/2004 | Choi et al. |
| 2005/0032757 A1 | 2/2005 | Cho |

(Continued)

FOREIGN PATENT DOCUMENTS

EP 1157692 A1 11/2001

(Continued)

OTHER PUBLICATIONS

Chin-Dusting et al., Lipids and atherosclerosis: clinical management of hypercholesterolaemia, Expert Opinion on Pharmacotherapy, 2001, 2(3), p. 419-430.*

(Continued)

*Primary Examiner*—Frederick Krass
*Assistant Examiner*—Darryl C Sutton
(74) *Attorney, Agent, or Firm*—RatnerPrestia

(57) ABSTRACT

The invention provides novel omega-3 oil solutions of one or more statins. These solutions are readily bioavailable. Notably, because the solutions of the invention contain an omega-3 oil as the major ingredient, they not only provide an antihypercholesterolemic effect due to the statin active ingredient, they also provide recommended daily dosages of omega-3 oils (i.e., approximately 1 gram of omega-3 oil per day), or a portion thereof. The invention also provides novel salts of one or more statins.

5 Claims, 33 Drawing Sheets

U.S. PATENT DOCUMENTS

| | | | |
|---|---|---|---|
| 2005/0096390 A1 | 5/2005 | Holm et al. | |
| 2005/0096391 A1 | 5/2005 | Holm et al. | |
| 2005/0101561 A1 | 5/2005 | Tunac | |
| 2005/0197501 A1 | 9/2005 | Niddam-Hildesheim et al. | |
| 2005/0267197 A1 | 12/2005 | Berlin | |
| 2006/0035941 A1 | 2/2006 | Chen et al. | |

FOREIGN PATENT DOCUMENTS

| | | | |
|---|---|---|---|
| WO | WO00/37057 | | 6/2000 |
| WO | WO00/45817 | | 8/2000 |
| WO | WO 01/10813 A1 | | 2/2001 |
| WO | WO01/37831 | | 5/2001 |
| WO | WO 01/43723 A1 | | 6/2001 |
| WO | WO 02/30415 A1 | | 4/2002 |
| WO | WO02/43659 | * | 6/2002 |
| WO | WO02/100394 | | 12/2002 |
| WO | WO 03/000177 A2 | | 1/2003 |
| WO | WO 03/000239 A1 | | 1/2003 |
| WO | WO 03/016317 | | 2/2003 |
| WO | WO03/105837 | | 12/2003 |
| WO | WO2004/004774 | | 1/2004 |
| WO | WO2005/013940 | | 2/2005 |
| WO | WO2005/023778 | | 3/2005 |
| WO | WO2005/034908 | | 4/2005 |
| WO | WO2005/067921 | | 7/2005 |
| WO | WO2005/104864 | | 11/2005 |
| WO | WO2006/002127 | | 1/2006 |
| WO | WO2006/013602 | | 2/2006 |
| WO | WO2006/021293 | | 3/2006 |

OTHER PUBLICATIONS

Harris, W., Fish oils and plasma lipid and liproprotein meabolism in humans: a critical review, Journal of Lipid Research, 1989, 30, p. 785-807.*

Layne, K., et al., Normal Subjects Consuming Physiological Levels of 18;3(n-3) and 20:5(n-3) from Flaxseed Oils Have Characteristic Differences in Plasma Lipid and Lipoprotein Fatty Acid Levels, THe Journal of Nutrition, 1996, 126(9), p. 2130-2140.*

Contacos et al., "Effect of Pravastatin and ω-3 Fatty Acids on Plasma Lipids and Lipoproteins in Patients With Combined Hyperlipidemia", Arteriosclerosis and Thrombosis, vol. 13, No. 12, pp. 1755-1762 (Dec. 1993).

Bønaa et al., "Habitual fish consumption, plasma phospholipid fatty acids, and serum lipids: The Tromsø Study", Am J Clin Nutr, 55, pp. 1126-1134 (1992).

Tobert, J., "Lovastatin and Beyond: The History of the HMG-CoA Reductase Inhibitors", Nature Reviews, vol. 2, pp. 517-526 (2003).

Harris, William S, Clin. Cardiol. 22, (Suppl. II), II-40-II-43 (1999).

Kris-Etherton, et al., Circulation, 106: 2747-2757 (2002).

Qi et al., Nat. Biotechnol., pp. 739-745 (2004).

Kim, Chemg-ju, Controlled Release Dosage Form Design, 2 Technomic Publishing, Lancaster, Pa.: 2000.

Grekas et al., "Combined Treatment with Low-Dose Pravastatin and Fish Oil in Post-Renal Transplantation Dislipidemia," *Nephron*, Aug. 2001, vol. 88, No. 4, pp. 329-333.

P. Singer, "Fluvastatin und Fischoel wirken staerker auf kardiovakulaere Risikofaktoren als Fluvastatin allein," *Medizinische Welt*, 2002, Germany, vol. 3, No. 9, pp. 298-302.

Yano et al., "Effects of ethyl-all-cis-5,8,11,14,17-icosapentaenoate (epa-e), Paravastatin and their Combination on Serum Lipids and Intimal Thickening of Cuss-Sheathed Carotid Artery in Rabbits," *Life Sciences*, 1997, vol. 61, No. 20, pp. 2007-2015.

Nakamura et al., "Joint effects of HMG-CoA reductase inhibitors and eicosapentaenoic acids on serum lipid profile and plasma fatty acid concentrations in patients with hyperlipidemia," *Int J Clin Lab Res*, 1999, vol. 29, pp. 22-25.

Nakamura et al., "Effect of HMG-CoA reductase inhibitors on plasma polyunsaturated fatty acid concentrations in patients with hyperlipidemia," *Int J clin Lab Res*, (1998) vol. 28, pp. 192-195.

Durrington et al., "An omega-3 polyunsaturated fatty acid concentrate administered for one year decreased triglycerides in simvastatin treated patients with coronory hear disease and persisting hypertriglyceridaemia," *Heart*, May 2001, vol. 85, No. 5, pp. 544-548.

A. Norday, "Statins and omega-3 fatty acids in the treatment of dyslipidemia and coronary heart disease," *Minerva Med.*, Oct. 2002, vol. 93, No. 5. pp. 357-363. (Abstract).

International Search Report of PCT/US20/05027815, dated May 11, 2006.

European Search Report of 05778295.5, dated Mar. 12, 2008.

* cited by examiner

STATIN PHARMACEUTICAL COMPOSITIONS AND RELATED METHODS OF TREATMENT

The present application claims the benefit of priority of U.S. Provisional Application Ser. No. 60/599,543, filed Aug. 6, 2004, U.S. Provisional Application Ser. No. 60/623,518, filed Oct. 29, 2004, and U.S. Provisional Application Ser. No. 60/655,982, filed Feb. 24, 2005, the contents of which are incorporated herein by reference in their entireties.

FIELD OF THE INVENTION

The invention provides novel omega-3 ester-based oil suspensions of statins. These suspensions are substantially free of any food effect, effective in small volumes, and readily bioavailable.

BACKGROUND OF THE INVENTION

It has been clear for several decades that elevated blood cholesterol is a major risk factor for coronary heart disease (CHD), and many studies have shown that the risk of CHD events can be reduced by lipid-lowering therapy. Prior to 1987, the lipid-lowering armamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. With the introduction of lovastatin (MEVACOR®; see U.S. Pat. No. 4,231,938), the first inhibitor of HMG-CoA reductase to become available for prescription in 1987, for the first time physicians were able to obtain comparatively large reductions in plasma cholesterol with very few adverse effects.

In addition to the natural fermentation products, mevastatin and lovastatin, there are now a variety of semi-synthetic and totally synthetic HMG-CoA reductase inhibitors, including simvastatin (ZOCOR®; see U.S. Pat. No. 4,444,784), pravastatin sodium salt (PRAVACHOL®; see U.S. Pat. No. 4,346,227), fluvastatin sodium salt (LESCOL®; see U.S. Pat. No. 5,354,772), atorvastatin calcium salt (LIPITOR®; see U.S. Pat. No. 5,273,995) and cerivastatin sodium salt (also known as rivastatin; see U.S. Pat. No. 5,177,080). The HMG-CoA reductase inhibitors described above belong to a structural class of compounds which contain a moiety which can exist as either a 3-hydroxy lactone ring or as the corresponding ring opened dihydroxy open-acid, and are often referred to as "statins."

Salts of the dihydroxy open-acid can be prepared, and in fact, as noted above, several of the marketed statins are administered as the dihydroxy open acid salt forms. Lovastatin and simvastatin are marketed worldwide in their lactonized form.

The hypotriglyceridemic effects of omega-3 oils from fish oils are well established. Amounts both above and below about 1 gram per day of omega-3 oils from fish oil have been shown to decrease serum triglyceride concentrations by about 25% to about 40%, decrease VLDL blood plasma levels, and to increase both LDL and HDL plasma levels (See e.g., Harris, William S, *Clin. Cardiol.* 22, (Suppl. II), II-40-II-43 (1999)). A dose-response relationship exists between omega-3 oil intake and triglyceride lowering. Postprandial triglyceridemia is especially sensitive to chronic omega-3 oil consumption. *Kris-Etherton, et al., Circulation.* 2002; 106: 2747.

While there are numerous known statin dosage forms, the need continues to exist for commercially practicable statin pharmaceutical compositions that exhibit enhanced bioavailability, are readily formulated and administered, and comprise ingredients that enhance the antihypercholesterolemic effect of the statin.

SUMMARY OF THE INVENTION

The invention provides novel omega-3 oil-based pharmaceutical compositions of one or more statins having unexpected properties. These pharmaceutical compositions are readily bioavailable. Notably, because the pharmaceutical compositions of the invention contain an omega-3 oil as the major ingredient, they not only provide an antihypercholesterolemic effect due to the statin active ingredient, they also provide recommended daily dosages of omega-3 oils (i.e., one gram of omega-3 oil per day, as per AHA guidelines), or a portion thereof.

The invention comprises a suspension, or a heterogeneous formulation, of one or more statins in omega-3 oil. In specific embodiments, the invention provides suspensions of amorphous and/or crystalline particles of one or more statins in an omega-3 oil.

In one embodiment, pharmaceutical compositions of the invention comprise an omega-3 alkyl ester, preferably an omega-3 ethyl ester. In another embodiment, pharmaceutical compositions of the invention comprise an omega-3 mono-, di-, or triglyceride oil.

In another embodiment, the invention provides a pharmaceutical composition comprising about 500, 600, 700, 800, 900, 1000, 1100, 1200, 1300, 1400, or 1500 mg of an omega-3 oil with greater than or equal to about 90 percent purity and about 1, 2, 3, 4, 5, 10, 15, 20, 25, 30, 35, 40, 45, 50, 55, 60, 65, 70, 75, 80, 90, 100, 110, 120, 130, 140, 150, or 160 mg of one or more salts of a statin(s). In another embodiment, the invention provides a pharmaceutical composition comprising about 500, 600, 700, 800, 900, 1000, 1100, 1200, 1300, 1400, or 1500 mg of an omega-3 oil with a composition greater than or equal to about 90 percent EPA and DHA and about 1, 2, 3, 4, 5, 10, 15, 20, 25, 30, 35, 40, 45, 50, 55, 60, 65, 70, 75, 80, 90, 100, 110, 120, 130, 140, 150, or 160 mg of one or more salts of a statin(s).

In another embodiment, the salt is a calcium salt of pravastatin. In another embodiment, the salt is a calcium salt of fluvastatin. In another embodiment, the salt is a magnesium salt of pravastatin. In another embodiment, the salt is a zinc salt of pravastatin. In another embodiment, the salt is crystalline.

In another embodiment, the invention provides a pharmaceutical composition comprising about 500, 600, 700, 800, 900, 1000, 1100, 1200, 1300, 1400, or 1500 mg of an omega-3 oil with greater than or equal to about 90 percent purity and about 1, 2, 3, 4, 5, 10, 15, 20, 25, 30, 35, 40, 45, 50, 55, 60, 65, 70, 75, 80, 90, 100, 110, 120, 130, 140, 150, or 160 mg of one or more statins. In another embodiment, the invention provides a pharmaceutical composition comprising about 500, 600, 700, 800, 900, 1000, 1100, 1200, 1300, 1400, or 1500 mg of an omega-3 oil with a composition greater than or equal to about 90 percent EPA and DHA and about 1, 2, 3, 4, 5, 10, 15, 20, 25, 30, 35, 40, 45, 50, 55, 60, 65, 70, 75, 80, 90, 100, 110, 120, 130, 140, 150, or 160 mg of one or more statins.

In another embodiment, the omega-3 oil is an omega-3 ester. In another embodiment, the omega-3 oil is an omega-3 ethyl ester. In another embodiment, the statin is in the form of a lactone. In another embodiment, the statin is a free acid.

In another embodiment, the purity of omega-3 esters or omega-3 alkyl esters is at least about 50 percent by weight, at least about 60 percent by weight, at least about 70 percent by weight, at least about 75 percent by weight, at least about 80 percent by weight, or at least about 85 percent by weight. In another embodiment, the purity of omega-3 esters or omega-3 alkyl esters is about 25, 30, 35, 40, 45, 50, 55, 60, 65, 70, 75, 80, 85, 90, 95, 99 percent or more by weight. In another embodiment, the purity of omega-3 esters or omega-3 alkyl esters is between about 25 and about 100 percent by weight, between about 40 and about 100 percent by weight, between about 50 and about 100 percent by weight, between about 60 and about 100 percent by weight, between about 70 and about 100 percent by weight, between about 75 and about 100 percent by weight, between about 75 and about 95 percent by weight, between about 75 and about 90 percent by weight, or between about 80 and about 85 percent by weight. In another embodiment, the purity of omega-3 esters or omega-3 alkyl esters is about 100 percent by weight, about 99 percent by weight, at least about 96 percent by weight, at least about 92 percent by weight, at least about 90 percent by weight, at least about 85 percent by weight, at least about 80 percent by weight, at least about 75 percent by weight, at least about 70 percent by weight, at least about 65 percent by weight, at least about 60 percent by weight, at least about 55 percent by weight, or at least about 50 percent by weight.

In another embodiment, the oil composition comprising EPA and DHA is at least about 50 percent by weight, at least about 60 percent by weight, at least about 70 percent by weight, at least about 75 percent by weight, at least about 80 percent by weight, or at least about 84 percent by weight of EPA and DHA. In another embodiment, the oil composition comprising EPA and DHA is about 25, 30, 35, 40, 45, 50, 55, 60, 65, 70, 75, 80, 85, 90, or 95 percent by weight of EPA and DHA. In another embodiment, the oil composition comprising EPA and DHA is between about 25 and about 95 percent by weight, between about 40 and about 95 percent by weight, between about 50 and about 95 percent by weight, between about 60 and about 95 percent by weight, between about 70 and about 95 percent by weight, between about 75 and about 95 percent by weight, between about 75 and about 90 percent by weight, between about 75 and about 85 percent by weight, or between about 80 and about 85 percent by weight of EPA and DHA. In another embodiment, the oil composition comprising EPA and DHA is about 99 percent by weight, about 96 percent by weight, about 92 percent by weight, about 90 percent by weight, about 84 percent by weight, about 80 percent by weight, about 75 percent by weight, about 70 percent by weight, about 65 percent by weight, about 60 percent by weight, about 55 percent by weight, or about 50 percent by weight of EPA and DHA.

In another embodiment, the omega-3 ester or omega-3 alkyl ester has about a 23:19 ratio of EPA:DHA, about a 75:11 ratio of EPA:DHA, about a 95:1 ratio of EPA:DHA, about a 9:2 ratio of EPA:DHA, about a 10:1 ratio of EPA:DHA, about a 5:1 ratio of EPA:DHA, about a 3:1 ratio of EPA:DHA, about a 2:1 ratio of EPA:DHA, about a 1:1 ratio of EPA:DHA, about a 1:2 ratio of EPA:DHA, about a 1:3 ratio of EPA:DHA, or about a 1:5 ratio of EPA:DHA. In another embodiment, the omega-3 ester or omega-3 alkyl ester has about a 95:1 ratio of EPA:DHA, about a 75:1 ratio of EPA:DHA, about a 50:1 ratio of EPA:DHA, about a 25:1 ratio of EPA:DHA, about a 20:1 ratio of EPA:DHA, about a 15:1 ratio of EPA:DHA, about a 10:1 ratio of EPA:DHA, about a 7.5:1 ratio of EPA:DHA, about a 5:1 ratio of EPA:DHA, about a 4:1 ratio of EPA:DHA, about a 3:1 ratio of EPA:DHA, about a 2:1 ratio of EPA:DHA, about a 1.5:1 ratio of EPA:DHA, about a 1:1 ratio of EPA:DHA, about a 1:1.5 ratio of EPA:DHA, about a 1:2 ratio of EPA:DHA, about a 1:3 ratio of EPA:DHA, or about a 1:5 ratio of EPA:DHA. In another embodiment, the omega-3 ester or omega-3 alkyl ester has from about a 95:1 ratio to about a 1:5 ratio of EPA:DHA, from about a 50:1 ratio to about a 1:1 ratio of EPA:DHA, from about a 25:1 ratio to about a 1:1 ratio of EPA:DHA, from about a 10:1 ratio to about a 1:1 ratio of EPA:DHA, from about a 5:1 ratio to about a 1:1 ratio of EPA:DHA, from about a 3:1 ratio to about a 1:1 ratio of EPA:DHA, from about a 2:1 ratio to about a 1:1 ratio of EPA:DHA, or from about a 1.5:1 ratio to about a 1:1 ratio of EPA:DHA. In another embodiment, the omega-3 ester or omega-3 alkyl ester has at least about a 1:5 ratio of EPA:DHA, at least about a 1:1 ratio of EPA:DHA, at least about a 1.5:1 ratio of EPA:DHA, at least about a 2:1 ratio of EPA:DHA, at least about a 3:1 ratio of EPA:DHA, at least about a 5:1 ratio of EPA:DHA, or at least about a 10:1 ratio of EPA:DHA.

The invention provides novel and unexpected omega-3 ester-based medicaments of one or more statins. These medicaments are readily bioavailable. Notably, because the medicaments of the invention contain an omega-3 ester-based oil as the major ingredient, they not only provide an antihypercholesterolemic effect due to the statin active ingredient, they also provide recommended daily dosages of omega-3 oils (i.e., one gram of omega-3 oil per day, as per AHA guidelines), or a portion thereof.

In another embodiment, the present invention provides a salt of a statin. In another embodiment, the present invention provides a salt of pravastatin or fluvastatin. In a specific embodiment, a calcium salt of pravastatin is provided. In another specific embodiment, a magnesium salt of pravastatin is provided. In another specific embodiment, a zinc salt of pravastatin is provided. In another specific embodiment, a calcium salt of fluvastatin is provided. In another embodiment, a divalent salt of a statin is provided. In a specific embodiment, a divalent salt of pravastatin or fluvastatin is provided. In another embodiment, the salt of a statin is amorphous. In another embodiment, the salt of a statin is crystalline.

In another embodiment, the present invention provides a solvate, a hydrate, a co-crystal, or a polymorph of a salt of a statin. In another embodiment, the present invention provides a solvate, a hydrate, a co-crystal, or a polymorph of a salt of pravastatin or fluvastatin. In a specific embodiment, a solvate, a hydrate, a co-crystal, or a polymorph of a calcium salt of pravastatin is provided. In another specific embodiment, a solvate, a hydrate, a co-crystal, or a polymorph of a magnesium salt of pravastatin is provided. In another specific embodiment, a solvate, a hydrate, a co-crystal, or a polymorph of a zinc salt of pravastatin is provided. In another specific embodiment, a solvate, a hydrate, a co-crystal, or a polymorph of a calcium salt of fluvastatin is provided. In another embodiment, a solvate, a hydrate, a co-crystal, or a polymorph of a divalent salt of a statin is provided. In a specific embodiment, a solvate, a hydrate, a co-crystal, or a polymorph of a divalent salt of pravastatin or fluvastatin is provided. In another embodiment, the solvate or hydrate of the salt of a statin is amorphous. In another embodiment, the solvate or hydrate of the salt of a statin is crystalline.

In another embodiment, a pharmaceutical composition or a medicament comprising a salt of a statin is provided. In another embodiment, a pharmaceutical composition or a medicament comprising a solvate, a hydrate, a co-crystal, or a polymorph of a salt of a statin is provided. In another embodiment, a pharmaceutical composition or a medicament comprising a solvate, a hydrate, a co-crystal, or a polymorph of a salt of a statin and an omega-3 oil is provided.

In another embodiment, the present invention provides a method for preparing a salt of a statin.

In another embodiment, a method for preparing a salt of a statin comprises:
(a) combining a statin and a salt in solution;
(b) initiating precipitation of a salt of said statin; and
(c) collecting said salt of said statin.

In another embodiment, the statin in step (a) can be a salt. For example, the statin in step (a) can be an alkali metal salt of a statin, such as, but not limited to, pravastatin sodium salt or fluvastatin sodium salt. In another embodiment, the salt in step (a) can be an alkaline earth metal salt. For example, the salt in step (a) can be a calcium or a magnesium salt, such as, but not limited to, calcium acetate or calcium chloride.

In another embodiment, a method of preventing, reducing, and/or treating elevated cholesterol levels (such as in hypercholesterolemia), atherosclerosis, hyperlipidemia, cardiovascular events and disease including coronary events and cerebrovascular events, and coronary artery disease and/or cerebrovascular disease is provided by administering a pharmaceutical composition of the present invention to a mammal in need of such prevention, reduction, and/or treatment.

These and other embodiments are described in greater detail in the following detailed description.

DETAILED DESCRIPTION OF THE INVENTION

Figure 1:
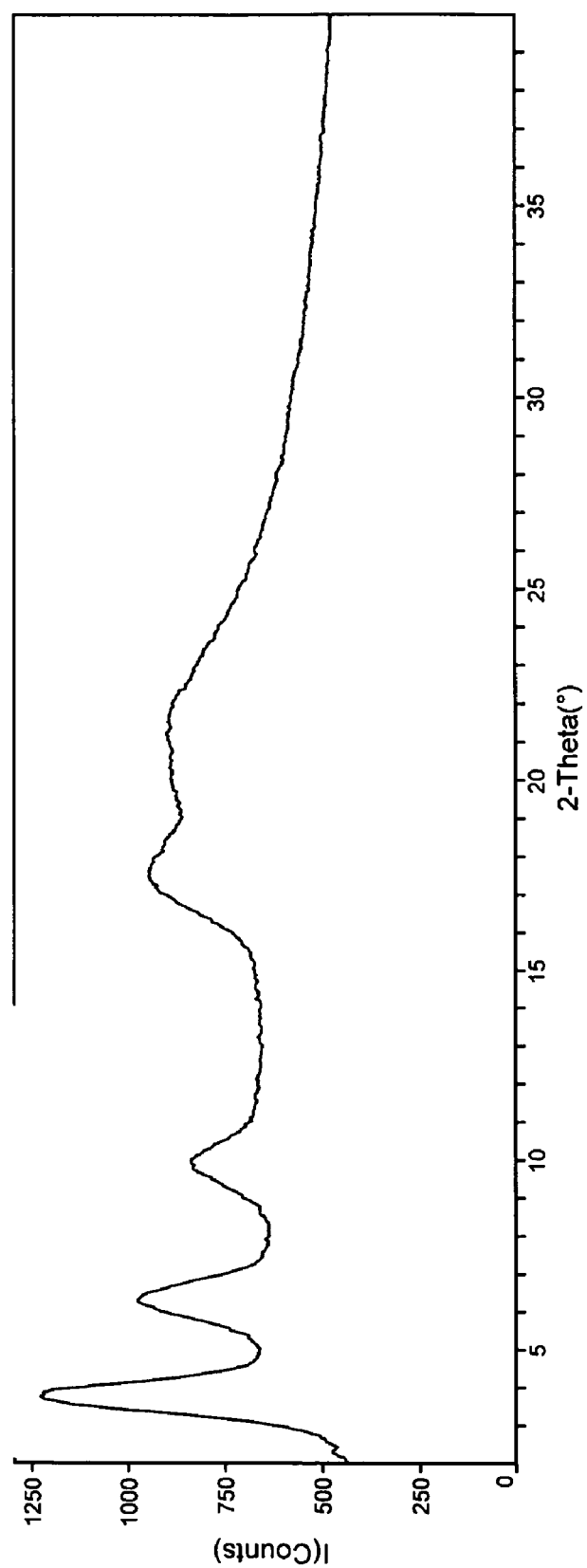
FIG. 1 shows a PXRD diffractogram of a pravastatin calcium salt.

As used herein, the following terms have the following respective meanings.

The terms "cardiovascular event(s)" and "cardiovascular disease" as employed herein refer to coronary and/or cerebrovascular event(s) and disease including primary myocardial infarction, secondary myocardial infarction, myocardial ischemia, angina pectoris (including unstable angina), congestive heart failure, sudden cardiac death, cerebral infarction, cerebral thrombosis, cerebral ischemia, transient ischemic attack and the like.

The term "coronary artery disease" (CAD) as employed herein refers to diseases including atherosclerosis of the coronary arteries, previous myocardial infarction, ischemia, angina pectoris and/or heart failure.

The term "cerebrovascular disease" as employed herein refers to diseases including atherosclerosis of the intracranial and/or extracranial arteries, cerebral infarction, cerebral thrombosis, cerebral ischemia, stroke, and/or transient ischemic attacks.

"Alkyl" means a straight chain or branched, saturated or unsaturated alkyl, cyclic or non-cyclic hydrocarbon having from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (also referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1butynyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cycloalkyls are also referred to herein as "carbocyclic" rings systems, and include bi- and tri-cyclic ring systems having from 8 to 14 carbon atoms such as a cycloalkyl (such as cyclopentane or cyclohexane) fused to one or more aromatic (such as phenyl)

or non-aromatic (such as cyclohexane) carbocyclic rings. "Alkenyl" can be used in the context of omega-3 formulations to refer to unsaturation.

As used herein, the term "adjunctively administered" refers to the administration of one or more compounds or active ingredients in addition to a pharmaceutically acceptable salt, solvate, co-crystal, or polymorph of a racemate or stereoisomer of a statin, preferably a salt of a statin, either simultaneously with the same or at intervals prior to, during, or following administration of the pharmaceutically acceptable salt, solvate, or polymorph of a racemate or stereoisomer of a statin to achieve the desired therapeutic or prophylactic effect.

"Fatty acids" are an important component of nutrition. Fatty acids (also described as "free acids" or "free fatty acids") are carboxylic acids and are classified based on the length and saturation characteristics of the carbon chain. Short chain fatty acids have 2 to about 5 carbons and are typically saturated. Medium chain fatty acids have from about 6 to about 14 carbons and are also typically saturated. Long chain fatty acids have from about 15 to 24 or more carbons and may also be saturated or unsaturated. In longer fatty acids there may be one or more points of unsaturation, giving rise to the terms "monounsaturated" and "polyunsaturated", respectively. Long chain polyunsaturated fatty acids (LCPs or LC-PUFAs) having 20 or more carbons are used in the instant invention.

"Long chain" mono-, di-, tri-glycerides, esters, fatty acids, etc. are defined as having about 15, 16, 17, 18, 19, 20, 21, 22, 23, 24 or more carbons and may also be saturated or unsaturated. "Medium chain" mono-, di-, tri-glycerides, esters, fatty acids, etc. are defined as having about 6, 7, 8, 9, 10, 11, 12, 13, or 14 carbons and may also be saturated or unsaturated. "Short chain" mono-, di-, tri-glycerides, esters, fatty acids, etc. are defined as having about 2, 3, 4, or 5, carbons and may also be saturated or unsaturated.

"Mono-diglyceride" and "mono-diglycerides" refer to a mixture or mixtures comprising both monoglycerides and diglycerides. A non-limiting example of a mono-diglyceride is Capmul® MCM, which comprises a mixture of caprylic and capric fatty acids in the form of monoglycerides and diglycerides. Certain mixtures of monoglycerides and diglycerides may be specifically stated as mono-diglycerides according to the present invention. Mono-diglycerides can comprise other species such as, for example, triglycerides and glycerol.

LC-PUFAs are categorized according to the number and position of double bonds in the fatty acids according to an accepted nomenclature that is well-known to those of ordinary skill in the art. There are two series or families of LC-PUFAs, depending on the position of the double bond closest to the methyl end of the fatty acid: the n-3 series contains a double bond at the third carbon, while the n-6 series has no double bond until the sixth carbon. Thus, arachidonic acid (AA or ARA) has a chain length of 20 carbons and 4 double bonds beginning at the sixth carbon. As a result, it is referred to as "20:4 n-6". Similarly, docosahexaenoic acid (DHA) has a chain length of 22 carbons with 6 double bonds beginning with the third carbon from the methyl end and is thus designated "22:6 n-3". Another important LC-PUFA is eicosapentaenoic acid (EPA) which is designated (20:5 n-3). The terms "n-3" and "omega-3" are used interchangeably.

The biosynthetic pathways for AA (n-6 series) and DHA (n-3 series) from their respective C18 precursors are distinct, but share elongation and desaturation steps and are well understood. Thus, other important LCPs are the C18 fatty acids that are precursors in these biosynthetic pathways, for example, linoleic (18:2 n-6) and gamma-linolenic (18:3 n-6) acids in the n-6 pathway, and alpha-linolenic (18:3 n-3) and stearidonic (18:4 n-3) in the n-3 pathway.

Fatty acids are often found in nature as acyl radicals esterified to alcohols. A glyceride is such an ester of one or more fatty acids with glycerol (1,2,3-propanetriol). If only one position of the glycerol backbone molecule is esterified with a fatty acid, a "monoglyceride" is produced; if two positions are esterified, a "diglyceride" is produced; and if all three positions of the glycerol are esterified with fatty acid a "triglyceride" or "triacylglycerol" is produced. A glyceride is called "simple" if all esterified positions contain the same fatty acid; or "mixed" if different fatty acids are involved. A phospholipid is a special type of diglyceride, wherein the third position on the glycerol backbone is bonded to a nitrogen containing compound such as choline, serine, ethanolamine, inositol, etc., via a phosphate ester. Triglycerides and phospholipids are often classified as long chain (from about 15 to 24 or more carbons) or medium chain (from about 6 to about 14 carbon), according to the fatty acids attached thereto.

Typically commercially available monoglycerides contain varying amounts of di- and triglycerides in addition to their monoglyceride content. For example, a monoglyceride (e.g., Akoline, by Karlshamns AB, Sweden) can comprise about 50-65% monoglyceride, 25-35% diglyceride, and up to 5% triglycerides.

The "essential fatty acids" (EFAs) are of two types, the n-3 (or omega-3) series derived from alpha-linolenic acid and the n-6 (or omega-6) series derived from linoleic acid.

An "omega-3 fatty acid" is a n-3 polyunsaturated long-chain fatty acids (n-3 PUFA) and is defined to include any carboxylic acid having at least 15 carbon atoms and having at least 3 non-conjugated cis-unsaturated bonds, the distal one of which from the methyl end of the fatty acid chain being located between the third and fourth carbon atoms. The omega-3 fatty acids therefore include $C_{16}$-$C_{24}$ alkanoic acids comprising 5-7 double bonds, wherein the last double bond is located between the third and fourth carbon atom from the methyl end of the fatty acid chain.

Examples of omega-3 fatty acids include stearidonic acid (SDA, C18:4), eicosatetraenoic acid (ETA, C20:4), eicosapentaenoic acid (EPA, C20:5), docosapentaenoic acid (DPA, C22:5), and docosahexaenoic acid (DHA, C22:6). For the purpose of the invention, alpha-linolenic acid (ALA, C18:3) is considered an omega-3 fatty acid. Terms such as "EPA" and "DHA" denote species of omega-3 oil and do not describe whether such oils exist as, for example, triglycerides, diglycerides, monoglycerides, free acids, esters, or salts.

Omega-3 fatty acids include synthetic or naturally occurring omega-3 fatty acids, such as those found in fish oil, e.g., marine mammal (e.g., seal) fat, cod liver oil, walnuts and walnut oil, wheat germ oil, rapeseed oil, soybean lecithin, soybeans, tofu, common beans, butternuts, seaweed and flax seed oil. An omega-3 fatty acid may also be derived from genetically engineered sources such as transgenic plants. See, e.g., Frasier, et al., *Nat Biotechnol.* 2004 May 16.

An "omega-3 oil" or "omega-3" is any oil comprising a source of omega-3 fatty acids, omega-3 esters, omega-3 alkyl esters, or omega-3 mono-, di-, or triglycerides, such as fish oil, e.g., marine mammal (e.g., seal) fat, cod liver oil, walnuts and walnut oil, wheat germ oil, rapeseed oil, soybean lecithin derived oils, soybean derived oils, tofu derived oils, common bean derived oils, butternut derived oils, seaweed derived oils, flax-borage oil, and flax seed oil. The Epax® (Pronova Biocare AS) brand of omega-3 oils are preferred. Other omega-3 oils which can be used in making pharmaceutical compositions of the invention include, but are not limited to, the omega-3 oil marketed under the tradename Omegabrite® (Omega Natural Science) and Epanova™ (Tillotts Pharma AG). Certain mixtures of esters, fatty acids, and/or mono- di-triglycerides may be specifically stated as oils according to the present invention. For example, a mixture consisting of omega-3 esters and fatty acids may be considered an omega-3 oil according to the present invention. In addition, one or more components may be specifically excluded from an omega-3 oil according to the present invention. For example, an omega-3 oil may specifically exclude esters, fatty acids, and/or mono- di-triglycerides according to the present invention. As such, a composition consisting of omega-3 esters, for example, is an omega-3 oil according to the present invention.

An "omega-3 alkyl ester" may be formed by transesterification of an omega-3 oil and an alcohol (preferably methanol or ethanol) and either an acid or reducing agent. Because formation of lower alkyl esters is generally preferred, the alcohol preferably is a lower alkyl alcohol containing from 1 to 6 carbon atoms. More preferably, the alcohol is methanol (which reacts with glycerides to form methyl esters of the fatty acid residues) or ethanol (which reacts with glycerides to form ethyl esters of the fatty acid residues). Most preferably, the alcohol is ethanol.

The term "crystalline" used throughout the specification and claims includes solids described as "weakly crystalline."

The term "alkali metal salt" includes, but is not limited to, a salt where the counterion is Li, Na, K, Rb, or another Group IA counterion.

The term "alkaline earth metal salt" includes, but is not limited to, a salt where the counterion is Be, Mg, Ca, Sr, or another Group IIA counterion.

The term "divalent" is used to describe the oxidation state of a metal ion and includes, but is not limited to, $Mg^{2+}$, $Ca^{2+}$, $Zn^{2+}$, $Be^{2+}$, and $Sr^{2+}$.

Pharmaceutical compositions and medicaments may be described as mixtures of two or more components "by volume," which is herein defined as the volume due to one component divided by the volume of all components of the composition. This ratio may be converted to or reported as a percentage of the total composition volume. Such a quantity may also be indicated by "v/v" or "percent v/v." Similarly, the phrases "by weight" and "by mass" describe the weight or mass due to one component divided by the weight or mass of all components of the composition. This ratio may be converted to or reported as a percentage of the total composition weight or mass. Such a quantity may also be indicated by "w/w", "mass percent," or "percent w/w."

The terms "pharmaceutical composition" and "formulation" are used interchangeably throughout the specification and claims.

The term "E463808" is used to described an omega-3 oil which has a composition comprising 46% EPA, 38% DHA, and 8% other omega-3 oils (mass percent) where the EPA, DHA, and other omega-3 oils are ethyl esters.

The term "E681010" is used to describe an omega-3 oil which has a composition comprising 67.8 percent EPA (mg/g), 9.9 percent DHA (mg/g), and about 9.6 percent other omega-3 oils (mg/g), where the EPA, DHA, and other omega-3 oils are ethyl esters.

The terms "chemically stable" or "chemical stability" refer to a liquid formulation where there is a ≦3.0 percent loss of API potency (recovered API content) after 2 years at 25 degrees C.

"Surfactants" and "a surfactant of the invention" refer to a surface active compound which can alter the surface tension of a liquid in which it is dissolved and includes, but is not limited to, polyoxyl 20 stearate, polyoxyl 35 castor oil, poloxamers, polyoxyethylene sorbitan monoisostearate, polyethylene glycol 40 sorbitan diisostearate, polyoxyl 40 hydrogenated castor oil, polysorbate, polysorbate 20, polysorbate 40, polyoxyl 60 stearate, polysorbate 85, polysorbate 60, poloxamer 331, polyoxyethylene fatty acid esters, polyoxyl 40 castor oil, poloxamer 188, polyoxyethylene polyoxypropylene 1800, oleic acid, sodium desoxycholate, sodium lauryl sulfate, sorbitan monolaurate, sorbitan monooleate, sorbitan monopalmitate, sorbitan trioleate, N-carbamoyl methoxypolyethylene glycol 2000-1,2-distearol, myristic acid, steareth, polyoxyl 40 stearate, sucrose stearate, tocopherol, polyoxyl castor oil, triglyceride synthetic, trimyristin, tristearin, magnesium stearate, lecithin, lauryl sulfate, vitamin E, egg yolk phosphatides, docusate sodium, polysorbate 80, dimyristoyl phosphatidylglycerol, dimyristoyl lecithin, Capryol 90 (propylene glycol monocaprylate), Capryol PGMC (propylene glycol monocaprylate), deoxycholate, cholesterol, Cremophor RH, Cremophor EL, propylene glycol alginate, Croval A-10 (PEG 60 almond glycerides), Labrafil 1944 (oleoyl macrogol-6 glycerides), Labrafil 2125 (linoleoyl macrogol-6 glycerides), Labrasol (caprylocaproyl macrogol-8 glycerides), Lauroglycol 90 (propylene glycol monolaurate), Lauroglycol FCC (propylene glycol laurate), calcium stearate, Lecithin Centromix E, Lecithin Centrophase 152, Lecithin Centrol 3F21B, POE 26 glycerin, Olepal isosteariques (PEG-6 isostearate), Plurol diisostearique (polyglycerol-3-diisostearate), Plurol Oleique CC, POE 20 Sorbitan trioleate, Tagat TO (polyoxyethylene glycerol trioleate), or Solutol (Macrogol-15 hydroxystearate).

Surfactants also include, but are not limited to, polyoxyethylene 20 sorbitan monoleate, polyoxyethylene alkyl ethers of the Brig- or Volpo series, polyoxyethylene sorbitant fatty acid esters of the Tween- or Crillet series, polyoxyethylene stearates of the Cerosynt- or Myrj series, lecithin, poloxamers, d-alpha-tocopheryl polyethylene glycol 1000 succinate (Vitamin E TPGS, TPGS), saturated polyglycolized glycerides (Labrasol, Labrafil and Gelucires), cholic acid and salts of cholic acid, deoxycholic acid and salts of deoxycholic acid, taurocholic acid, salts of taurocholic acid, glycocholic acid, polyvinylpyrrolidone, cocamines, glyceryl stearates, glyceryl oleates, hydrogenated lanolins, lanolins, laurates and oleates, sorbitan laurates, sorbitan palmitates, sorbitan stearates, quatemium surfactants, sodium sulfates, glyceryl compounds, palmitic acid and its derivatives and oleic acid and its derivatives.

PEG-containing surfactants include, but are not limited to, Tween 85®, Tween 80®, and Cremophor®EL.

Surfactants may be included in a pharmaceutical composition of the invention, for example, to facilitate digestion or to reduce the food effect.

The term "aqueous solubility" refers to the solubility as measured in deionized water at about 25 degrees C., unless otherwise specified.

Acid-catalyzed transesterification may be carried out, for example, by incubating a triglyceride at from about 0° C. to about 150° C. in a mixture containing the alcohol and an acid (e.g., HCl), preferably under a non-oxidizing atmosphere and in the absence of water. In one embodiment, the triglyceride/acid/alcohol mixture is refluxed for at least about 2 hours. In another embodiment, the triglyceride/acid/alcohol mixture is maintained at from about 0° C. to about 50° C. overnight. Methanol may be used to form methyl esters, and ethanol may be used to form ethyl esters. Because acid-catalyzed transesterification is typically reversible, the alcohol preferably is present in a large excess so that the reaction proceeds essentially to completion. Preferably, the triglyceride concentration in the alcohol/acid mixture is from about 0.1 to about 15% by weight, and most preferably about 3% by weight. If the acid is HCl, the concentration of HCl in the alcohol/HCl mixture preferably is from about 4 to about 15% by weight, and most preferably about 10% by weight. Such a mixture may be prepared by various methods known in the art, such as bubbling dry gaseous hydrogen chloride into dry ethanol, or adding 1 mL of acetylchloride to each 10 mL of alcohol (to form approximately 10% by weight HCl in alcohol).

Although HCl is most preferred, other acids may alternatively be used. One such acid is sulfuric acid, which typically is used at a concentration of from about 0.5 to about 5% by weight in the alcohol. It should be noted, however, that because sulfuric acid is a strong oxidizing agent, it preferably is not used with long reflux times (i.e., greater than about 6 hours), at high concentrations (i.e., greater than about 5% by weight), or at high temperatures (i.e., greater than 150° C.). Another example of a suitable acid is boron trifluoride, which preferably is used at a concentration of from about 1 to about 20% by weight in the alcohol. Boron trifluoride, however, is less preferred than HCl because boron trifluoride has a greater tendency to produce undesirable byproducts.

In base-catalyzed transesterification, the omega-3 oil is transesterified by an alcohol in the presence of a basic catalyst. In this instance, the base may be, for example, sodium methoxide, potassium methoxide, elemental sodium, sodium hydroxide, or potassium hydroxide. Preferably, the volumetric ratio of omega-3 oil to the base/alcohol mixture is at least about 1:1, and most preferably about 1:2. The concentration of the base in the alcohol preferably is from about 0.1 to about 2 M. The base-catalyzed transesterification reaction can be conducted at room temperature (i.e., at a temperature of from about 20° to about 25° C.) for from about 6 to about 20 hours. Alternatively, the base-catalyzed transesterification reaction is conducted at a temperature greater than room temperature. The glyceride/alcohol/catalyst solution preferably is heated to a temperature of at least about 40° C., more preferably from about 70 to about 150° C., and most preferably at about 100° C. The solution can be heated using a reflux condenser so that the reaction mixture may be heated to temperatures above the boiling point of one or more components in the mixture without losing the components into the vapor phase (i.e., when the components vaporize, they rise into the reflux condenser which has a cooler temperature, thereby causing the vapor to condense into a liquid and flow back into the liquid mixture).

During the transesterification reaction, the reacting mixture is preferably placed under a non-oxidizing atmosphere, such as an atmosphere consisting essentially of a noble gas, $N_2$, or a combination thereof. Use of such an atmosphere is particularly preferred if the transesterification reaction is conducted over a period of time exceeding about 10 minutes. An oil-soluble antioxidant (e.g., ascorbyl palmitate or propyl gallate) may also be added to the reacting mixture to prevent auto-oxidation, and is particularly preferred where a non-oxidizing atmosphere is not used.

Omega-3 alkyl esters include the ethyl esters of EPA and DHA. The E463808, OMEGA-3/90 (K D Pharma), and Incromega (Croda/Bioriginal) omega-3 ethyl esters are several exemplary omega-3 alkyl esters.

The present invention comprises a suspension of one or more salts of a statin(s) in an omega-3 oil. In one embodiment, the suspension comprises solid crystalline particles of one or more salts of a statin(s) in an omega-3 oil. In another embodiment, the suspension comprises solid amorphous particles of one or more salts of a statin(s) in an omega-3 oil. In another embodiment, the suspension comprises solid crystalline and solid amorphous particles of one or more salts of a statin(s) in an omega-3 oil. Also included in the present invention are pharmaceutical compositions comprising suspensions of one or more salts of a statin(s) in an omega-3 oil where a portion of said one or more salts of a statin(s) is solubilized in the omega-3 oil or in another component of the composition. For example, in another embodiment, the present invention provides a pharmaceutical composition comprising an omega-3 oil and one or more salts of a statin(s), wherein about 1.00, 2.00, 3.00, 4.00, 5.00, 6.00, 7.00, 8.00, 9.00, 10.00, 11.00, 12.00, 13.00, 14.00, or 15.00 percent statin(s) by weight is/are in solution while the remaining statin(s) is/are present in suspension.

In another embodiment, the present invention provides a pharmaceutical composition comprising an omega-3 oil and one or more salts of a statin(s), wherein at least about 80 percent of the statin(s) by weight are present as solid particles in suspension. In another embodiment, the present invention provides a pharmaceutical composition comprising an omega-3 oil and one or more salts of a statin(s), wherein at least about 85 percent of the statin(s) by weight are present as solid particles in suspension. In another embodiment, the present invention provides a pharmaceutical composition comprising an omega-3 oil and one or more salts of a statin(s), wherein at least about 90 percent of the statin(s) by weight are present as solid particles in suspension. In another embodiment, the present invention provides a pharmaceutical composition comprising an omega-3 oil and one or more salts of a statin(s), wherein at least about 95 percent of the statin(s) by weight are present as solid particles in suspension. In another embodiment, the present invention provides a pharmaceutical composition comprising an omega-3 oil and one or more salts of a statin(s), wherein at least about 99 percent of the statin(s) by weight are present as solid particles in suspension.

In another embodiment, a specific salt of a statin may, optionally, be specifically excluded from the present invention. For example, pravastatin sodium may be specifically excluded from the present invention.

Oil purity is an important aspect of the present invention. Oil purity is defined as a percentage (e.g., by volume or by weight) of one component with respect to the entire oil composition. Several examples of oil components include, but are not limited to, monoglycerides, diglycerides, triglycerides, free acids, esters, and derivatives, precursors, and salts thereof. For example, an ester oil with a purity of 95 percent by weight comprises at least 95 percent esters. The remaining percentage may comprise free acids, mono- di- and/or triglycerides, or other components. As another example, an omega-3 ester oil with a purity of 90 percent by weight comprises at least 90 percent omega-3 esters and the remaining percentage can comprise any one or more of other oil components. A mixture of species of one component (e.g., $C_8$ and $C_{10}$ esters) need not be discerned in the determination of purity. However, a distinction of specific species within a component (e.g., $C_8$ and $C_{10}$ esters) can also be included in specific embodiments of the present invention.

According to the present invention, omega-3 oils with a purity greater than about 85 percent, 90 percent, 91 percent, 92 percent, 93 percent, 94 percent, 95 percent, 96 percent, 97 percent, 98 percent, 99 percent or more are preferred. Omega-3 oils with a high purity of omega-3 esters are preferred. According to the present invention, omega-3 oils with a high purity comprise greater than about 85 percent, 90 percent, 91 percent, 92 percent, 93 percent, 94 percent, 95 percent, 96 percent, 97 percent, 98 percent, 99 percent or more of one component by weight or by volume. Preferred omega-3 esters include, but are not limited to, EPA and DHA. More preferred omega-3 esters include omega-3 ethyl esters.

Oil composition is another important aspect of the present invention. Oil composition can be described as both the species and the components of an oil. Species include specific omega-3 oils such as, but not limited to, EPA, DHA, linoleic acid, linolenic acid, etc. Components include, but are not limited to, monoglycerides, diglycerides, triglycerides, free acids, esters, and derivatives, precursors, and salts thereof. For example, E463808 comprises about 46% EPA and about 38% DHA (mass percent) as ethyl esters. The remaining portion consists essentially of omega-3 oils other than EPA and DHA and other non-omega-3 oils. Other commercially available omega-3 oils contain higher or lower levels of total EPA and DHA as components such as monoglycerides, diglycerides, triglycerides, esters, free acids, etc. or mixtures thereof. Omega-3 oils with a composition comprising a mass percent of EPA and DHA equal to or greater than about 55 percent are preferred. Omega-3 oils with a composition comprising a mass percent of EPA and DHA equal to or greater than about 75 percent are more preferred. Omega-3 oils with a composition comprising a mass percent of EPA and DHA equal to or greater than about 80 percent are most preferred.

Mixtures of omega-3 alkyl esters with other forms of omega-3 oil (e.g., fatty acids, triglycerides) are included, according to the present invention. Oils containing highly pure or pure alkyl esters are included in the present invention.

In another embodiment, the purity of omega-3 esters or omega-3 alkyl esters is at least about 50 percent by weight, at least about 60 percent by weight, at least about 70 percent by weight, at least about 75 percent by weight, at least about 80 percent by weight, or at least about 85 percent by weight. In another embodiment, the purity of omega-3 esters or omega-3 alkyl esters is about 25, 30, 35, 40, 45, 50, 55, 60, 65, 70, 75, 80, 85, 90, 95, 99 percent or more by weight. In another embodiment, the purity of omega-3 esters or omega-3 alkyl esters is between about 25 and about 100 percent by weight, between about 40 and about 100 percent by weight, between about 50 and about 100 percent by weight, between about 60 and about 100 percent by weight, between about 70 and about 100 percent by weight, between about 75 and about 100 percent by weight, between about 75 and about 95 percent by weight, between about 75 and about 90 percent by weight, or between about 80 and about 85 percent by weight. In another embodiment, the purity of omega-3 esters or omega-3 alkyl esters is about 100 percent by weight, about 99 percent by weight, about 96 percent by weight, about 92 percent by weight, about 90 percent by weight, about 85 percent by weight, about 80 percent by weight, about 75 percent by weight, about 70 percent by weight, about 65 percent by weight, about 60 percent by weight, about 55 percent by weight, or about 50 percent by weight.

In another embodiment, the oil composition comprising EPA and DHA is at least about 50 percent by weight, at least about 60 percent by weight, at least about 70 percent by weight, at least about 75 percent by weight, at least about 80 percent by weight, or at least about 84 percent by weight. In another embodiment, the oil composition comprising EPA and DHA is about 25, 30, 35, 40, 45, 50, 55, 60, 65, 70, 75, 80, 85, 90, or 95 percent by weight. In another embodiment, the oil composition comprising EPA and DHA is between about 25 and about 95 percent by weight, between about 40 and about 95 percent by weight, between about 50 and about 95 percent by weight, between about 60 and about 95 percent by weight, between about 70 and about 95 percent by weight, between about 75 and about 95 percent by weight, between about 75 and about 90 percent by weight, between about 75 and about 85 percent by weight, or between about 80 and about 85 percent by weight. In another embodiment, the oil composition comprising EPA and DHA is about 99 percent by weight, about 96 percent by weight, about 92 percent by weight, about 90 percent by weight, about 84 percent by weight, about 80 percent by weight, about 75 percent by weight, about 70 percent by weight, about 65 percent by weight, about 60 percent by weight, about 55 percent by weight, or about 50 percent by weight.

In another embodiment, the omega-3 ester or omega-3 alkyl ester has about a 23:19 ratio of EPA:DHA, about a 75:11 ratio of EPA:DHA, about a 95:1 ratio of EPA:DHA, about a 9:2 ratio of EPA:DHA, about a 10:1 ratio of EPA:DHA, about a 5:1 ratio of EPA:DHA, about a 3:1 ratio of EPA:DHA, about a 2:1 ratio of EPA:DHA, about a 1:1 ratio of EPA:DHA, about a 1:2 ratio of EPA:DHA, about a 1:3 ratio of EPA:DHA, or about a 1:5 ratio of EPA:DHA. In another embodiment, the omega-3 ester or omega-3 alkyl ester has about a 95:1 ratio of EPA:DHA, about a 75:1 ratio of EPA:DHA, about a 50:1 ratio of EPA:DHA, about a 25:1 ratio of EPA:DHA, about a 20:1 ratio of EPA:DHA, about a 15:1 ratio of EPA:DHA, about a 10:1 ratio of EPA:DHA, about a 7.5:1 ratio of EPA:DHA, about a 5:1 ratio of EPA:DHA, about a 4:1 ratio of EPA:DHA, about a 3:1 ratio of EPA:DHA, about a 2:1 ratio of EPA:DHA, about a 1.5:1 ratio of EPA:DHA, about a 1:1 ratio of EPA:DHA, about a 1:1.5 ratio of EPA:DHA, about a 1:2 ratio of EPA:DHA, about a 1:3 ratio of EPA:DHA, or about a 1:5 ratio of EPA:DHA. In another embodiment, the omega-3 ester or omega-3 alkyl ester has from about a 95:1 ratio to about a 1:5 ratio of EPA:DHA, from about a 50:1 ratio to about a 1:1 ratio of EPA:DHA, from about a 25:1 ratio to about a 1:1 ratio of EPA:DHA, from about a 10:1 ratio to about a 1:1 ratio of EPA:DHA, from about a 5:1 ratio to about a 1:1 ratio of EPA:DHA, from about a 3:1 ratio to about a 1:1 ratio of EPA:DHA, from about a 2:1 ratio to about a 1:1 ratio of EPA:DHA, or from about a 1.5:1 ratio to about a 1:1 ratio of EPA:DHA. In another embodiment, the omega-3 ester or omega-3 alkyl ester has at least about a 1:5 ratio of EPA:DHA, at least about a 1:1 ratio of EPA:DHA, at least about a 1.5:1 ratio of EPA:DHA, at least about a 2:1 ratio of EPA:DHA, at least about a 3:1 ratio of EPA:DHA, at least about a 5:1 ratio of EPA:DHA, or at least about a 10:1 ratio of EPA:DHA.

In another embodiment, any one or more of the above mentioned or other specific ratio, composition, or purity of omega-3 oil may be specifically excluded from the present invention. For example, EPA:DHA ratios of 3.3:2, 2.1:1, 3.1:2, 1.9:1, 1.7:1, 1.4:1, 1.1:1, 1:1, and 1:1.8 may be specifically excluded from the present invention. EPA:DHA ratios of from about 1:1 to about 2:1 may also be specifically excluded. In addition, omega-3 oils comprising compositions with, for example, about 80.2, 83.4, 83.7, 86.6, 87.7, or 90.2 percent by weight from EPA and DHA may be specifically excluded from the present invention. An omega-3 oil comprising 90 percent (w/w) omega-3 ethyl esters with 46 percent EPA and 38 percent DHA (e.g., OMACOR®) may be specifically excluded from the present invention. Omega-3 oils comprising an EPA:DHA ratio equal to or greater than 2:1 may be specifically excluded from the present invention. For example, omega-3 oils with an EPA:DHA ratio of about 2:1, 2.5:1, 3:1, 3.5:1, 4:1, 4.5:1, 5:1 or higher may be specifically excluded. Omega-3 oils comprising EPA and DHA in an amount greater than or equal to 75, 80, 85, 90, 91, 92, 93, 94, or 95 percent by weight may be specifically excluded. Omega-3 oils comprising an EPA:DHA ratio equal to about 1:5, 4.5:1, 95:1, 7.5:1, or 1.21:1 may be specifically excluded from the present invention. Other commercially available omega-3 oils may also be specifically excluded according to the present invention including, but not limited to, those available from Croda International (England) and Pronova Biocare (Norway).

"Statin" as used herein includes, but is not limited to, pravastatin, fluvastatin, atorvastatin, lovastatin, simvastatin, rosuvastatin, and cerivastatin. Statins may be in the form of a salt, hydrate, solvate, polymorph, or a co-crystal. Statins may also be in the form of a hydrate, solvate, polymorph, or a co-crystal of a salt. Statins may also be present in the free acid or lactone form according to the present invention.

The terms "an effective amount", "therapeutic effective amount", or "therapeutically effective amount" shall mean an amount or concentration of a composition according to the present invention which is effective in producing a desired result within the context of its administration or use, including, for example, lowering blood plasma triglyceride levels and in providing recommended dietary levels of omega-3 oil. Thus, the term "effective amount" is used throughout the specification to describe concentrations or amounts of pharmaceutical compositions according to the present invention which may be used to produce a favorable change in the disease or condition treated, whether that change is a reduction in blood plasma triglyceride levels, an increase in blood plasma LDL levels, or other favorable physiological result.

The term "patient" includes an animal, preferably a mammal, most preferably a human.

"Enteric coating" refers to a means for protecting acid unstable medication from the attack of the gastric fluid. Many enteric coatings can rapidly release the active drug in the proximal part of the gastrointestinal canal. Many enteric coatings are known to those skilled in the art including, as non-limiting examples, coatings comprised of an anionic polymer of methacrylic acid and methacrylates comprising a carboxyl group. Eudragit® L100 (Rohm Pharma) is a preferred enteric coating.

AUC is the area under the plot of plasma concentration of drug (not logarithm of the concentration) against time after drug administration. The area is conveniently determined by the "trapezoidal rule": the data points are connected by straight line segments, perpendiculars are erected from the abscissa to each data point, and the sum of the areas of the triangles and trapezoids so constructed is computed. When the last measured concentration ($C_n$, at time $t_n$) is not zero, the AUC from $t_n$ to infinite time is estimated by $C_n/k_{el}$.

The AUC is of particular use in estimating bioavailability of drugs, and in estimating total clearance of drugs ($Cl_T$). Following single intravenous doses, $AUC=D/Cl_T$, where D is the dose, for single compartment systems obeying first-order elimination kinetics; alternatively, $AUC=C_0/k_{el}$, where $k_{el}$ is the drug elimination rate constant. With routes other than the intravenous, $AUC=F \cdot D/Cl_T$, where F is the absolute bioavailability of the drug.

The AUC of one or more statins can be used as an indicator of the relative bioavailability of a pharmaceutical composition of the present invention with respect to a reference composition (e.g., PRAVACHOL®).

In another embodiment, the present invention provides a salt of a statin. In a specific embodiment, a calcium salt of pravastatin is provided. In another specific embodiment, a magnesium salt of pravastatin is provided. In another specific embodiment, a zinc salt of pravastatin is provided. In another specific embodiment, a calcium salt of fluvastatin is provided. In another embodiment, a divalent salt of a statin is provided. In another embodiment, the salt of a statin is amorphous. In another embodiment, the salt of a statin is crystalline.

In another embodiment, a pharmaceutical composition or a medicament comprising a salt of a statin is provided.

In another embodiment, the present invention provides a method for preparing a salt of a statin.

In another embodiment, a method for preparing a salt of a statin comprises:
(a) combining a statin and a salt in solution;
(b) initiating precipitation of a salt of said statin; and
(c) collecting said salt of said statin.

In another embodiment, the statin in step (a) can be a salt. For example, the statin in step (a) can be an alkali metal salt of a statin, such as, but not limited to, pravastatin sodium salt or fluvastatin sodium salt. In another embodiment, the salt in step (a) can be an alkaline earth metal salt. For example, the salt in step (a) can be a calcium or a magnesium salt, such as, but not limited to, calcium acetate or calcium chloride.

In another embodiment, initiating precipitation in step (b) can be completed by cooling the solution, evaporating the solution or a portion thereof, or one or more of techniques known to one skilled in the art.

In another embodiment, collecting the salt in step (c) can be completed via filtration, decanting, or any one or more of techniques known to one skilled in the art.

In another embodiment, a pharmaceutical composition or medicament of the present invention comprises about 500, 600, 700, 800, 900, 1000, 1100, 1200, 1300, 1400, or 1500 mg of omega-3 ester and about 1, 2, 3, 4, 5, 10, 15, 20, 25, 30, 35, 40, 45, 50, 55, 60, 65, 70, 75, or 80 mg of a salt of pravastatin.

In another embodiment, a pharmaceutical composition or medicament of the present invention comprises about 500, 600, 700, 800, 900, 1000, 1100, 1200, 1300, 1400, or 1500 mg of omega-3 ester and about 1, 2, 3, 4, 5, 10, 15, 20, 25, 30, 35, 40, 45, 50, 55, 60, 65, 70, 75, 80, 90, 100, 110, 120, 130, 140, 150, or 160 mg of a salt of fluvastatin.

In another embodiment, a pharmaceutical composition or medicament of the present invention comprises about 500, 600, 700, 800, 900, 1000, 1100, 1200, 1300, 1400, or 1500 mg of omega-3 ethyl ester and about 1, 2, 3, 4, 5, 10, 15, 20, 25, 30, 35, 40, 45, 50, 55, 60, 65, 70, 75, 80, 90, 100, 110, 120, 130, 140, 150, or 160 mg of a salt of a statin(s).

According to the present invention, the mass of a salt of a statin is measured with respect to the mass of the free form. For example, an 80 mg amount of a salt of a statin refers to 80 mg of free form statin, without the mass of the cation being included.

In another embodiment, a thickener, such as, but not limited to, calcium carbonate or silicon dioxide, can be added to a pharmaceutical composition according to the present invention.

In another embodiment, a pharmaceutical composition or medicament of the present invention can be stored for up to 8 weeks at about 25 degrees C. with no detectable degradation of the statin(s). In another embodiment, a pharmaceutical composition of the present invention can be stored for up to 12 weeks at about 25 degrees C. with no detectable degradation of the statin(s). In another embodiment, a pharmaceutical composition of the present invention can be stored for up to 16 weeks at about 25 degrees C. with no detectable degradation of the statin(s). In another embodiment, a pharmaceutical composition of the present invention can be stored for up to 26 weeks at about 25 degrees C. with no detectable degradation of the statin(s).

In another embodiment, pravastatin calcium salt exhibits an unexpectedly high stability in a suspension of omega-3 oil relative to other pravastatin salts, as shown in the Exemplification. Surprisingly, a suspension of pravastatin calcium salt displays a higher stability in omega-3 oil than other pravastatin salts, such as the sodium and potassium salts. Pravastatin magnesium and zinc salts and fluvastatin calcium salt are also preferred statins according to the present invention.

In another embodiment, pravastatin zinc salt exhibits an unexpectedly high stability in a suspension of omega-3 oil and an alcohol relative to other pravastatin salts, as shown in the Exemplification. Surprisingly, a suspension of pravastatin zinc salt displays a higher stability in omega-3 oil than other pravastatin salts, such as the sodium, calcium, and potassium salts.

In another embodiment, a method of preventing, reducing, and/or treating elevated cholesterol levels (such as in hypercholesterolemia), atherosclerosis, hyperlipidemia, cardiovascular events and disease including coronary events and cerebrovascular events, and coronary artery disease and/or cerebrovascular disease is provided by administering a pharmaceutical composition of the present invention to a mammal in need of such prevention, reduction, and/or treatment. In another embodiment, the mammal is a human.

In another embodiment, the present invention includes a salt of a statin with an aqueous solubility less than about 200.00 mg/mL. For example, less than about 200.00, 190.00, 180.00, 170.00, 160.00, 150.00, 140.00, 130.00, 120.00, 110.00, 100.00, 90.00, 80.00, 75.00, 70.00, 65.00, 60.00, 55.00, 50.00, 45.00, 40.00, 35.00, or less than about 30.00 mg/mL. In another embodiment, the present invention includes a salt of a statin with an aqueous solubility less than about 25.00 mg/mL or an aqueous solubility ranging between about 0.10 mg/mL and about 25 mg/mL. In another embodiment, the present invention includes a salt of pravastatin with an aqueous solubility less than about 200.00 mg/mL. For example, less than about 200.00, 190.00, 180.00, 170.00, 160.00, 150.00, 140.00, 130.00, 120.00, 110.00, 100.00, 90.00, 80.00, 75.00, 70.00, 65.00, 60.00, 55.00, 50.00, 45.00, 40.00, 35.00, or less than about 30.00 mg/mL. In another embodiment, a pravastatin salt of the present invention has an aqueous solubility less than about 25.00 mg/mL or an aqueous solubility ranging between 0.10 mg/mL and about 25 mg/mL. In another embodiment, the present invention includes a statin salt or a pravastatin salt with an aqueous solubility less than (or less than about) 25.00, 24.00, 23.00, 22.00, 21.00, 20.00, 19.00, 18.00, 17.00, 16.00, 15.00, 14.00, 13.00, 12.00, 11.00, 10.00, 9.00, 8.00, 7.00, 6.00, 5.00, 4.00, 3.00, 2.00, 1.00, 0.90, 0.80, 0.70, 0.60, 0.50, 0.40, 0.30, 0.20, or 0.10 mg/mL (these solubility values are to be understood as including, and providing written support for any fractional solubility in intervals of 0.01 mg/mL and such solubilities have not been included herein for the sake of brevity and to refrain from unduly lengthening the specification). Insoluble salts (salts having a solubility of 0.00 mg/mL) are not included in the scope of the invention. The aforementioned range of aqueous solubilities from about 0.10 mg/mL to about 25.00 mg/mL is to be taken as including, and providing written description and support for, any fractional solubility, in intervals of 0.01 mg/mL, between about 0.10 mg/mL and about 25.00 mg/mL. Aqueous solubilities for the pravastatin salts of the invention can also be described as having an aqueous solubility of less than (or less than about) X.YZ mg/mL, where X is 1, 2, 3, 4, 5, 6, 7, 8, 9, 10, 11, 12, 13, 14, 15, 16, 17, 18, 19, 20, 21, 22, 23, 24 or 25, Y is 0, 1, 2, 3, 4, 5, 6, 7, 8 or 9, and Z is 0, 1, 2, 3, 4, 5, 6, 7, 8 or 9 (provided that when X is 0, Y and Z cannot both be 0 [i.e., X, Y and Z cannot each, independently, be 0])

In another embodiment, the present invention includes a salt of fluvastatin with an aqueous solubility less than about 200.00 mg/mL. For example, less than about 200.00, 190.00, 180.00, 170.00, 160.00, 150.00, 140.00, 130.00, 120.00, 110.00, 100.00, 90.00, 80.00, 75.00, 70.00, 65.00, 60.00, 55.00, 50.00, 45.00, 40.00, 35.00, or less than about 30.00 mg/mL. In another embodiment, the present invention includes a salt of fluvastatin with an aqueous solubility less than about 25.00 mg/mL or an aqueous solubility ranging between 0.10 mg/mL and about 25 mg/mL. In another embodiment, the present invention includes a fluvastatin salt with an aqueous solubility less than about 25.00, 24.00, 23.00, 22.00, 21.00, 20.00, 19.00, 18.00, 17.00, 16.00, 15.00, 14.00, 13.00, 12.00, 11.00, 10.00, 9.00, 8.00, 7.00, 6.00, 5.00, 4.00, 3.00, 2.00, 1.00, 0.90, 0.80, 0.70, 0.60, 0.50, 0.40, 0.30, 0.20, or 0.10 mg/mL (these solubility values are to be understood as including, and providing written support for any fractional solubility in intervals of 0.01 mg/mL and such solubilities have not been included herein for the sake of brevity and to refrain from unduly lengthening the specification). Insoluble salts (salts having a solubility of 0.00 mg/mL) are not included in the scope of the invention. The aforementioned range of aqueous solubilities from about 0.10 mg/mL and about 25.00 mg/mL is to be taken as including, and providing written description and support for, any fractional percentage, in intervals of 0.01 mg/mL, between about 0.10 mg/mL and about 25.00 mg/mL. Aqueous solubilities for the fluvastatin salts of the invention can also be described as having an aqueous solubility of less than (or less than about) X.YZ mg/mL, where X is 1, 2, 3, 4, 5, 6, 7, 8, 9, 10, 11, 12, 13, 14, 15, 16, 17, 18, 19, 20, 21, 22, 23, 24 or 25, Y is 0, 1, 2, 3, 4, 5, 6, 7, 8 or 9, and Z is 0, 1, 2, 3, 4, 5, 6, 7, 8 or 9 (provided that when X is 0, Y and Z cannot both be 0 [i.e., X, Y and Z cannot each, independently, be 0]).

In another embodiment, the present invention provides a pharmaceutical composition of a salt of a statin as described above where the salt of a statin has an aqueous solubility less than about 25 mg/mL.

In another embodiment, a pharmaceutical composition or medicament of the present invention comprises about 500, 600, 700, 800, 900, 1000, 1100, 1200, 1300, 1400, or 1500 mg of omega-3 oil and about 1, 2, 3, 4, 5, 10, 15, 20, 25, 30, 35, 40, 45, 50, 55, 60, 65, 70, 75, 80, 90, 100, 110, 120, 130, 140, 150, or 160 mg of a salt of a statin(s), where the salt has an aqueous solubility less than about 200 mg/mL. In another embodiment, a pharmaceutical composition or medicament of the present invention comprises about 500, 600, 700, 800, 900, 1000, 1100, 1200, 1300, 1400, or 1500 mg of omega-3 oil and about 1, 2, 3, 4, 5, 10, 15, 20, 25, 30, 35, 40, 45, 50, 55, 60, 65, 70, 75, 80, 90, 100, 110, 120, 130, 140, 150, or 160 mg of a salt of a statin(s), where the salt has an aqueous solubility less than about 50 mg/mL. In another embodiment, a pharmaceutical composition or medicament of the present invention comprises about 500, 600, 700, 800, 900, 1000, 1100, 1200, 1300, 1400, or 1500 mg of omega-3 oil and about 1, 2, 3, 4, 5, 10, 15, 20, 25, 30, 35, 40, 45, 50, 55, 60, 65, 70, 75, 80, 90, 100, 110, 120, 130, 140, 150, or 160 mg of a salt of a statin(s), where the salt has an aqueous solubility less than about 25 mg/mL. In a specific embodiment, a pharmaceutical composition or medicament of the present invention comprises about 500, 600, 700, 800, 900, 1000, 1100, 1200, 1300, 1400, or 1500 mg of omega-3 oil and about 1, 2, 3, 4, 5, 10, 15, 20, 25, 30, 35, 40, 45, 50, 55, 60, 65, 70, 75, 80, 90, 100, 110, 120, 130, 140, 150, or 160 mg of a salt of a statin(s), where the salt has an aqueous solubility of about 15-17 mg/mL. In another embodiment, a pharmaceutical composition or medicament of the present invention comprises about 500, 600, 700, 800, 900, 1000, 1100, 1200, 1300, 1400, or 1500 mg of omega-3 oil and about 1, 2, 3, 4, 5, 10, 15, 20, 25, 30, 35, 40, 45, 50, 55, 60, 65, 70, 75, 80, 90, 100, 110, 120, 130, 140, 150, or 160 mg of a salt of a statin(s), where the salt has an aqueous solubility of about 0.5 mg/mL. In another embodiment, a pharmaceutical composition or medicament of the present invention comprises about 500, 600, 700, 800, 900, 1000, 1100, 1200, 1300, 1400, or 1500 mg of omega-3 oil and about 1, 2, 3, 4, 5, 10, 15, 20, 25, 30, 35, 40, 45, 50, 55, 60, 65, 70, 75, 80, 90, 100, 110, 120, 130, 140, 150, or 160 mg of a salt of a statin(s), where the salt has an aqueous solubility of about 0.3 mg/mL.

A therapeutically acceptable daily dosage of omega-3 oil has been recommended or considered via several national and international groups including, but not limited to, the American Heart Association (AHA) and the International Society for the Study of Fattly Acids and Lipids (ISSFAL). Table 1 includes daily dosage amounts of omega-3 as considered/recommended via several organizations.

TABLE 1

Daily dosages of omega-3

| Omega-3 dose (grams)/day | Comment |
| --- | --- |
| 0.65 | ISSFAL consideration (1999) |
| 1.0 | AHA recommended (2000, 2004) |
| 1.8 | Omacor ® dose |
| 3.0 | FDA limit on daily consumption, general population |
| 3.6 | Omacor ® dose |

Pharmaceutical Compositions and Dosage Forms

Pharmaceutical dosage forms of the invention can be administered orally, parenterally, by inhalation, spray, topically, rectally, nasally, buccally, vaginally or via an implanted reservoir. Oral and parenteral pharmaceutical compositions and dosage forms are a preferred dosage form. Preferably, the oral dosage form is a homogeneous or a heterogeneous formulation, a parenteral dosage form, or a capsule formulation (including without limitation hard gelatin capsules, starch capsules, HPMC capsules, and soft elastic gelatin capsules). Other preferred dosage forms include an intradermal dosage form, an intramuscular dosage form, a subcutaneous dosage form, and an intravenous dosage form.

Pharmaceutical unit dosage forms of this invention are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: capsules, dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., non-aqueous liquid suspensions, solutions, and elixirs, and liquid dosage forms suitable for parenteral administration to a patient.

The composition, shape, and type of dosage forms of the invention will typically vary depending on their use. For example, a dosage form used in the acute treatment of a disease or disorder may contain larger amounts of the active ingredient than a dosage form used in the chronic treatment of the same disease or disorder. Similarly, a parenteral dosage form may contain smaller amounts of the active ingredient than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990) or Remington: The Science and Practice of Pharmacy, 19th ed., Mack Publishing, Easton Pa. (1995).

Typical dosage forms of the invention comprise from about 1 mg to about 160 mg, preferably in an amount of from about 5 mg to about 160 mg of a statin. For example, dosage forms comprising 5, 10, 15, 20, 25, 30, 35, 40, 45, 50, 55, 60, 65, 70, 75, 80, 90, 100, 110, 120, 130, 140, 150, or 160 mg of a statin or a salt of a statin are preferable.

Oral Dosage Forms

Pharmaceutical compositions of the invention that are suitable for oral administration can be presented as discrete dosage forms, such as, but not limited to, capsules as described above and liquids, such as but not limited to, syrups, elixirs, solutions or suspensions. Such dosage forms may be prepared by methods of pharmacy well known to those skilled in the art. See generally, Remington's Pharmaceutical Sciences, 18th ed., Mack Publishing, Easton Pa. (1990) or Remington: The Science and Practice of Pharmacy, 19th ed., Mack Publishing, Easton Pa. (1995).

Controlled Release Dosage Forms

Statins can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 Technomic Publishing, Lancaster, Pa.: 2000). In the present invention, greater targeting of the liver and the sites of lipid particle generation could be an advantage of controlled release.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with compositions of the invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions.

One embodiment of the invention encompasses a unit dosage form which comprises a statin, and one or more pharmaceutically acceptable excipients or diluents, wherein the pharmaceutical composition or dosage form is formulated for controlled-release. Specific dosage forms utilize an osmotic drug delivery system.

An example of a delayed-release dosage form that also functions as a time controlled-release dosage form is described in U.S. Pat. No. 5,366,738, herein incorporated by reference in its entirety. The controlled-release drug delivery device described in U.S. Pat. No. 5,366,738 is known as a gel extrusion module (GEM) delivery device. The GEM device is a drug delivery device for the controlled in situ production and release of a dispersion containing a beneficial agent such as a pharmaceutical drug comprising:

(A) a compressed core prepared from an admixture comprising:
  (i) a therapeutically effective amount of the beneficial agent; and
  (ii) a polymer which upon hydration forms gelatinous microscopic particles; and
(B) a water insoluble, water impermeable polymeric coating comprising a polymer and a plasticizer, which surrounds and adheres to the core, the coating having a plurality of formed apertures exposing between about 1 and about 75% of the core surface; and wherein the release rate of the beneficial agent from the device is a function of the number and size of the apertures.

In the GEM device, the polymer inside the compressed core is preferably selected from sodium polyacrylate, carboxypolymethylenes and the pharmaceutically acceptable salts thereof such as a sodium salt, wherein the carboxypolymethylenes are prepared from acrylic acid crosslinked with allylethers of sucrose or pentaerythritol, and more preferably it is selected from carboxypolymethylenes prepared from acrylic acid crosslinked with allylethers of sucrose or pentaerythritol, and the pharmaceutically acceptable salts thereof. Most preferably, CARBOPOL® 974P and pharmaceutically acceptable salts thereof, particularly the sodium salt, is used as the polymer inside the compressed core. In addition, the compressed core may also contain one or more polymer hydration modulating agents, anti-oxidants, lubricants, fillers and excipients. An optional subcoating may be applied to the compressed core prior to application of the water insoluble coating as an aid in the manufacturing process. The subcoating may be comprised of, for example, hydroxypropyl cellulose and hydroxypropylmethylcellulose. Additional coatings may be applied for aesthetic or functional purposes.

The water insoluble, water impermeable polymeric coating is preferably comprised of (1) a polymer selected from polyvinyl chloride, cellulose acetate, cellulose acetate butyrate, ethylcellulose and combinations of these polymers; and (2) a plasticizer selected from diethylphthalate, dibutylsebacate and triethylcitrate. More preferably, the polymeric coating is comprised of cellulose acetate butyrate and triethyl citrate. The GEM device does not function as an osmotic drug delivery device, hence the release function of the device depends on passage of fluids from the external environment of the body to the internal environment of the compressed core through the formed apertures. It is intended that the terms "water insoluble, water impermeable" used to describe the polymeric coating define a coating which is essentially water insoluble and water impermeable, meaning that the polymeric coating allows minimal to no passage of water through the coating from the external environment of the body to the internal environment of the compressed core, except for the fluid passage that occurs through the drilled apertures, during the period of time the drug is being released from the GEM device in the body. Any minimal amount of water that does pass through the water insoluble, water impermeable polymeric coating is insubstantial and does not significantly contribute to the function of the GEM device, i.e. the release rate of the drug through the apertures. Rather the release rate of the statin from the GEM device is primarily a function of the number and size of the apertures on the device.

For an elegant, aesthetically pleasing final product, an outer finish coat may finally be applied to the GEM delivery device containing colorants, waxes, and the like. The GEM device can also be enterically coated, either before or after the application of additional finish coatings. Even without enteric coating, extrusion of the polymer which carries the statin out from inside the compressed core of the GEM device does not occur to a substantial extent in the acidic pH of the stomach, therefore substantial release of the statin should not occur in the stomach. Further details and examples of the GEM delivery device are described in U.S. Pat. No. 5,366,738.

It is generally preferred that the process for preparing the pharmaceutical compositions include the use of a purge of an inert gas. Such inert gases are for example, nitrogen, argon, and the like. The use of an isolator to maintain low oxygen conditions is desirable, but not required for storage of the present pharmaceutical composition.

These and other embodiments of the invention are illustrated further in the following examples, which are illustrative and in no way limiting.

EXEMPLIFICATION

Materials and Methods.

Differential scanning calorimetric (DSC) analysis of the samples was performed using a Q1000 Differential Scanning Calorimeter (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/98/2000/NT, version 3.1E; Build 3.1.0.40 (2001 TA Instruments-Water LLC).

For the DSC analysis, the purge gas used was dry nitrogen, the reference material was an empty aluminum pan that was crimped, and the sample purge was 50 mL/minute.

DSC analysis of the sample was performed by placing the modafinil sample in an aluminum pan with a crimped pan closure. The starting temperature was typically 20 degrees C. with a heating rate of 10 degrees C./minute, and the ending temperature was 200 degrees C. All reported DSC transitions represent the temperature of endothermic or exothermic transition at their respective peaks with an error of +/−2 degrees C., unless otherwise indicated.

Thermogravimetric analysis (TGA) of samples was performed using a Q500 Thermogravimetric Analyzer (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/98/2000/NT, version 3.1E;Build 3.1.0.40 (2001 TA Instruments-Water LLC).

For the TGA experiments, the purge gas used was dry nitrogen, the balance purge was 40 mL/minute $N_2$, and the sample purge was 60 mL/minute $N_2$.

TGA was performed on the sample by placing the modafinil sample in a platinum pan. The starting temperature was typically 20 degrees C. with a heating rate of 10 degrees C./minute, and the ending temperature was 300 degrees C.

A powder X-ray diffraction (PXRD) pattern for the samples was obtained using a D/Max Rapid, Contact (Rigaku/MSC, The Woodlands, Tex., U.S.A.), which uses as its control software RINT Rapid Control Software, Rigaku Rapid/XRD, version 1.0.0 (1999 Rigaku Co.). In addition, the analysis software used were RINT Rapid display software, version 1.18 (Rigaku/MSC), and JADE XRD Pattern Processing, versions 5.0 and 6.0 ((1995-2002, Materials Data, Inc.).

For the PXRD analysis, the acquisition parameters were as follows: source was Cu with a K line at 1.5406 Å; x-y stage was manual; collimator size was 0.3 mm; capillary tube (Charles Supper Company, Natick, Mass., U.S.A.) was 0.3 mm ID; reflection mode was used; the power to the X-ray tube was 46 kV; the current to the X-ray tube was 40 mA; the omega-axis was oscillating in a range of 0-5 degrees at a speed of 1 degree/minute; the phi-axis was spinning at an angle of 360 degrees at a speed of 2 degrees/second; 0.3 mm collimator; the collection time was 60 minutes; the temperature was room temperature; and the heater was not used. The sample was presented to the X-ray source in a boron rich glass capillary.

In addition, the analysis parameters were as follows: the integration 2-theta range was 2-60 degrees; the integration chi range was 0-360 degrees; the number of chi segments was 1; the step size used was 0.02; the integration utility was cylint; normalization was used; dark counts were 8; omega offset was 180; and chi and phi offsets were 0.

PXRD diffractograms were also acquired via the Bruker AXS D8 Discover X-ray Diffractometer. This instrument was equipped with GADDS™ (General Area Diffraction Detection System), a Bruker AXS HI-STAR Area Detector at a distance of 15.05 cm as per system calibration, a copper source ($Cu/K_\alpha$ 1.54056 angstroms), automated x-y-z stage, and 0.5 mm collimator. The sample was compacted into pellet form and mounted on the x-y-z stage. A diffractogram was acquired under ambient conditiona at a powder setting of 40 kV and 40 mA in reflection mode while the sampleremained stationary. The exposure time was varied and specified for each sample. The diffractogram obtained underwent a spatial remapping procedure to account for the geometrical pincushion distortion of the area detector then integrated along chi from −118.8 to −61.8 degrees and 2-theta 2.1-37 degrees at a step size of 0.02 degrees with normalization set to bin normalize.

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, preferably +/−0.05. The entire pattern or most of the pattern peaks may also shift by about +/−0.1 degree due to differences in calibration, settings, and other variations from instrument to instrument and from operator to operator. All reported PXRD peaks in the Figures, Examples, and elsewhere herein are reported with an error of about ±0.1 degrees 2-theta.

For PXRD data herein, including Tables and Figures, each composition of the present invention may be characterized by any one, any two, any three, any four, any five, any six, any seven, or any eight or more of the 2 theta angle peaks. Any one, two, three, four, five, or six DSC transitions can also be used to characterize the compositions of the present invention. The different combinations of the PXRD peaks and the DSC transitions can also be used to characterize the compositions.

Solubility Measurements Via Ultraviolet (UV) Absorption

A calibration curve was constructed by preparing known concentrations of API in absolute ethanol in volumetric flasks. At each concentration, 200 microliters of the solution was transferred into a 96-well clear bottom UV plate. The sample absorbance was measured at 280 nm (unless otherwise noted) in a UV spectrophotometer. It was found that the absorbance vs. concentration correlation was linear to at least 100 micrograms/mL.

To measure the API concentration in the sample, a small aliquot was taken and diluted (typically 2000-fold) with absolute ethanol in a volumetric flask to a final approximate concentration of less than 100 micrograms/mL. The absorbance at 280 nm (unless otherwise noted) is measured and the solubility is calculated based on the calibration curve. The solubility of several statin salts were measured using the above described technique at a temperature of 20-25 degrees C.

EXAMPLE 1

Pravastatin Calcium Salt

To a solution of pravastatin Na salt (1.470 g; 3.292 mmol) in water (15.0 mL) was added a solution of calcium acetate (268 mg; 1.70 mmol) also in water (5.0 mL). The resulting solution was concentrated (through evaporation of water via a stream of nitrogen gas) to about 15 mL and cooled to 0 degrees C. A white solid precipitated and was collected via filtration. The filtrate was cooled again to 0 degrees C. which yielded further precipitation. After filtration, the solids were combined and dried in a dessicator. The resultant solid was determined to be pravastatin calcium salt. The resultant salt was a 2:1 pravastatin to calcium salt.

FIG. 1 shows the PXRD diffractogram of the pravastatin calcium salt (Bruker, data as collected). The pravastatin calcium salt can be characterized by any one, any two, any three, or any four or more of the PXRD peaks in FIG. 1. Based on the PXRD diffractogram, the pravastatin calcium salt appears to be weakly crystalline.

Figure 2:
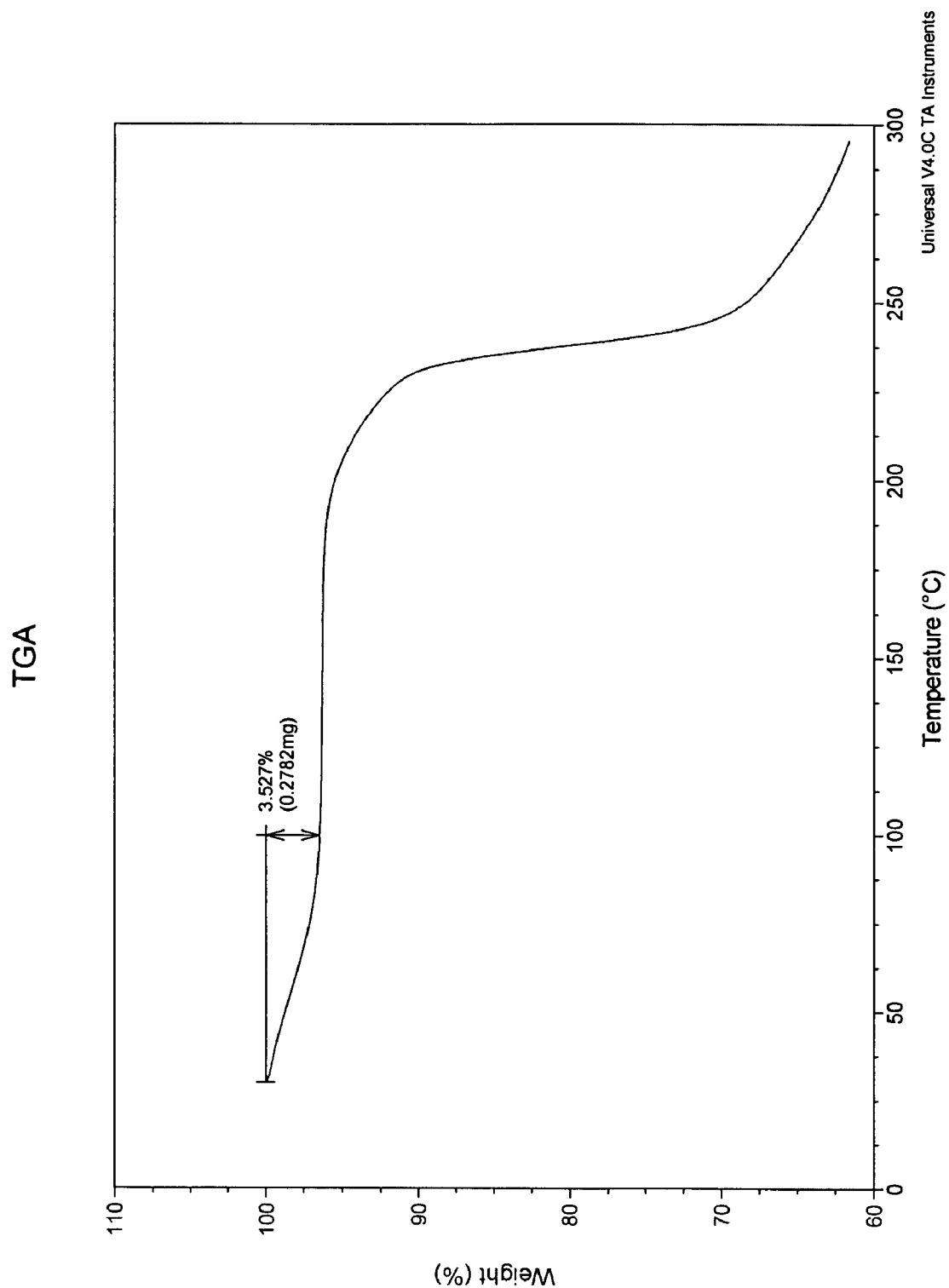
FIG. 2 shows a TGA thermogram of a pravastatin calcium salt.

TGA of the pravastatin calcium salt showed about a 3.5 percent weight loss between about 25 degrees C. and 100 degrees C. (See FIG. 2).

IR spectroscopy was also used to characterize the pravastatin calcium salt. The pravastatin calcium salt can be characterized by any one, any two, any three, any four, any five, or any six or more of the IR peaks in FIG. 3 including, but not limited to, 2360, 1728, 1561, 1444, 1186, 855, and 668 cm$^{-1}$.

Figure 4:
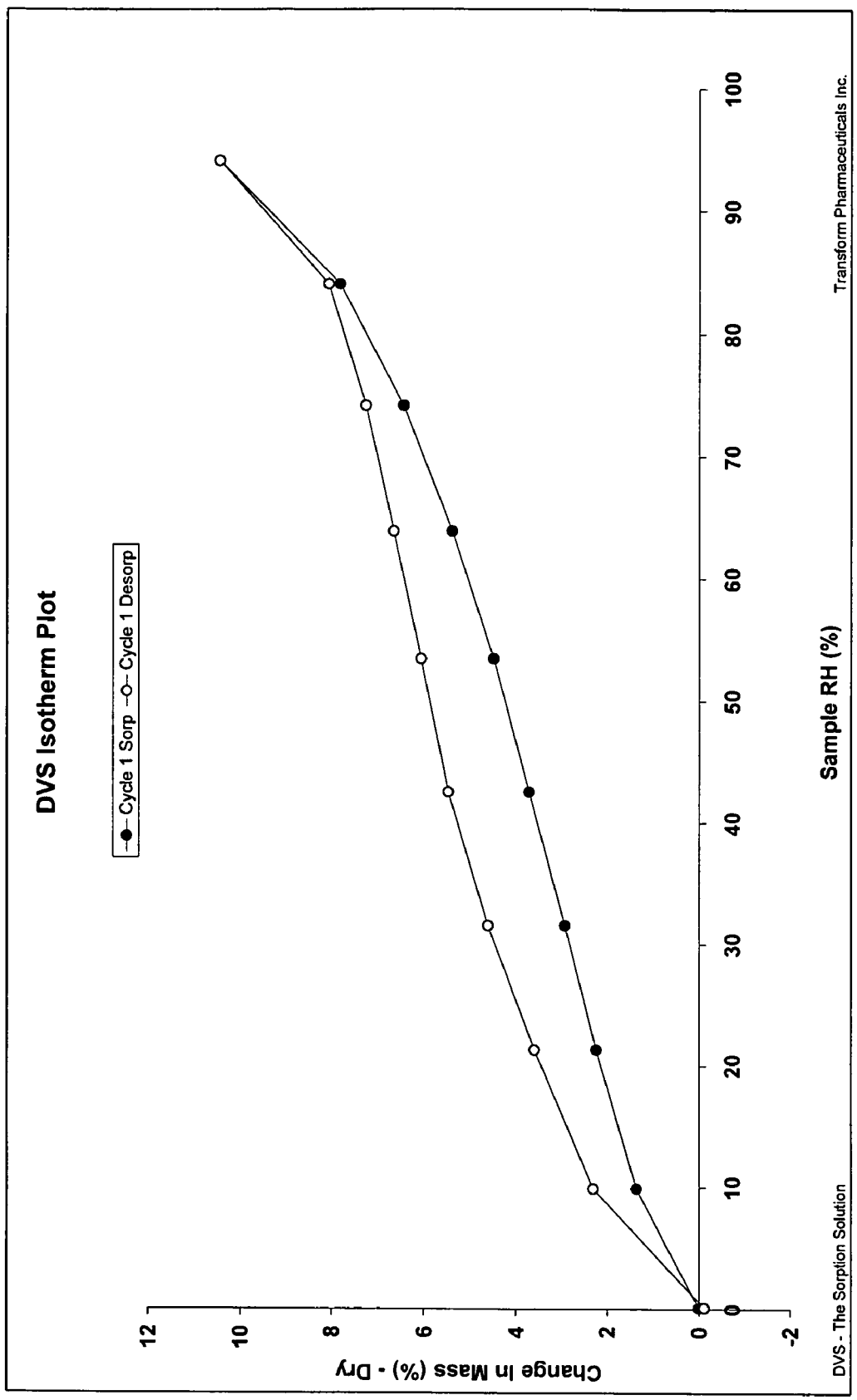
FIG. 4 shows a DVS moisture sorption isotherm plot of a pravastatin calcium salt.
Figure 5:
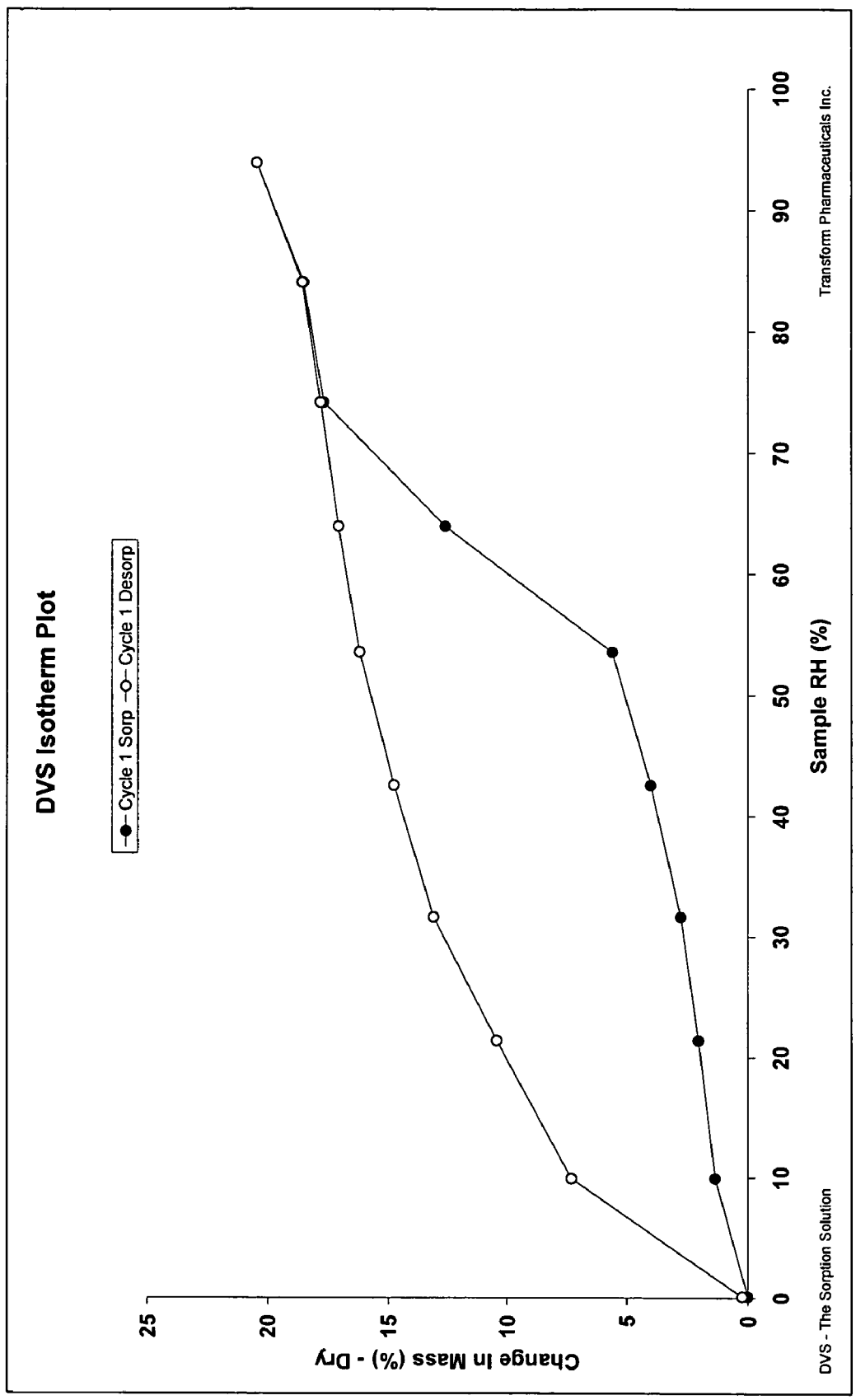
FIG. 5 shows a DVS moisture sorption isotherm plot of a pravastatin sodium salt.

Dynamic Vapor Sorption (DVS) data were also acquired on both the pravastatin calcium salt and the pravastatin sodium salt. FIG. 4 shows a moisture sorp-desorp cycle of the pravastatin calcium salt. The calcium salt showed continuous water adsorption as a function of relative humidity (RH) up to about 11 percent mass gain. This is consistent with an amorphous compound. Hysteresis is observed in the desorption cycle. FIG. 5 shows a moisture sorp-desorp cycle of the pravastatin sodium salt. The sodium salt, a crystalline salt, showed a gradual increase in mass with humidity up to about 54 percent RH. Above 54 percent RH, adsorbed water increased significantly. Significant hysteresis is observed in the desorption cycle. The pravastatin sodium salt showed a greater hygroscopicity than the calcium salt.

Another method was also used to prepare pravastatin calcium salt. To a solution of pravastatin Na salt (496 mg; 1.11 mmol) in water (5.0 mL) was added a solution of calcium chloride (69 mg; 0.62 mmol) also in water (2.0 mL). The resulting solution was evaporated yielding a white solid. Pravastatin Ca salt was extracted from the solid with dry ethanol (10.0 mL) and filtered. The solution was evaporated yielding an oil which was triturated using diethyl ether (10.0 mL). The powdery white solid (100 mg) was washed with cold water (5.0 mL) and air-dried. The resultant solid was determined to be pravastatin calcium salt.

The aqueous solubility of the calcium salt of pravastatin was determined to be about 17-20 mg/mL (via UV detection, 20-25 degrees C.). The aqueous solubility of the sodium salt of pravastatin was measured to be greater than 300 mg/mL.

EXAMPLE 2

26 Week Stability Data of Pravastatin Salts in E463808

Several salts of pravastatin were suspended in E463808 omega-3 oil and placed in either capped glass vials or sealed gelatin capsules. Gelcaps were used at 25 degrees C. while glass vials were used at 25, 40, and 60 degrees C. The suspensions of salt in oil were measured periodically for 26 weeks. HPLC was used to measure degradation of the pravastatin salts.

Figure 6:
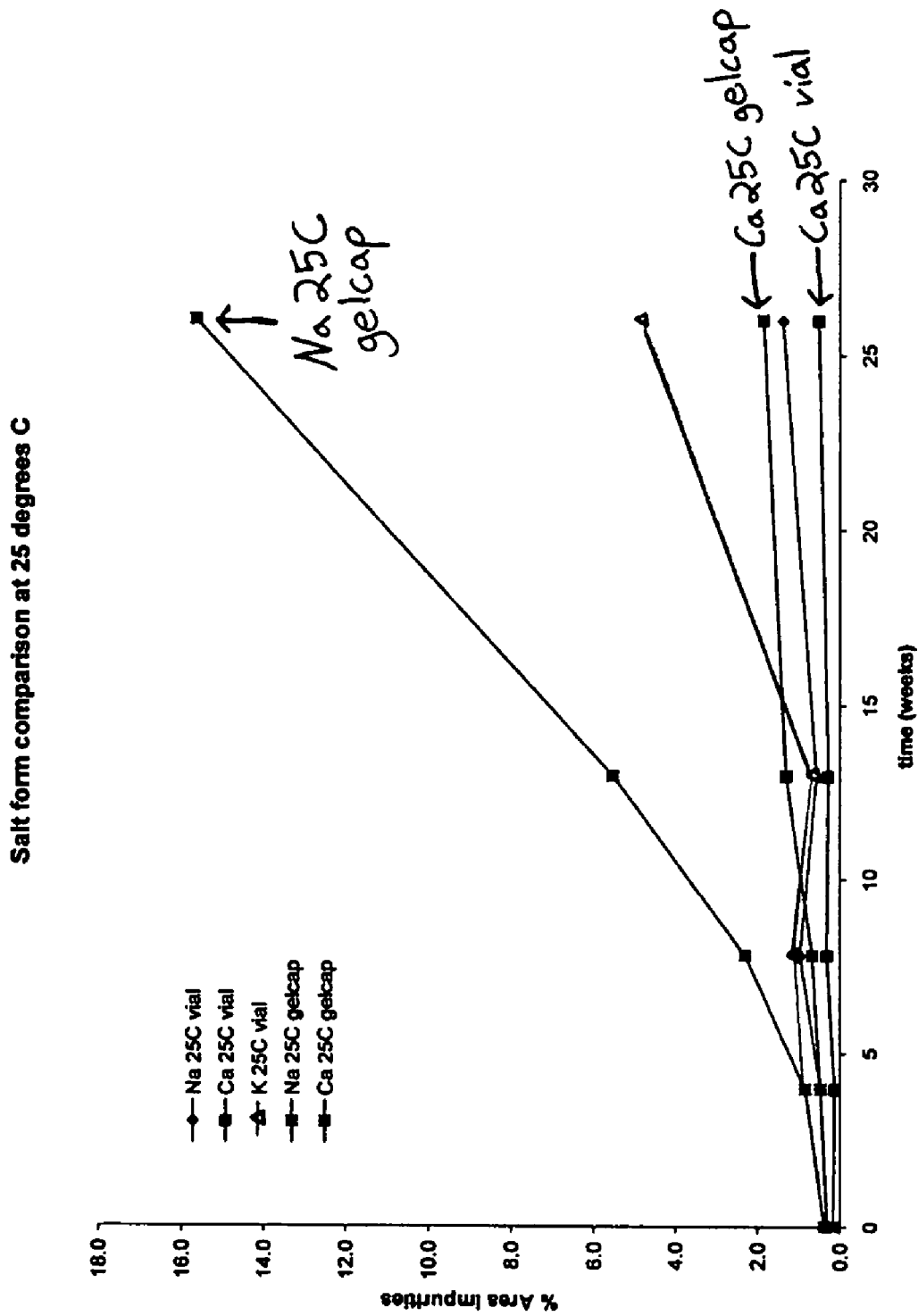
FIG. 6 shows a plot of the percent impurities from several pravastatin salts at 25 degrees C. over a period of 26 weeks in vials and gelcaps.

FIG. 6 shows the stability data of both vials and gelatin capsules (gelcaps) at 25 degrees C. The calcium salt of pravastatin showed a significantly smaller percentage of impurities over time than that of either the sodium salt in a gelcap or the potassium salt in a vial. The calcium salt in a vial was shown to degrade the least of all salts in either a gelcap or a vial over a period of 26 weeks at 25 degrees C.

Figure 7:
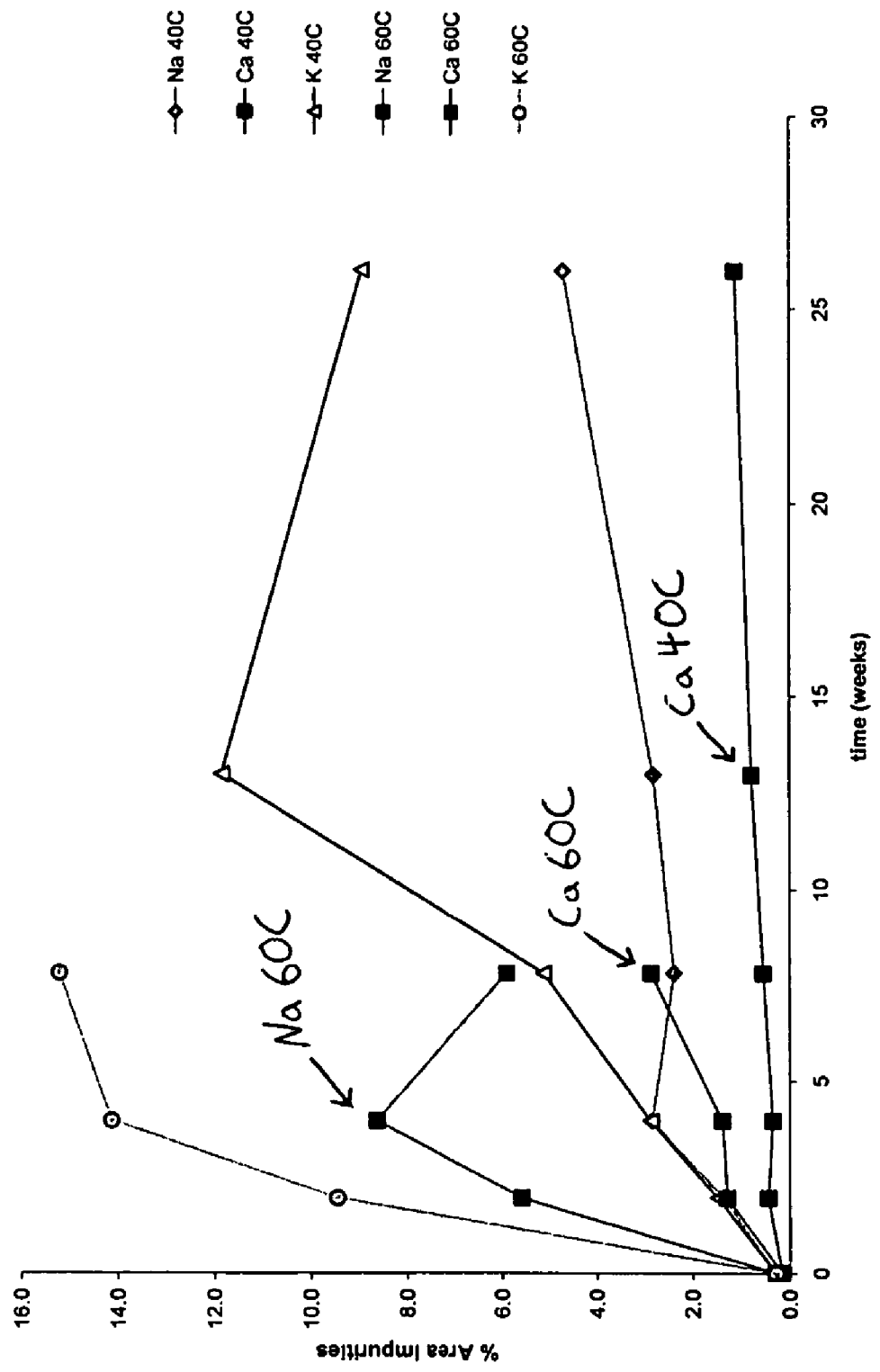
FIG. 7 shows a plot of the percent impurities from several pravastatin salts at 40 and 60 degrees C. over a period of up to 26 weeks.

FIG. 7 shows the stability of pravastatin salts in capped glass vials at 40 and 60 degrees C. Again, the calcium salt was shown to degrade substantially less than either the sodium or the potassium salt at a given temperature. Surprisingly, the calcium sample at 60 degrees C. showed significantly less degradation than the potassium salt at 40 degrees C. and was similar to the sodium salt at 40 degrees C. over a period of 8 weeks.

EXAMPLE 3

Fluvastatin Calcium Salt 505.9 mg (1.167 mmol) of fluvastatin Na salt was dissolved in 15 mL of water. 94.2 mg (0.595 mmol) of calcium acetate was dissolved in 2 mL of water. A precipitate formed immediately with the addition of the calcium acetate solution to the fluvastatin Na solution. Solids were collected by filtration and dried first in a vacuum oven at 65 degrees C. for 0.5 hours and left at room temperature under nitrogen flow overnight. Dried solids were lightly ground in a mortar and pestle before characterization. The resultant solid was characterized using PXRD, DSC, TGA, Raman, and IR spectroscopy and determined to be a calcium salt of fluvastatin. The resultant salt was a 2:1 fluvastatin to calcium salt.

Solubility measurements of the sodium salt and of the calcium salt of fluvastatin were acquired in water at 23 degrees C. Solubility was measured gravimetrically in deionized water. 5.5 mg of fluvastatin sodium salt was dissolved in about 130 to 150 microliters of water, which yielded an aqueous solubility of the sodium salt of about 37 to 42 mg/mL. 5.5 mg of the calcium salt did not completely dissolve in water, even after adding up to 20 mL of water. Aqueous solubility of the calcium salt was determined to be less than or equal to about 0.275 mg/mL.

Figure 8:
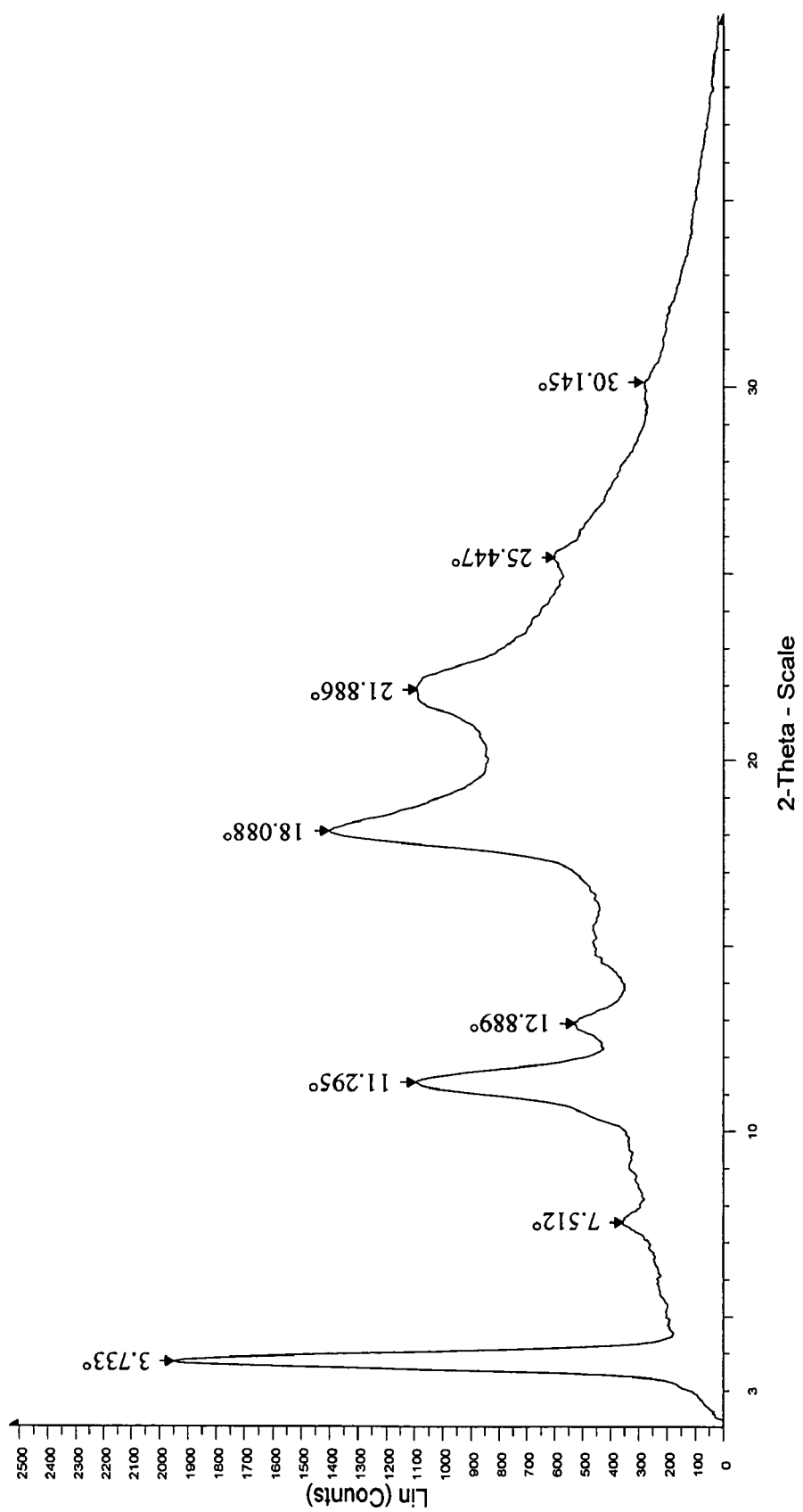
FIG. 8 shows a PXRD diffractogram of a fluvastatin calcium salt.

The fluvastatin calcium salt can be characterized by any one, any two, any three, any four, any five, or any six or more of the PXRD peaks in FIG. 8 including, but not limited to, 3.7, 7.5, 11.3, 12.9, 18.1, 21.9, and 25.4 degrees 2-theta (Rigaku, data as collected). Based on the PXRD diffractogram, the fluvastatin calcium salt appears to be weakly crystalline.

Figure 9:
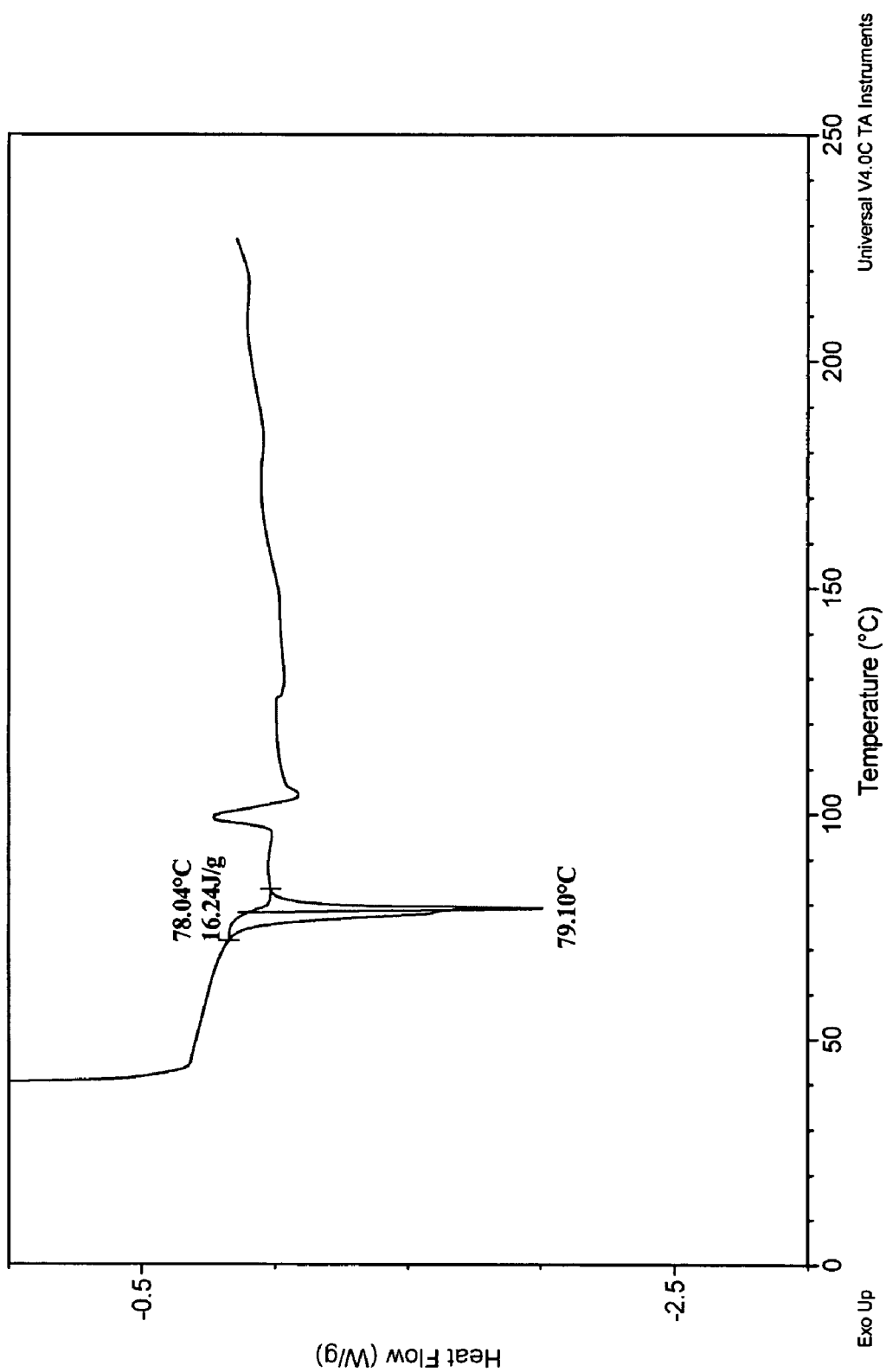
FIG. 9 shows a DSC thermogram of a fluvastatin calcium salt.

DSC was run from 25 degrees C. to 230 degrees C. at 10 degrees C./minute. DSC showed an endothermic transition at about 79 degrees C. (See FIG. 9). Note, the exotherm and small endotherm around 100 degrees C. is an artifact of the instrument and not related to the sample.

Figure 10:
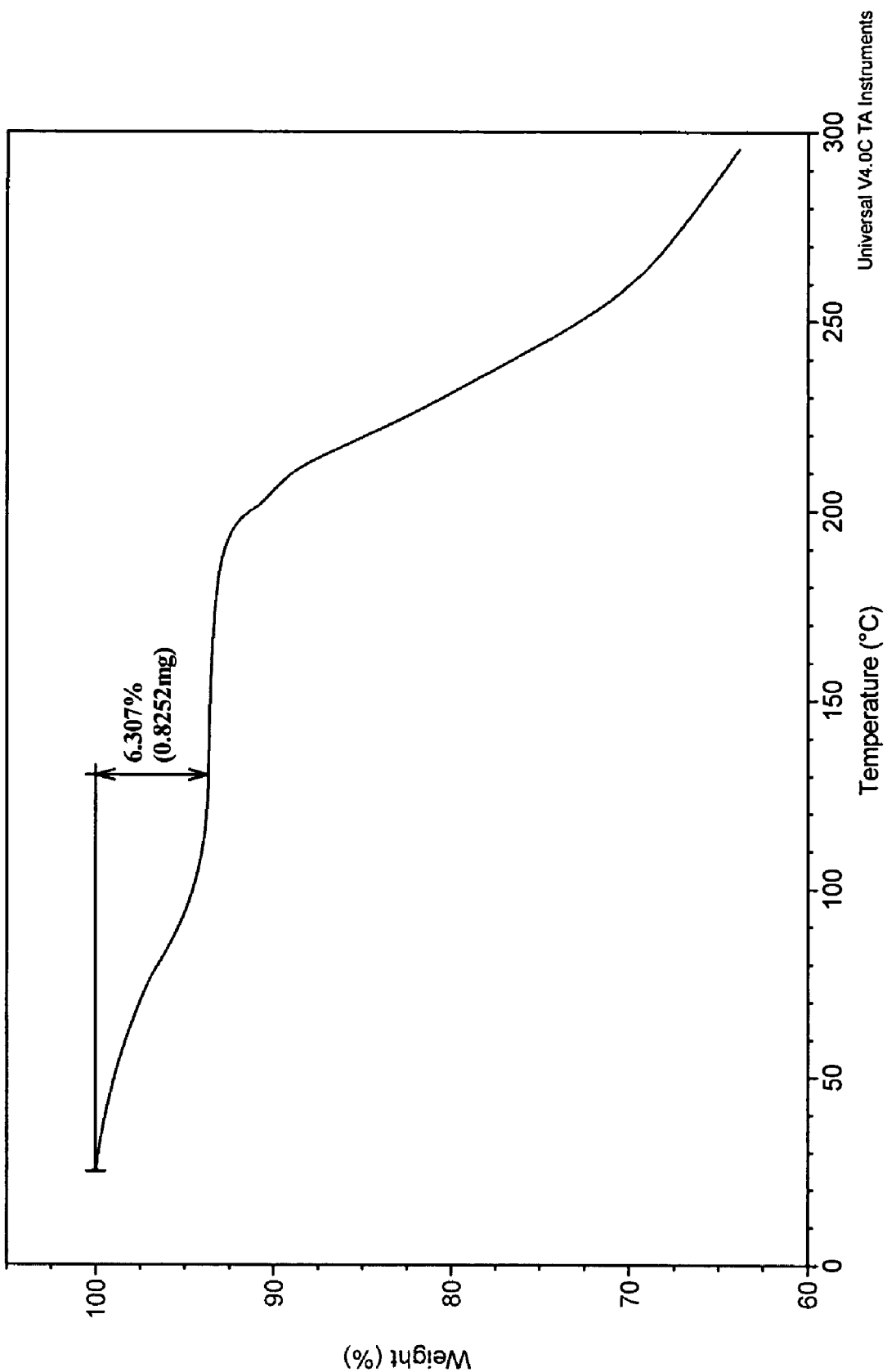
FIG. 10 shows a TGA thermogram of a fluvastatin calcium salt.

TGA (13.083 mg) was run from 25 degrees C. to 300 degrees C. at 10 degrees C./minute. TGA showed a 6.3 percent weight loss between 25 degrees C. and 130 degrees C., which may correspond to about 1.5 equivalents of water (See FIG. 10).

Figure 11:
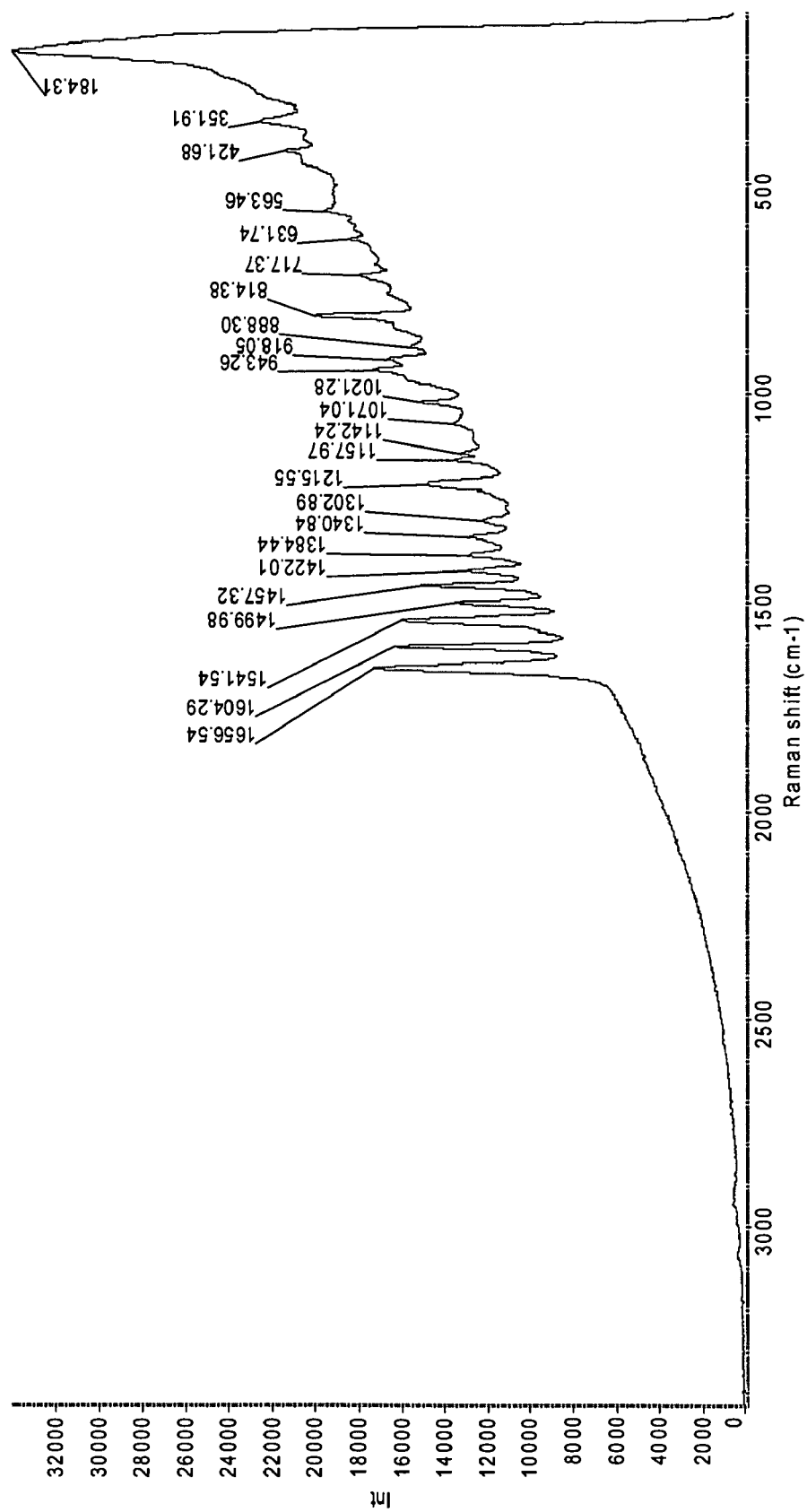
FIG. 11 shows a Raman spectrum of a fluvastatin calcium salt.

Raman spectroscopy was also used to characterize the fluvastatin calcium salt. The fluvastatin calcium salt can be characterized by any one, any two, any three, any four, any five, or any six or more of the Raman shifts in FIG. 11 including, but not limited to, 1657, 1604, 1542, 1500, 1457, 1216, 814, and 352 cm$^{-1}$.

Figure 12:
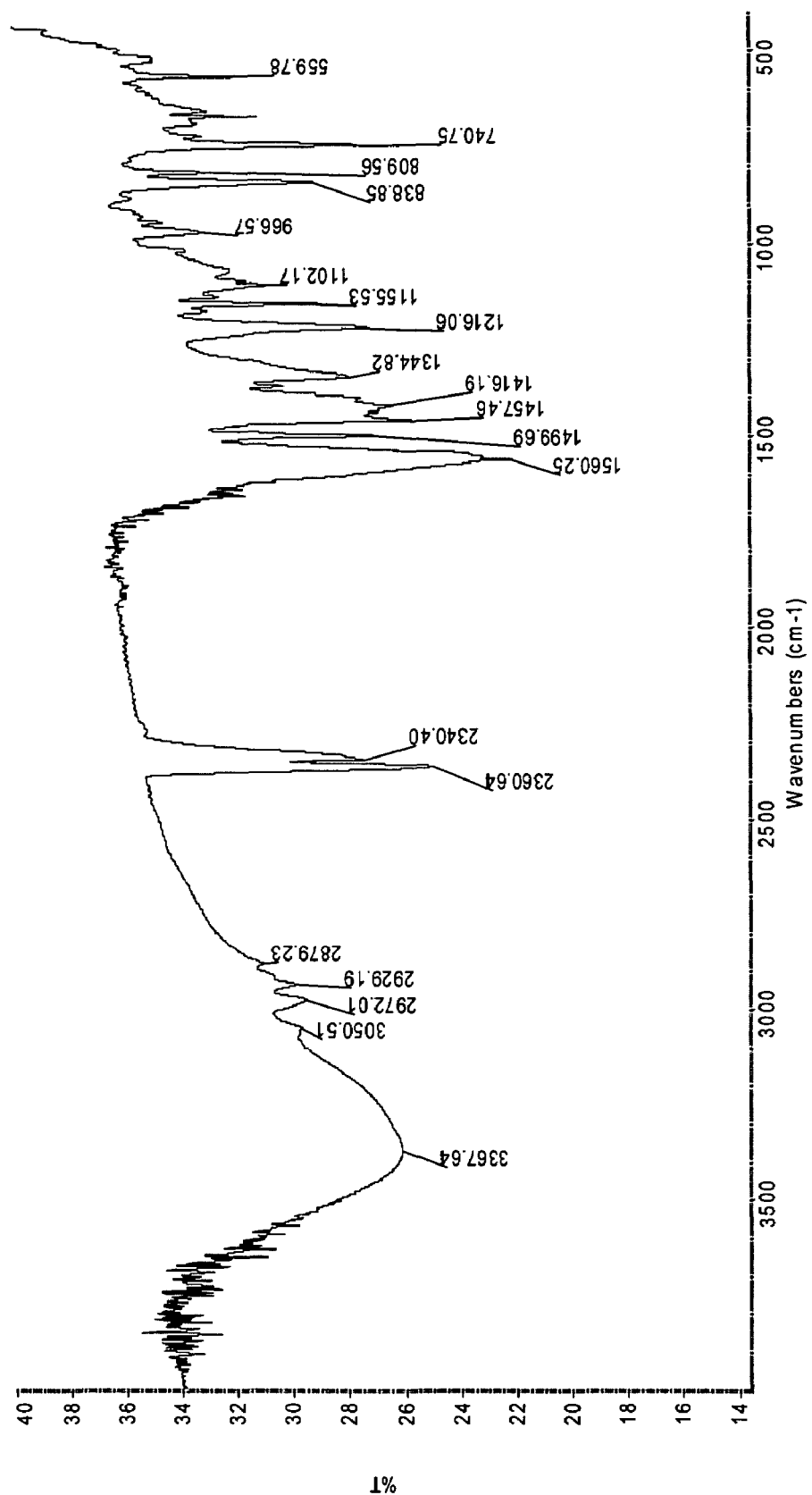
FIG. 12 shows an IR spectrum of a fluvastatin calcium salt.

IR spectroscopy was also used to characterize the fluvastatin calcium salt. The fluvastatin calcium salt can be characterized by any one, any two, any three, any four, any five, or any six or more of the IR peaks in FIG. 12 including, but not limited to, 2361, 1560, 1500, 1457, 1345, 1216, 1155, 839, 741, and 560 cm$^{-1}$.

EXAMPLE 4

Pharmacokinetic Study of Pravastatin Calcium Salt in Dogs

A two-way cross-over experiment was completed with six fasted beagle dogs to compare the pharmacokinetic parameters of pravastatin calcium salt with pravastatin sodium salt. The pravastatin sodium salt was acquired from PRAVACHOL® tablets. The pravastatin calcium salt was acquired via the method described in Example 1. The pravastatin calcium salt dosage form administered to the dogs consisted of 11.0 mg pravastatin calcium salt (equivalent to 10 mg pravastatin acid) and 744 mg Ropufa 75 ethyl esters of omega-3 fatty acids in a soft gelatin capsule shell. In vitro release testing of the capsules was completed and showed complete dissolution in deionized water at 37 degrees C. The mean dose of pravastatin free acid administered as PRAVACHOL® was 0.85 mg/kg and the mean dose of pravastatin free acid administered as pravastatin calcium salt was 0.95 mg/kg. Following administration, plasma samples were collected pre-dose and then at 0.25, 0.5, 1, 1.5, 2, 3, 4, 6, 8, 12, and 24 hours post-dose. Plasma samples were analyzed for pravastatin concentration using an LC/MS method. Table 2 shows several important pharmacokinetic parameters of pravastatin from both oral formulations dosed to six fasted beagle dogs.

TABLE 2

Pharmacokinetic parameters of pravastatin from two oral formulations dosed to six fasted beagle dogs in a two-way cross-over study.

| Animal | $AUC_{0-t}$ (ng/mL × hr) | $AUC_{inf}$ (ng/mL × hr) | $C_{max}$ (ng/mL) | $T_{max}$ (hr) | $t_{1/2}$ (hr) | Relative Bioavailability[a] |
|---|---|---|---|---|---|---|
| | | Pravastatin Calcium Salt | | | | |
| 1001 | 512.94 | 518.11 | 99.0 | 1 | 3.44 | 134 |
| 1002 | 264.11 | 268.01 | 87.2 | 0.5 | 1.85 | 62.1 |
| 1003 | 488.36 | 494.27 | 182 | 1 | 1.67 | 74.9 |
| 2001 | 438.55 | 453.69 | 131 | 0.5 | 2.5 | 99.7 |
| 2002 | 505.30 | 515.14 | 166 | 0.25 | 1.89 | 148 |
| 2003 | 380.68 | 396.20 | 182 | 1 | 2.76 | 200 |
| Mean | 431.66 | 440.90 | 141.20 | 0.71 | 2.35 | 121 |
| SD | 95.879 | 96.306 | 41.822 | 0.332 | 0.679 | 54.0 |
| % CV | 22.2 | 21.8 | 29.6 | 46.9 | 28.9 | 44.6 |
| | | PRAVACHOL ® | | | | |
| 1001 | 333.39 | 345.11 | 94.0 | 0.5 | 2.44 | N/A |
| 1002 | 375.46 | 378.47 | 117 | 1 | 1.69 | N/A |
| 1003 | 575.07 | 581.85 | 192 | 1 | 1.79 | N/A |
| 2001 | 350.84 | 414.58 | 40.2 | 1 | 10.18 | N/A |
| 2002 | 297.63 | 312.21 | 129 | 1 | 2.59 | N/A |
| 2003 | 165.66 | 171.78 | 33.6 | 0.5 | 2.06 | N/A |
| Mean | 349.68 | 367.33 | 100.97 | 0.83 | 3.46 | — |
| SD | 132.89 | 134.27 | 59.345 | 0.26 | 3.31 | — |
| % CV | 38.0 | 36.6 | 58.8 | 31.0 | 95.8 | — |

[a]Bioavailability calculated relative to PRAVACHOL ® $AUC_{inf}$ values were normalized for the doses received by each animal In general, AUC and $C_{max}$ values were slightly higher for pravastatin calcium salt compared with the values from the PRAVACHOL® tablet. $T_{max}$ values are comparable between the formulations. As a result, the relative bioavailability of pravastatin following administration of pravastatin calcium salt (normalized for the doses administered) appears to be slightly higher than that of PRAVACHOL®. These results suggest that the suspension of pravastatin calcium salt in pharmaceutical omega-3 ethyl esters does not significantly influence the pharmacokinetic behavior of pravastatin.

EXAMPLE 5

Pravastatin Magnesium Salt

To 3 mL of a 30.5 mass percent pravastatin sodium solution was added 0.7 mL of a 49.5 mass percent magnesium chloride solution. The solvent for both solutions was deionized water. Phase separation of the two liquids was observed within 30 minutes. Crystallization from the dense phase occurred overnight. Two solid phases (crystal habits) were collected: (A) a "fluffy" suspended phase at the top of the reaction vessel and (B) a dense solid phase at the bottom of the reaction vessel. The resultant salt was a 2:1 pravastatin to magnesium salt.

Figure 13:
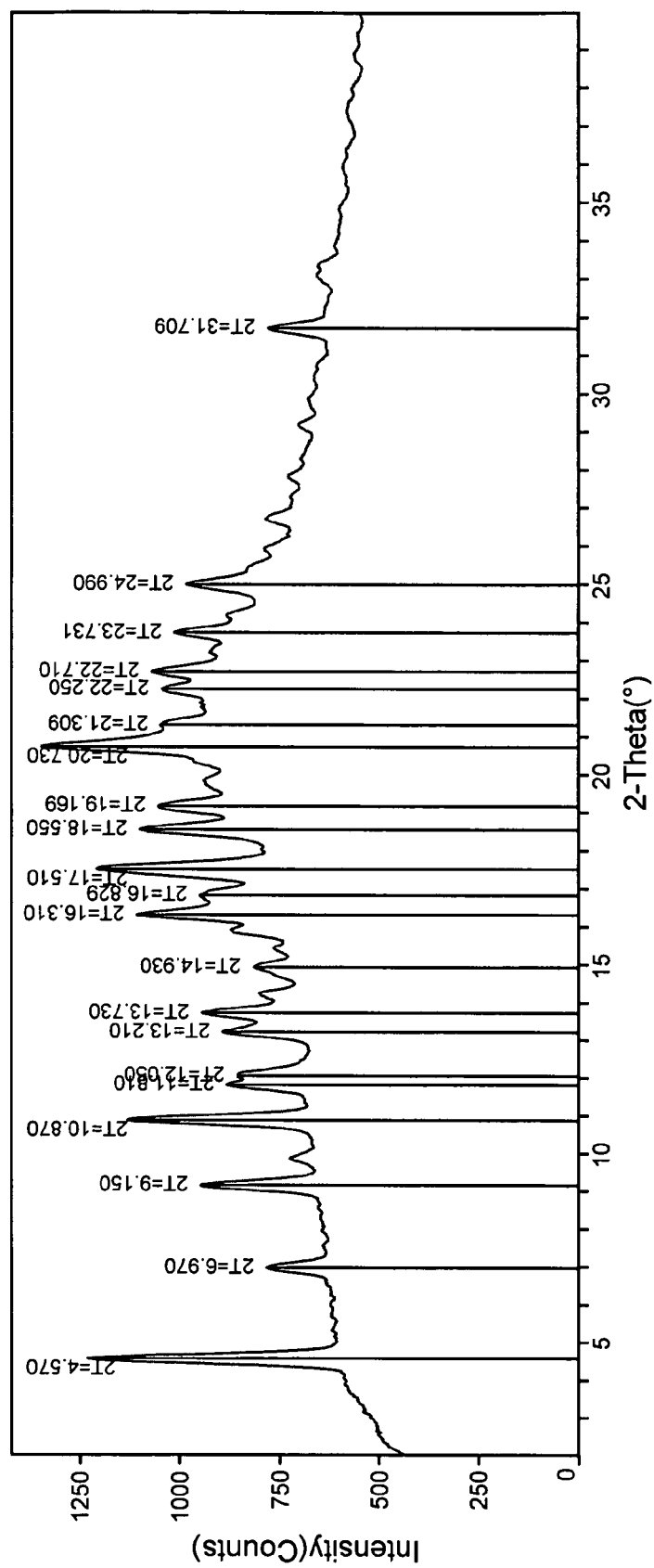
FIG. 13 shows a PXRD diffractogram of a pravastatin magnesium salt (habit A).

The pravastatin magnesium salt (habit A) can be characterized by any one, any two, any three, any four, any five, or any six or more of the PXRD peaks in FIG. 13 including, but not limited to, 4.57, 6.97, 9.15, 10.87, 11.81, 13.21, 13.73, 16.31, 17.51, 18.55, 19.17, 20.73, 22.71, 23.73, and 24.99 degrees 2-theta (Rigaku, data as collected). The peak observed at 31.709 degrees 2-theta corresponds to sodium chloride impurity.

Figure 14:
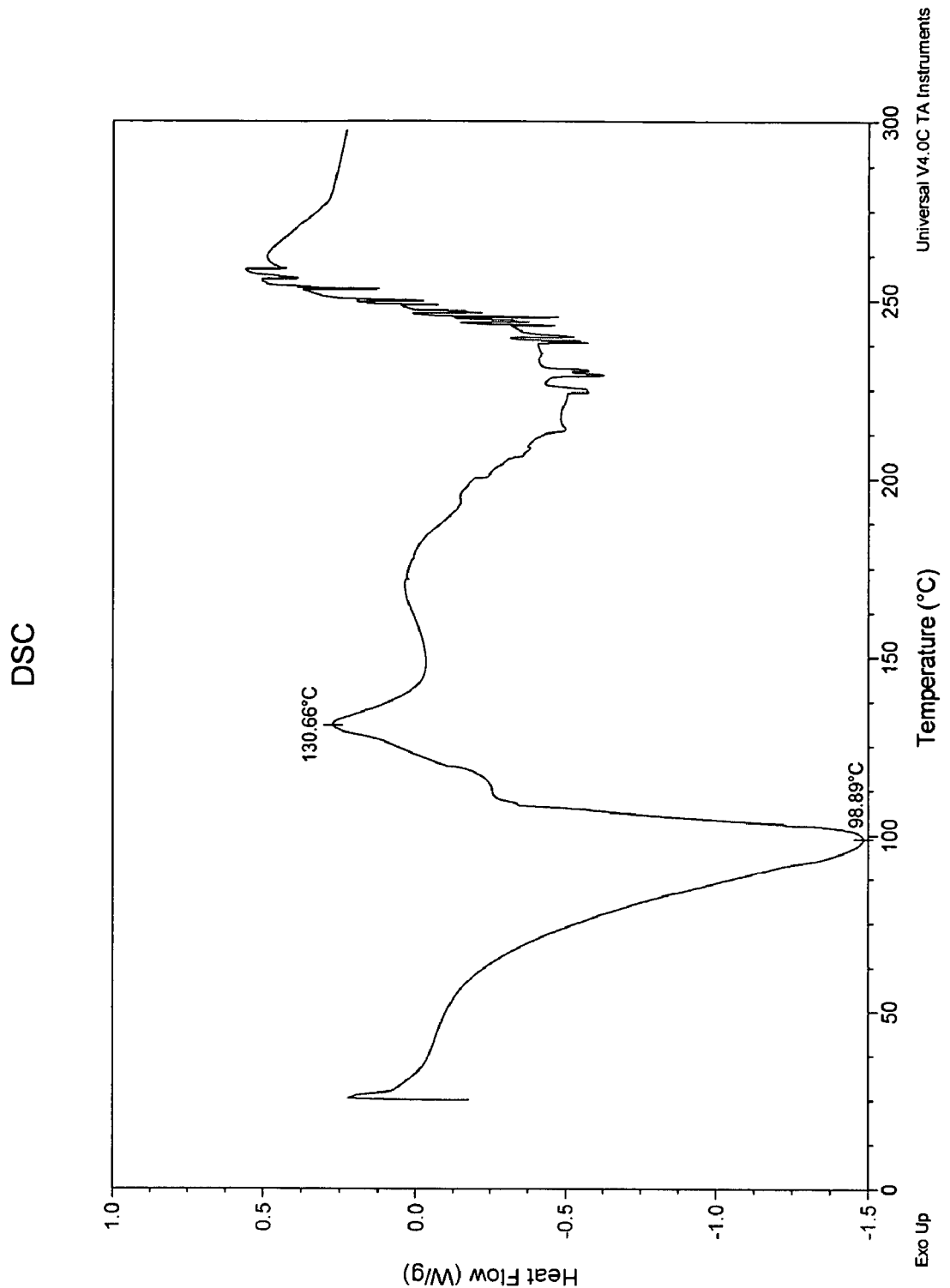
FIG. 14 shows a DSC thermogram of a pravastatin magnesium salt (habit A).

DSC was run (on pravastatin magnesium salt habit A) from 25 degrees C. to 300 degrees C. at 10 degrees C./minute. DSC showed an endothermic transition at about 99 degrees C. (See FIG. 14). The exotherm at about 131 degrees C. may represent a recrystallization event.

Figure 15:
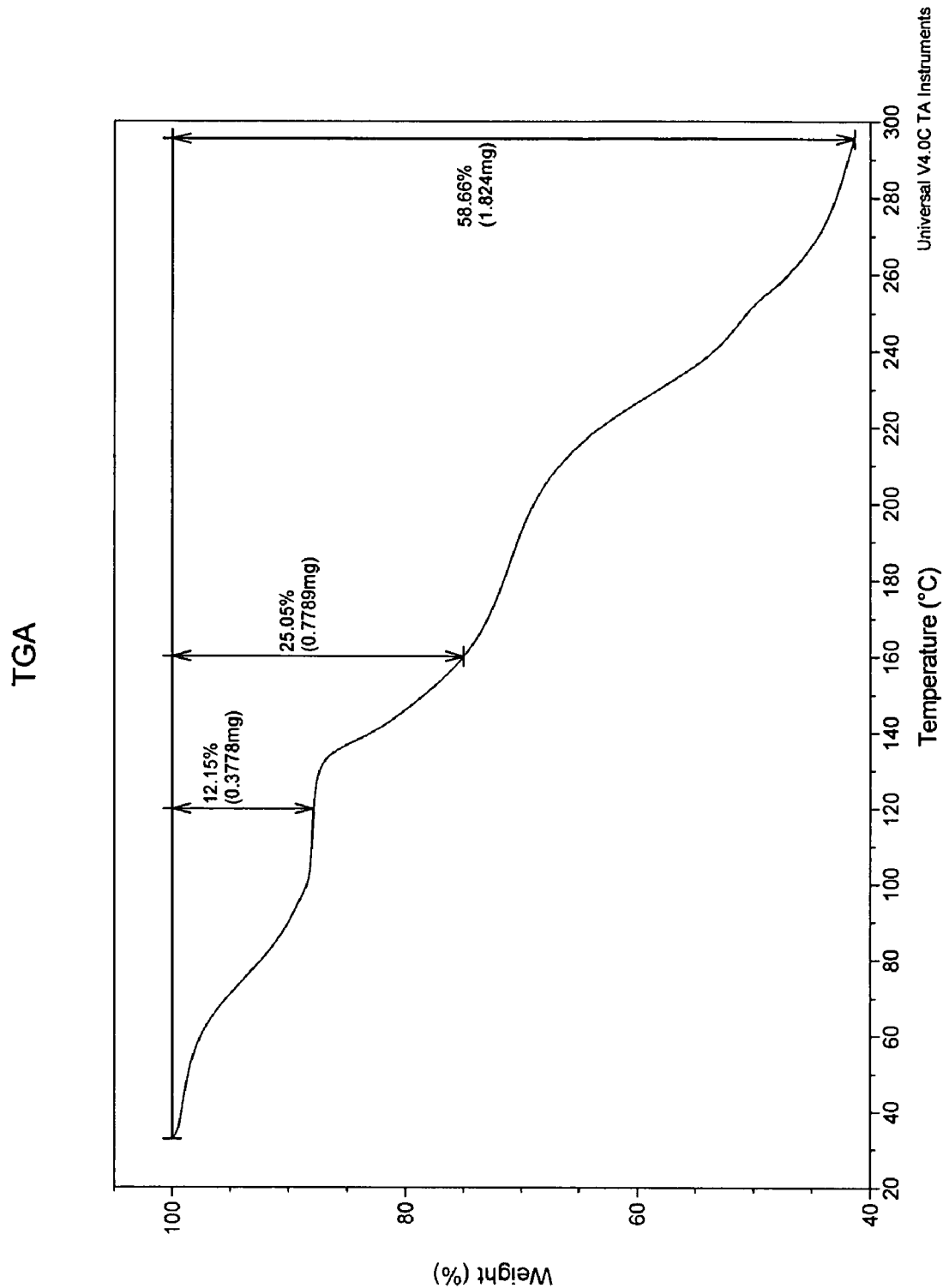
FIG. 15 shows a TGA thermogram of a pravastatin magnesium salt (habit A).

TGA was run (on pravastatin magnesium salt habit A) from 25 degrees C. to 300 degrees C. at 10 degrees C./minute. TGA showed about a 12 percent weight loss between 25 degrees C. and about 120 degrees C., and about a 25 percent weight loss between 25 degrees C. and about 160 degrees C. (See FIG. 15).

Figure 16:
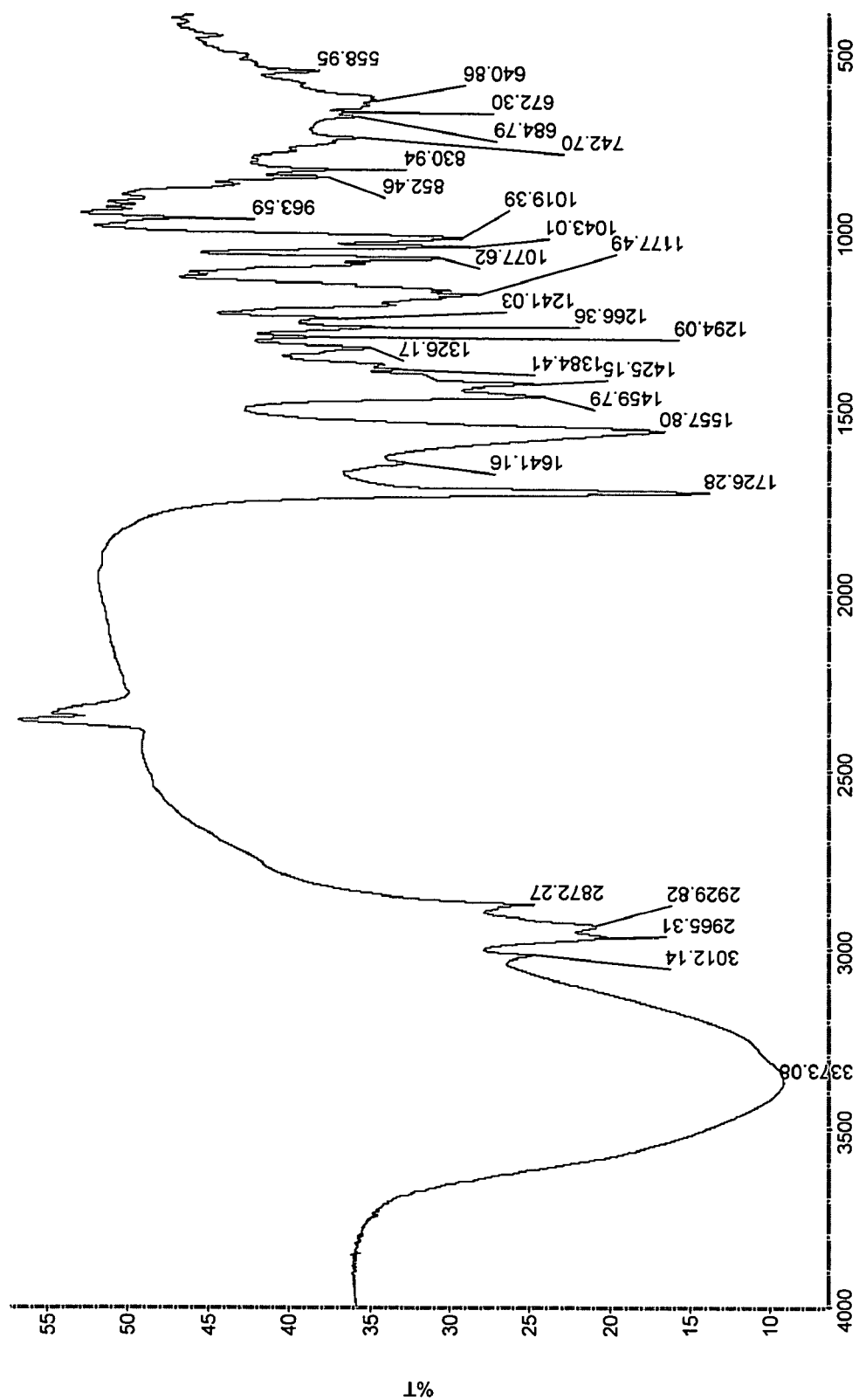
FIG. 16 shows an IR spectrum of a pravastatin magnesium salt (habit A).

IR spectroscopy was also used to characterize the pravastatin magnesium salt (habit A). The salt can be characterized by any one, any two, any three, any four, any five, or any six or more of the IR peaks in FIG. 16 including, but not limited to, 1726, 1557, 1425, 1177, 1078, 1019, and 641 $cm^{-1}$. The IR spectrum was acquired in transmission mode with the sample pressed into a KBr pellet. The spectrum is baseline corrected.

Figure 17:
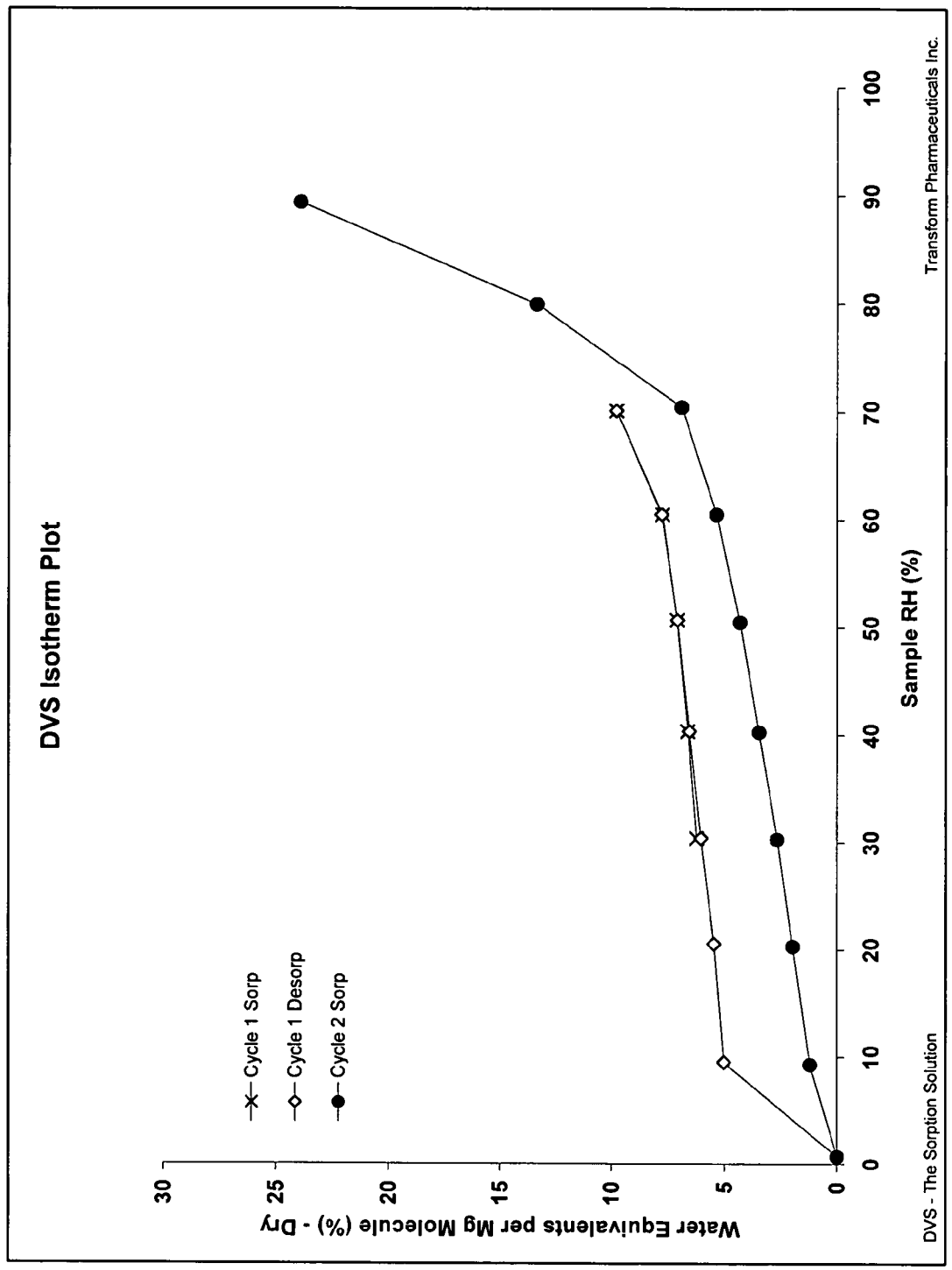
FIG. 17 shows a DVS moisture sorption isotherm plot of a pravastatin magnesium salt (habit A).

FIG. 17 shows a dynamic vapor sorption (DVS) isotherm plot of the pravastatin magnesium salt (habit A). This was completed at 25 degrees C. and the data show a stable region between about 10 and about 60 percent relative humidity (RH).

The solubility of pravastatin magnesium salt (habit A) in water was measured (via UV detection) to be 14.22 mg/mL.

Figure 18:
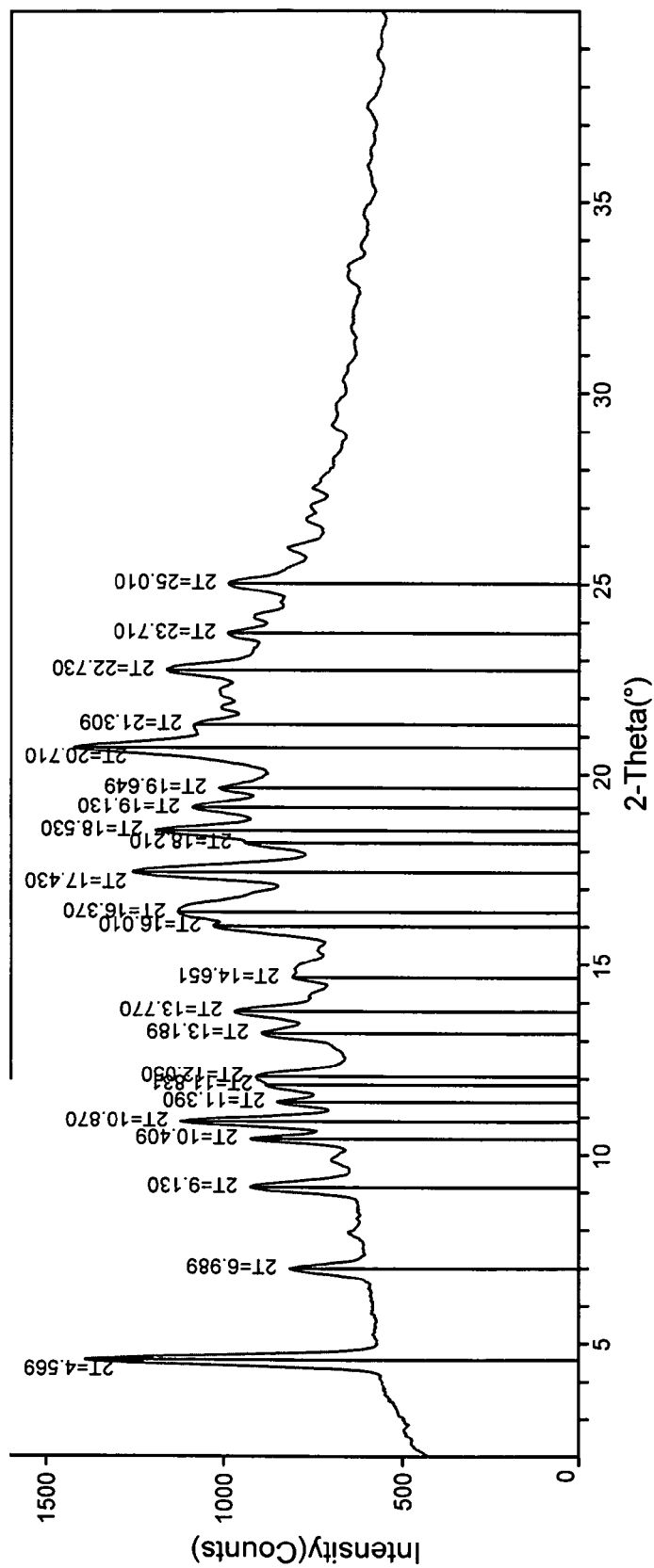
FIG. 18 shows a PXRD diffractogram of a pravastatin magnesium salt (habit B).

The pravastatin magnesium salt (habit B) can be characterized by any one, any two, any three, any four, any five, or any six or more of the PXRD peaks in FIG. 18 including, but not limited to, 4.57, 6.99, 9.13, 10.41, 10.87, 12.05, 13.19, 13.77, 16.37, 17.43, 18.53, 19.13, 20.71, 22.73, and 25.01 degrees 2-theta (Rigaku, data as collected).

Figure 19:
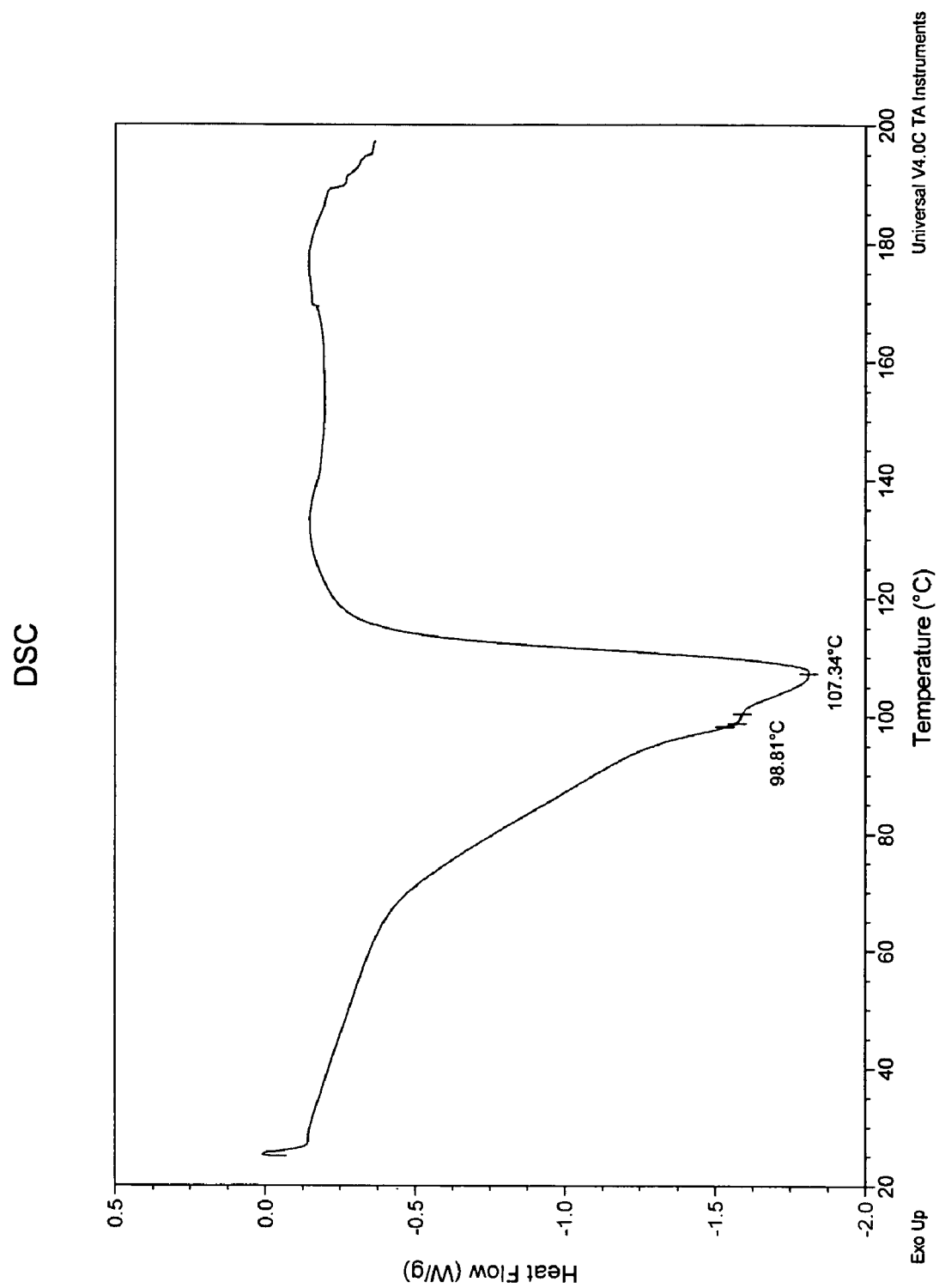
FIG. 19 shows a DSC thermogram of a pravastatin magnesium salt (habit B).

DSC was run (on pravastatin magnesium salt habit B) from 25 degrees C. to 200 degrees C. at 10 degrees C./minute. DSC showed an endothermic transition at about 107 degrees C. (See FIG. 19).

Figure 20:
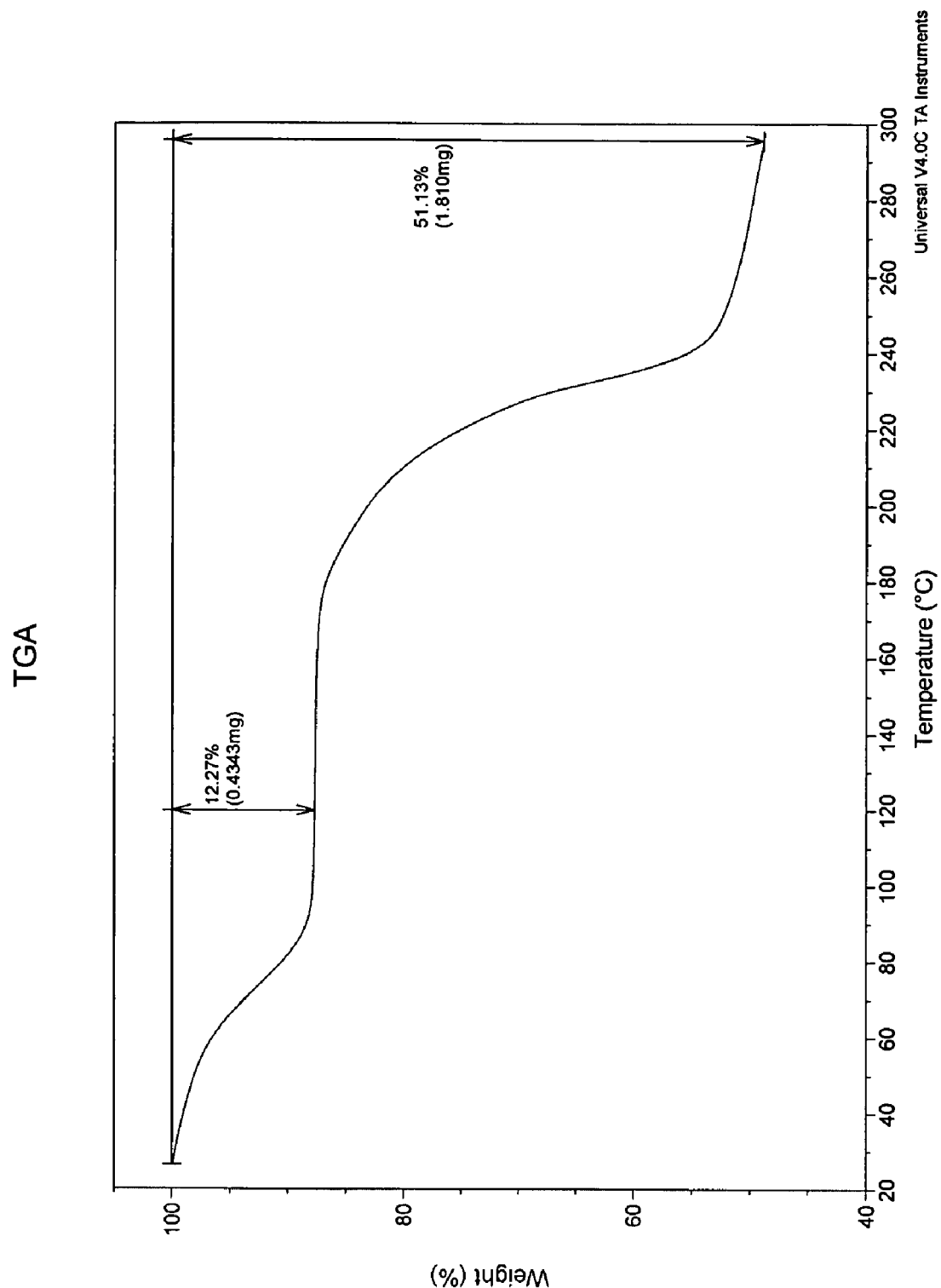
FIG. 20 shows a TGA thermogram of a pravastatin magnesium salt (habit B).

TGA was run (on pravastatin magnesium salt habit B) from 25 degrees C. to 300 degrees C. at 10 degrees C./minute. TGA showed about a 12 percent weight loss between 25 degrees C. and about 120 degrees C. (See FIG. 20).

Figure 21:
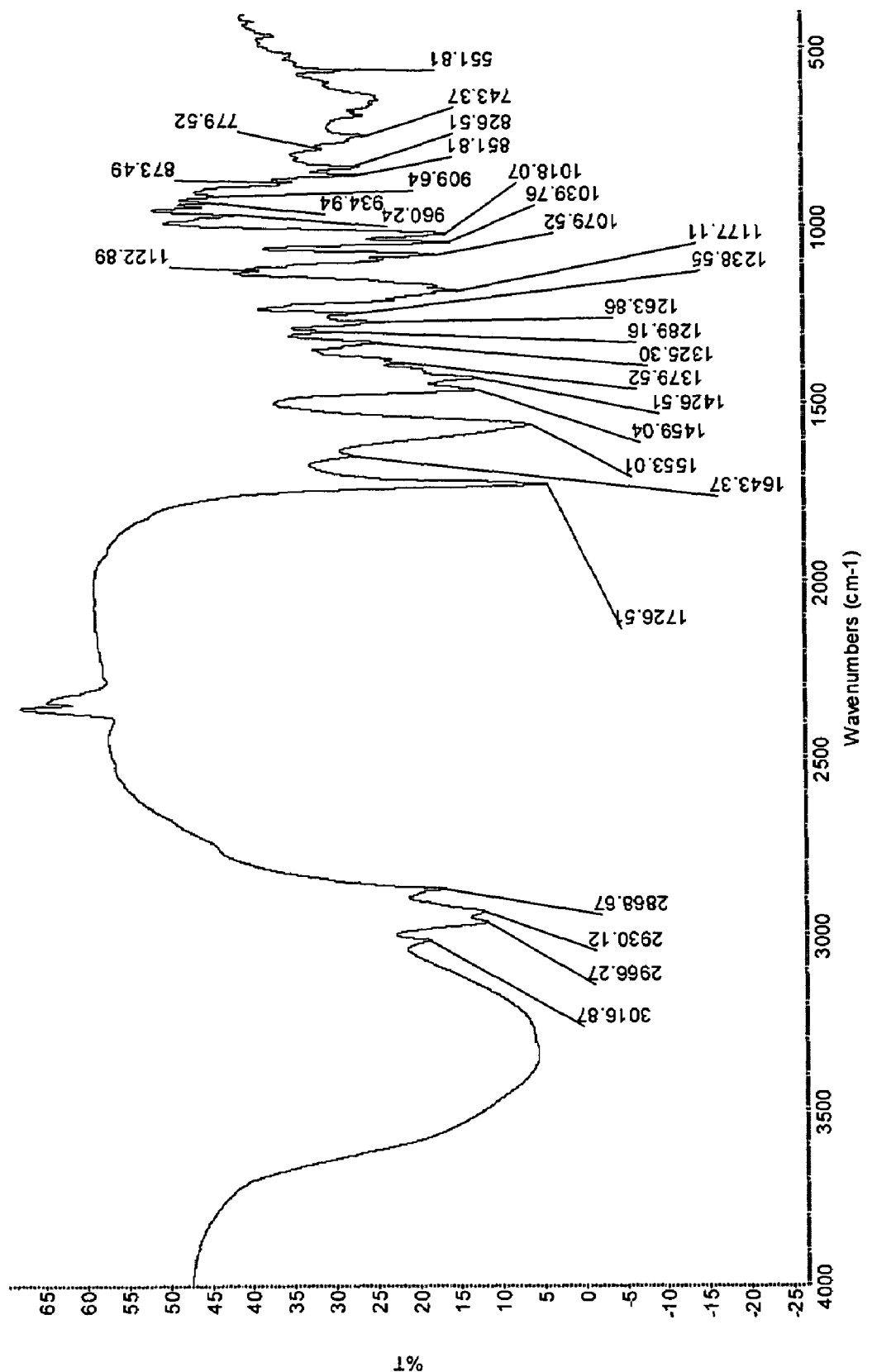
FIG. 21 shows an IR spectrum of a pravastatin magnesium salt (habit B).

IR spectroscopy was also used to characterize the pravastatin magnesium salt (habit B). The salt can be characterized by any one, any two, any three, any four, any five, or any six or more of the IR peaks in FIG. 21 including, but not limited to, 1726, 1553, 1459, 1426, 1177, 1079, 1039, and 827 cm$^{-1}$. The IR spectrum was acquired in transmission mode with the sample pressed into a KBr pellet. The spectrum is baseline corrected.

The solubility of pravastatin magnesium salt (habit B) in water was measured (via UV detection, 20-25 degrees C.) to be 16.12 mg/mL.

EXAMPLE 6

Pravastatin Magnesium Salt

Another preparation of pravastatin was completed. To a 49 mass percent solution of pravastatin sodium salt (1.0057 g; 2.25 mmol) in deionized water was added 2 molar equivalents of propylene glycol (0.171 g). Upon addition of a 53.1 mass percent magnesium chloride (230.0 g; 1.14 mmol) solution in deionized water, crystallization of pravastatin magnesium salt was noted. Overnight, the crystallization was observed to reach completion. The resultant salt was a 2:1 pravastatin to magnesium salt.

Figure 22:
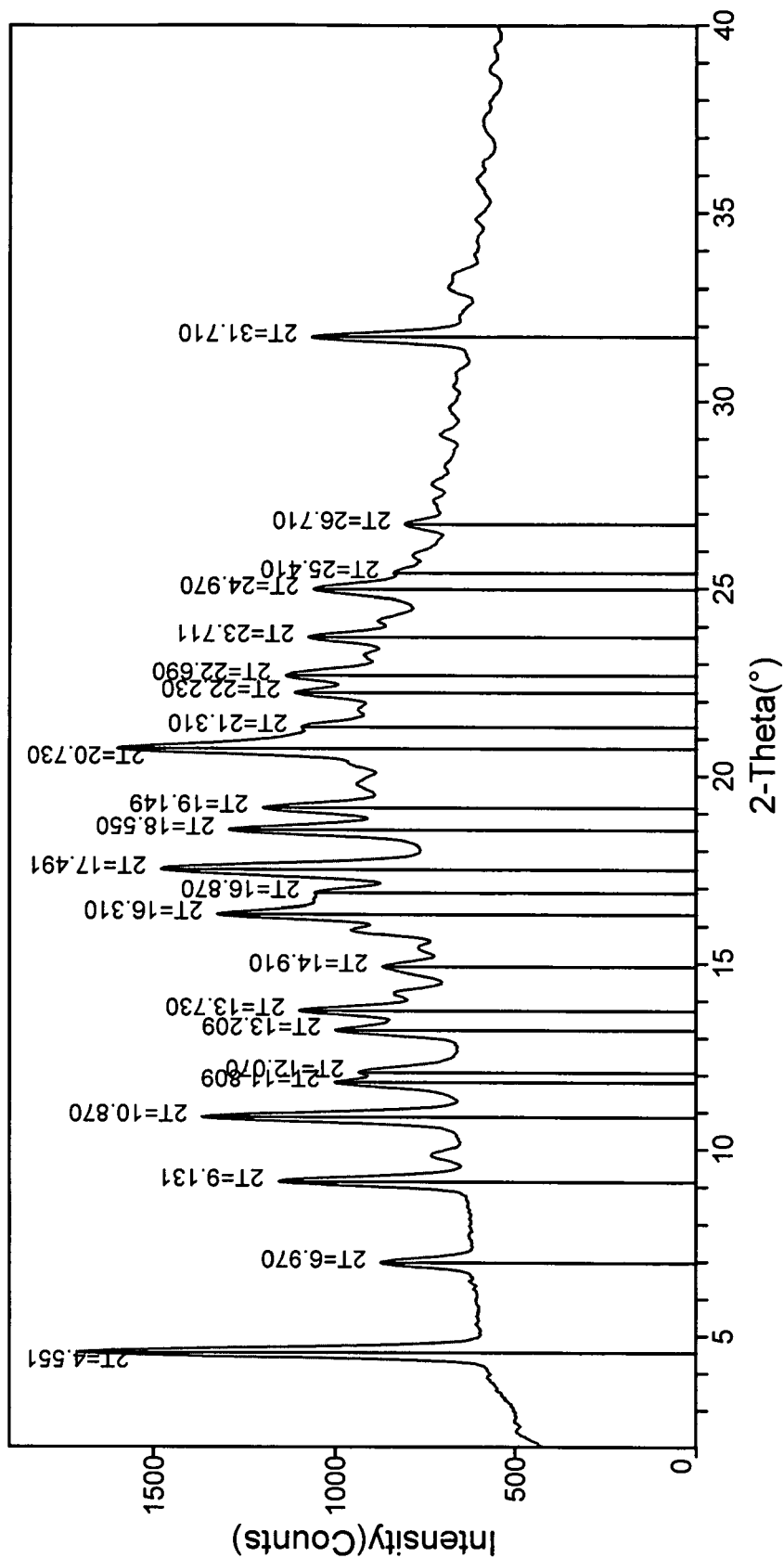
FIG. 22 shows a PXRD diffractogram of a pravastatin magnesium salt.

The pravastatin magnesium salt can be characterized by any one, any two, any three, any four, any five, or any six or more of the PXRD peaks in FIG. 22 including, but not limited to, 4.55, 6.97, 9.13, 10.87, 11.81, 13.21, 13.73, 16.31, 17.49, 18.55, 19.15, 20.73, 22.69, 23.71, and 24.97 degrees 2-theta (Rigaku, data as collected). The peak observed at 31.710 degrees 2-theta corresponds to sodium chloride impurity.

Figure 23:
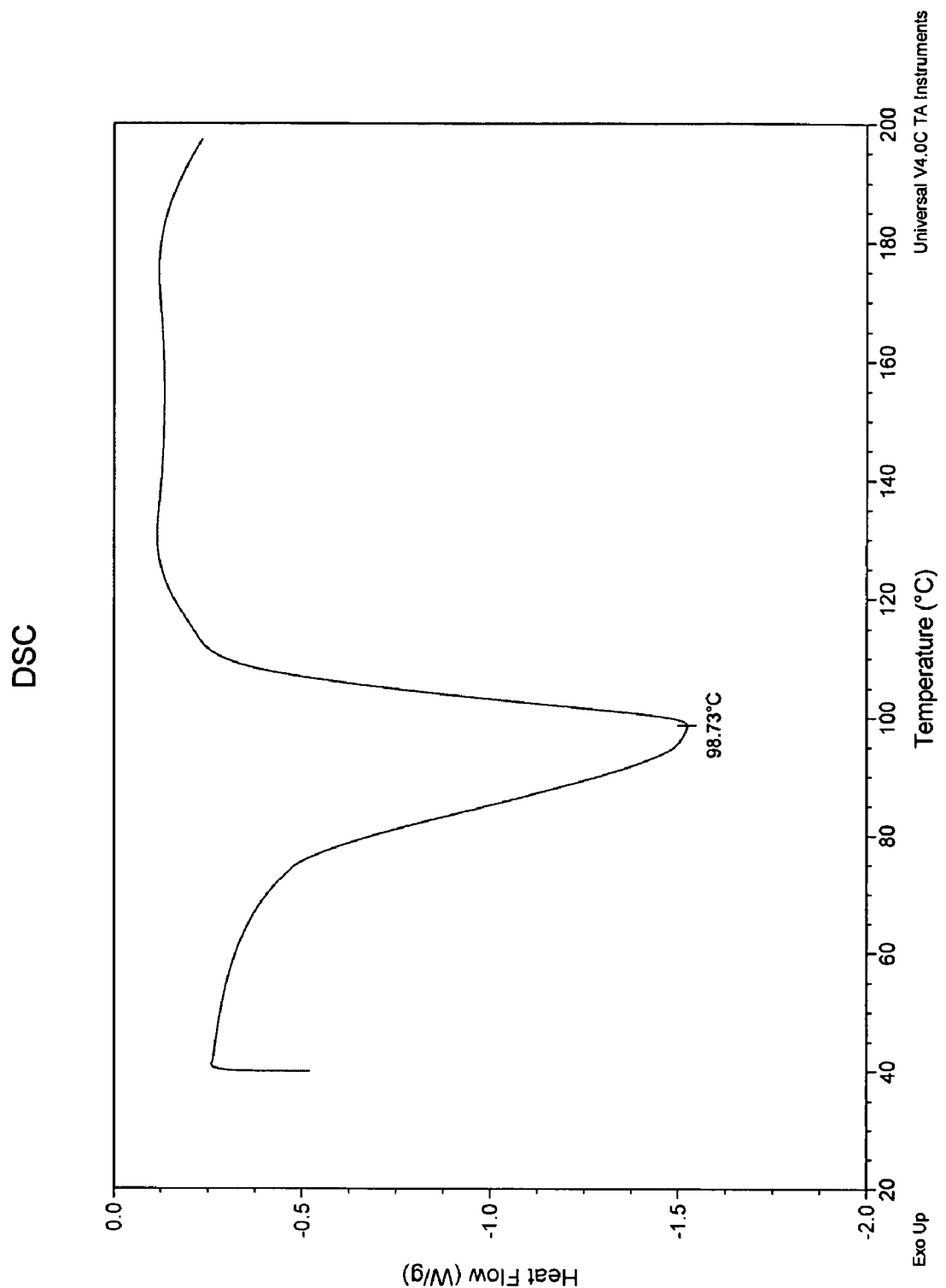
FIG. 23 shows a DSC thermogram of a pravastatin magnesium salt.

DSC was run (on pravastain magnesium salt) from 40 degrees C. to 200 degrees C. at 10 degrees C./minute. DSC showed an endothermic transition at about 99 degrees C. (See FIG. 23).

Figure 24:
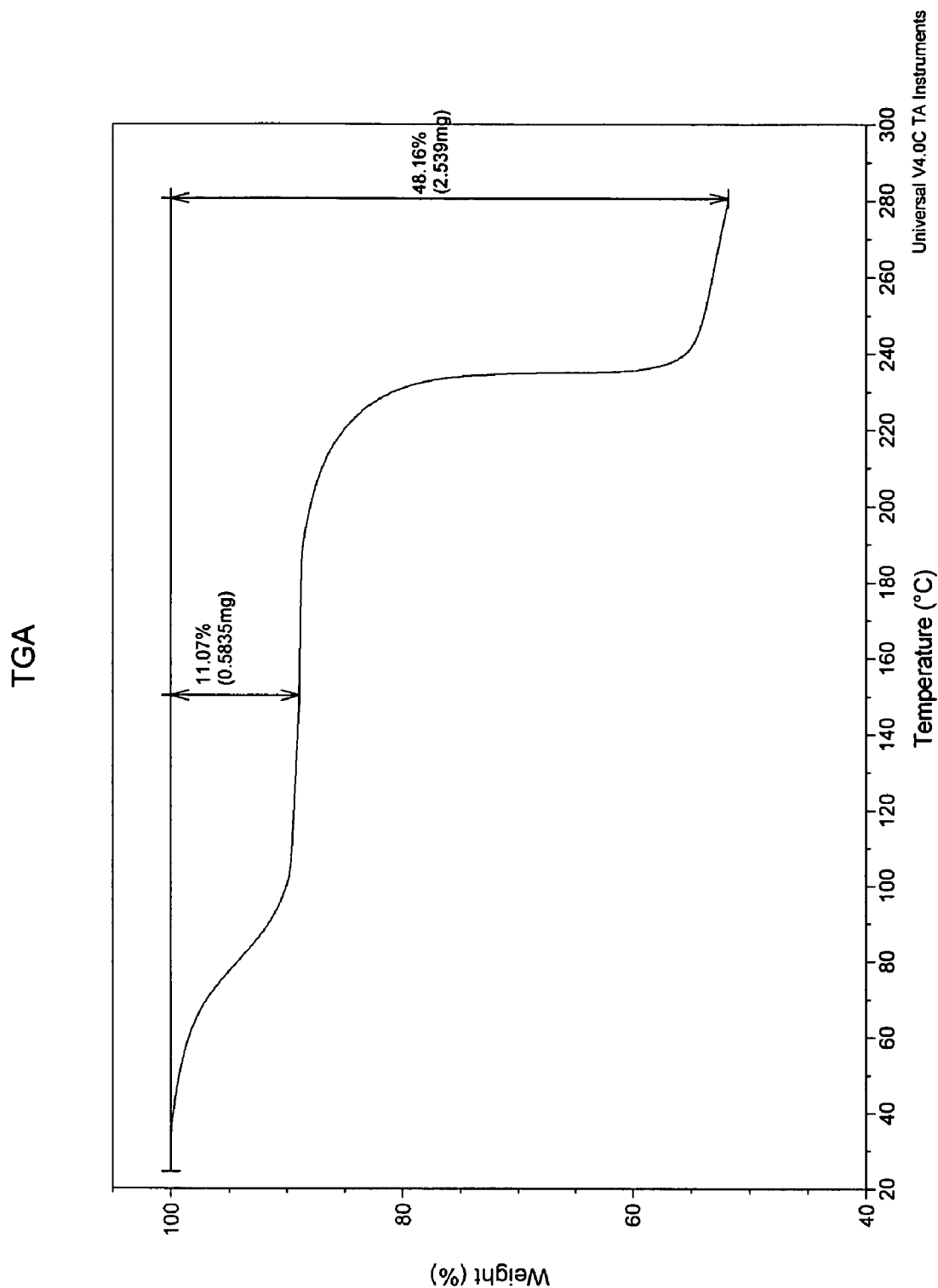
FIG. 24 shows a TGA thermogram of a pravastatin magnesium salt.

TGA was run (on pravastatin magnesium salt) from 25 degrees C. to 280 degrees C. at 10 degrees C./minute. TGA showed about an 11 percent weight loss between 25 degrees C. and about 150 degrees C. (See FIG. 24).

The solubility of pravastatin magnesium salt in water was measured (via UV detection, 20-25 degrees C.) to be 17.24 mg/mL.

EXAMPLE 7

Pravastatin Zinc Salt 2 equivalents of pravastatin sodium dissolved in de-ionized water are reacted with a solution having 1 equivalent of zinc chloride in de-ionized water. Precipitation of crystalline pravastatin zinc occurs immediately at room temperature. The resultant salt was a 2:1 pravastatin to zinc salt.

Figure 25:
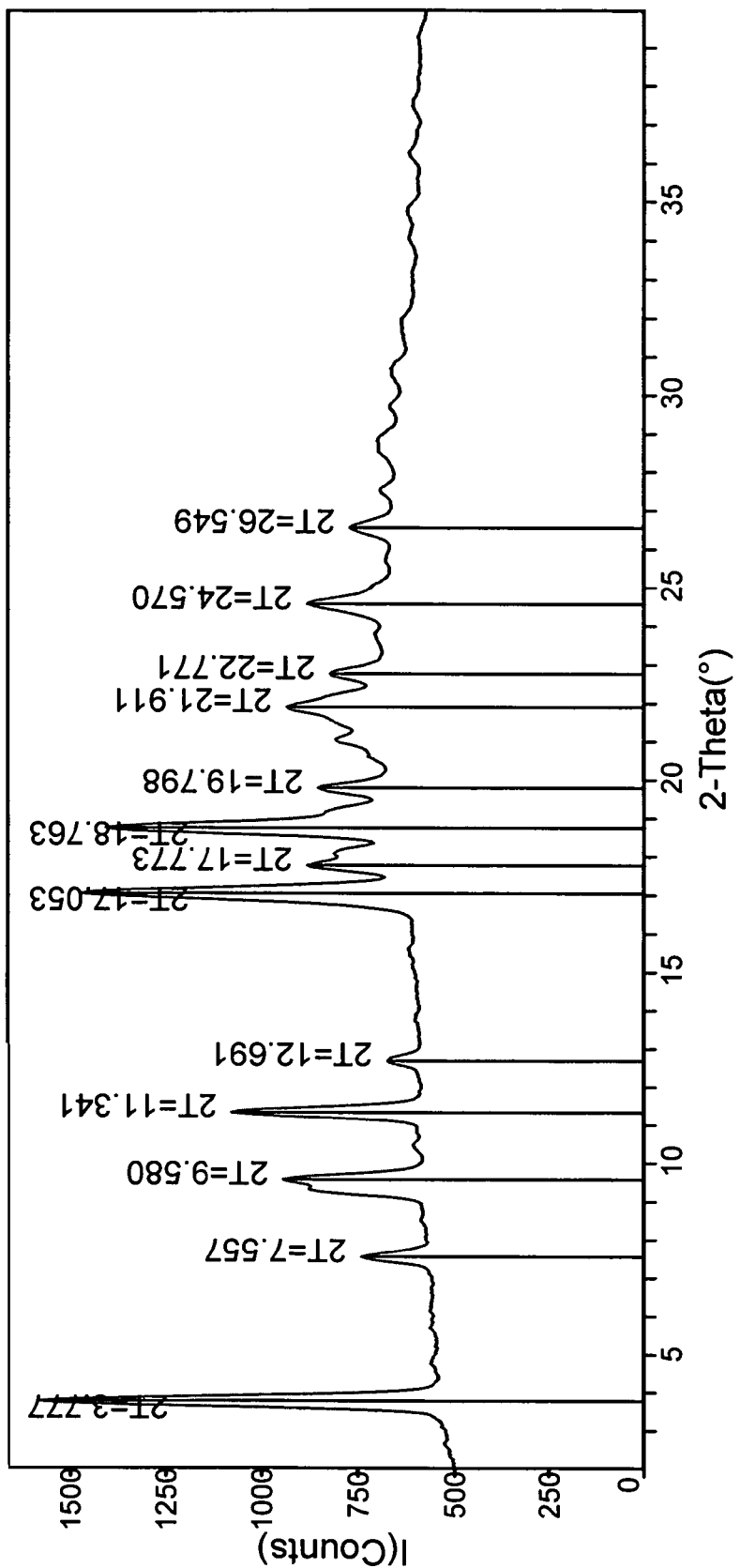
FIG. 25 shows a PXRD diffractogram of a pravastatin zinc salt.

The pravastatin zinc salt can be characterized by any one, any two, any three, any four, any five, or any six or more of the PXRD peaks in FIG. 25 including, but not limited to, 3.78, 7.56, 9.58, 11.34, 17.05, 18.76, 19.80, 21.91, 24.57, and 26.55 degrees 2-theta (Rigaku, data as collected).

Figure 26:
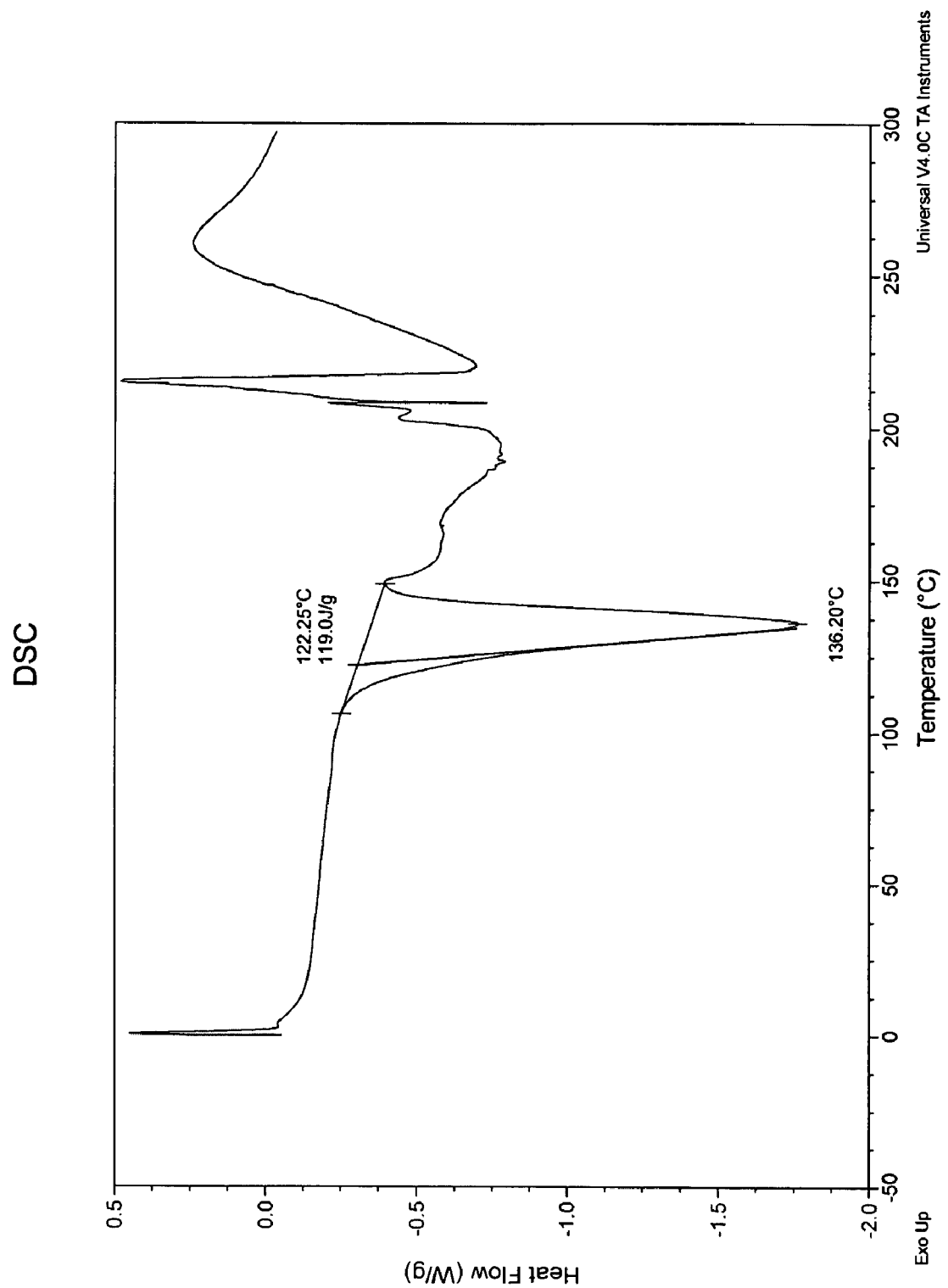
FIG. 26 shows a DSC thermogram of a pravastatin zinc salt.

DSC was run (on pravastain zinc salt) from 25 degrees C. to 300 degrees C. at 10 degrees C./minute. DSC showed an endothermic transition at about 136 degrees C. (See FIG. 26).

Figure 27:
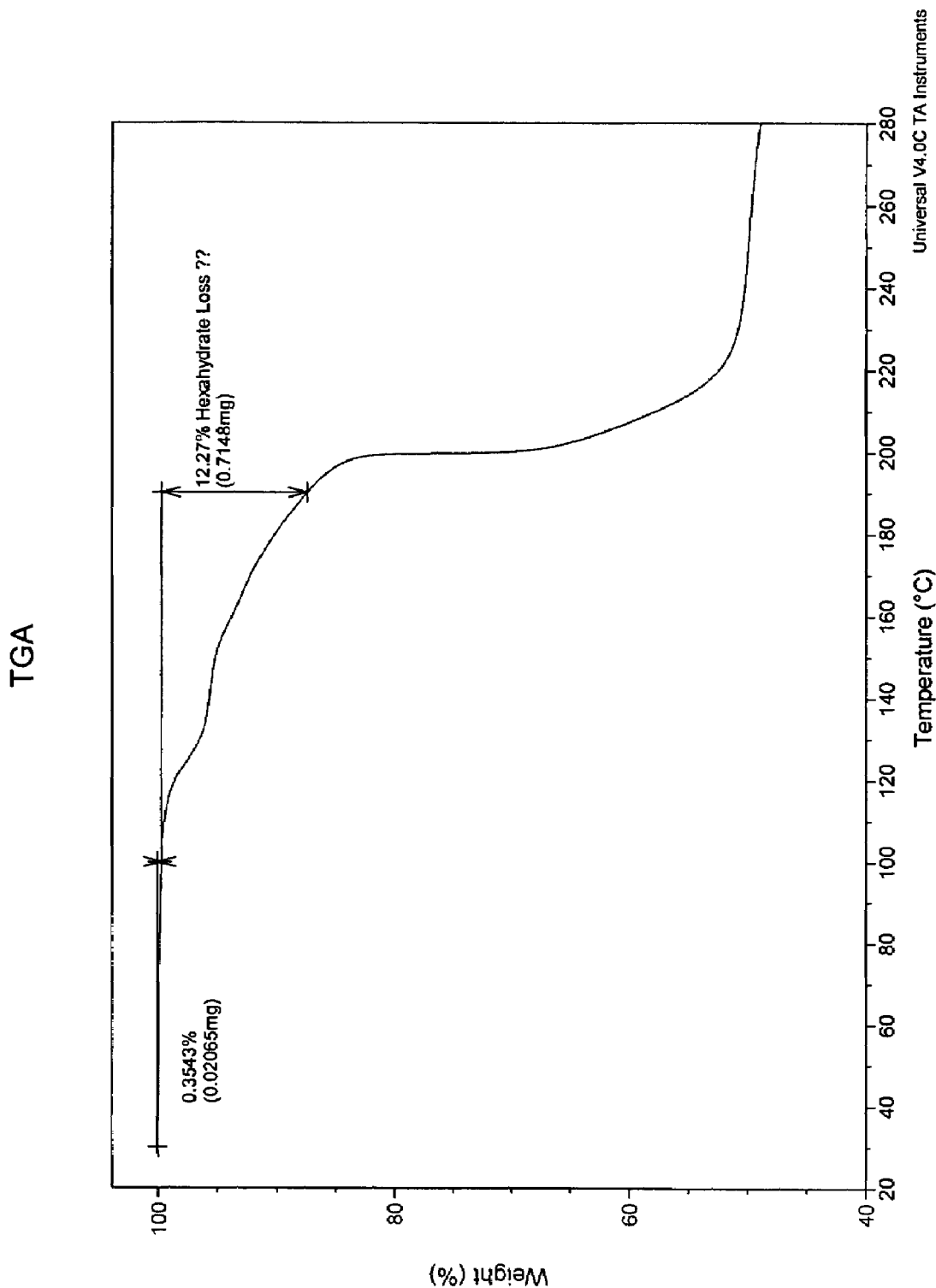
FIG. 27 shows a TGA thermogram of a pravastatin zinc salt.

TGA was run (on pravastatin zinc salt) from 25 degrees C. to 300 degrees C. at 10 degrees C./minute. TGA showed about a 12 percent weight loss between about 100 degrees C. and about 190 degrees C., with negligible weight loss up to about 100 degrees C. (See FIG. 27).

Figure 28:
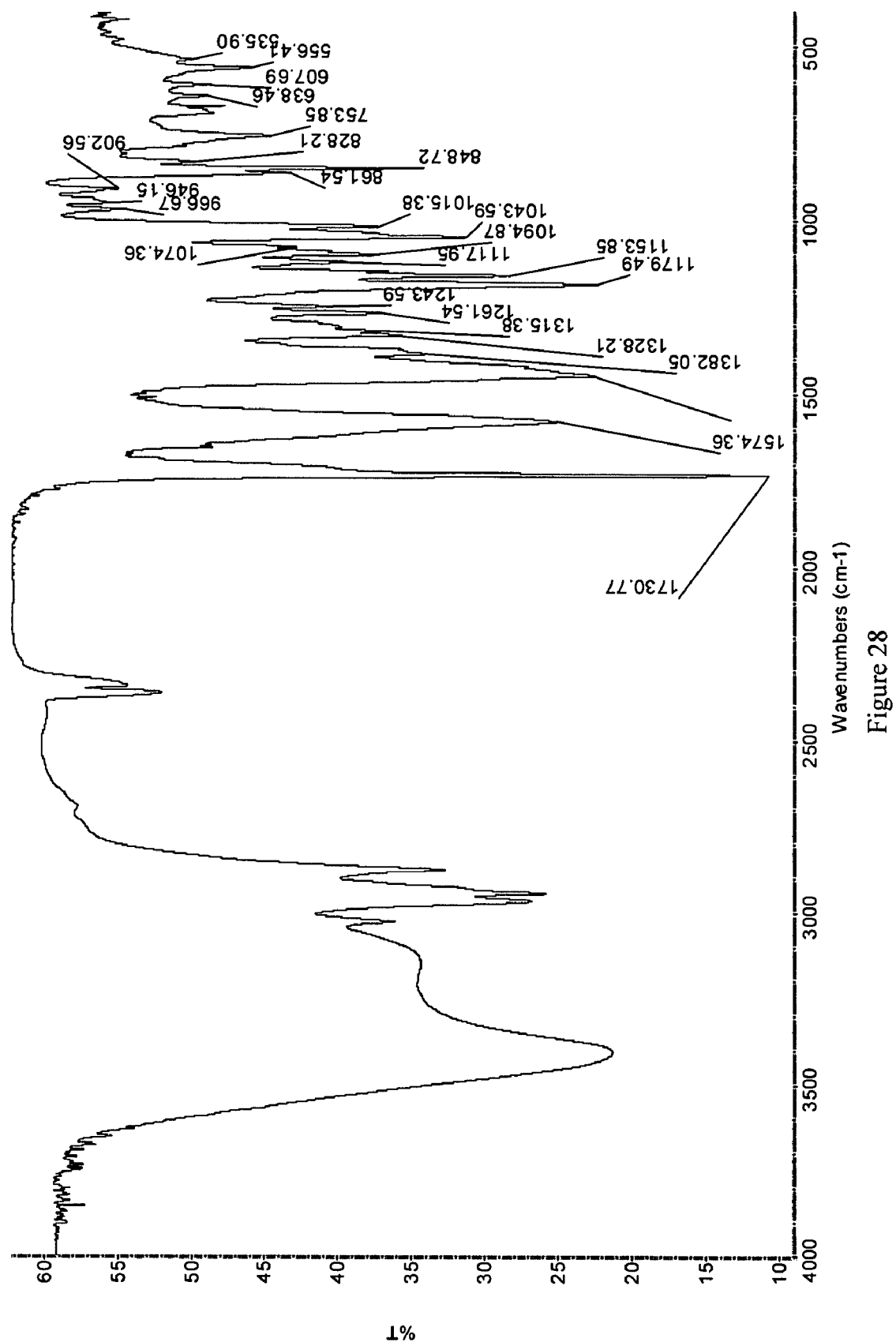
FIG. 28 shows an IR spectrum of a pravastatin zinc salt.

IR spectroscopy was also used to characterize the pravastatin zinc salt. The salt can be characterized by any one, any two, any three, any four, any five, or any six or more of the IR peaks in FIG. 28 including, but not limited to, 1731, 1574, 1179, 1044, 849, and 754 cm$^{-1}$. The IR spectrum was acquired in transmission mode with the sample pressed into a KBr pellet. The spectrum is baseline corrected.

Figure 29:
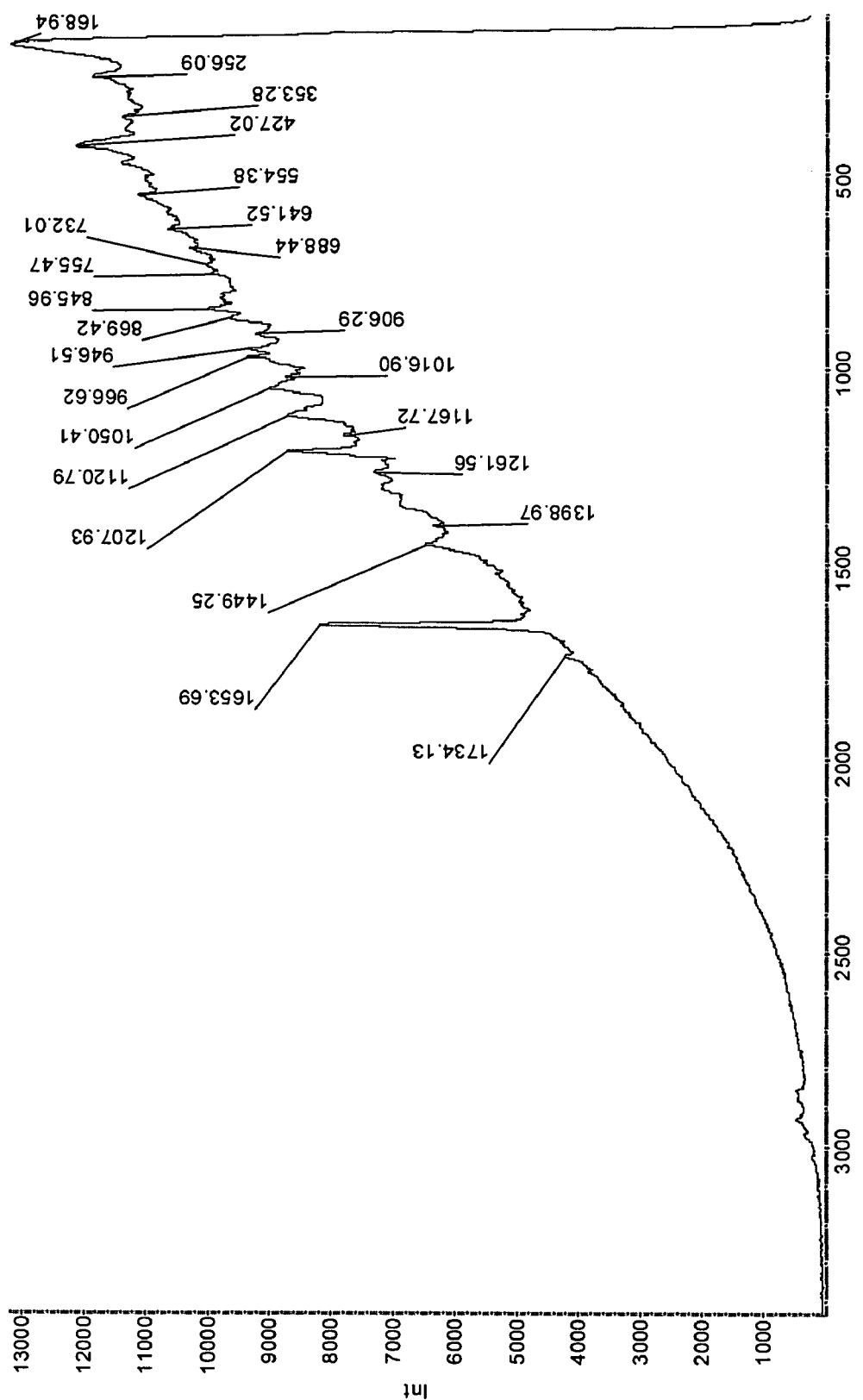
FIG. 29 shows a Raman spectrum of a pravastatin zinc salt.

Raman spectroscopy was also used to characterize the pravastatin zinc salt. The pravastatin zinc salt can be characterized by any one, any two, any three, any four, any five, or any six or more of the Raman shifts in FIG. 29 including, but not limited to, 1654, 1449, 1208, 1121, 1050, 846, and 427 cm$^{-1}$.

Figure 30:
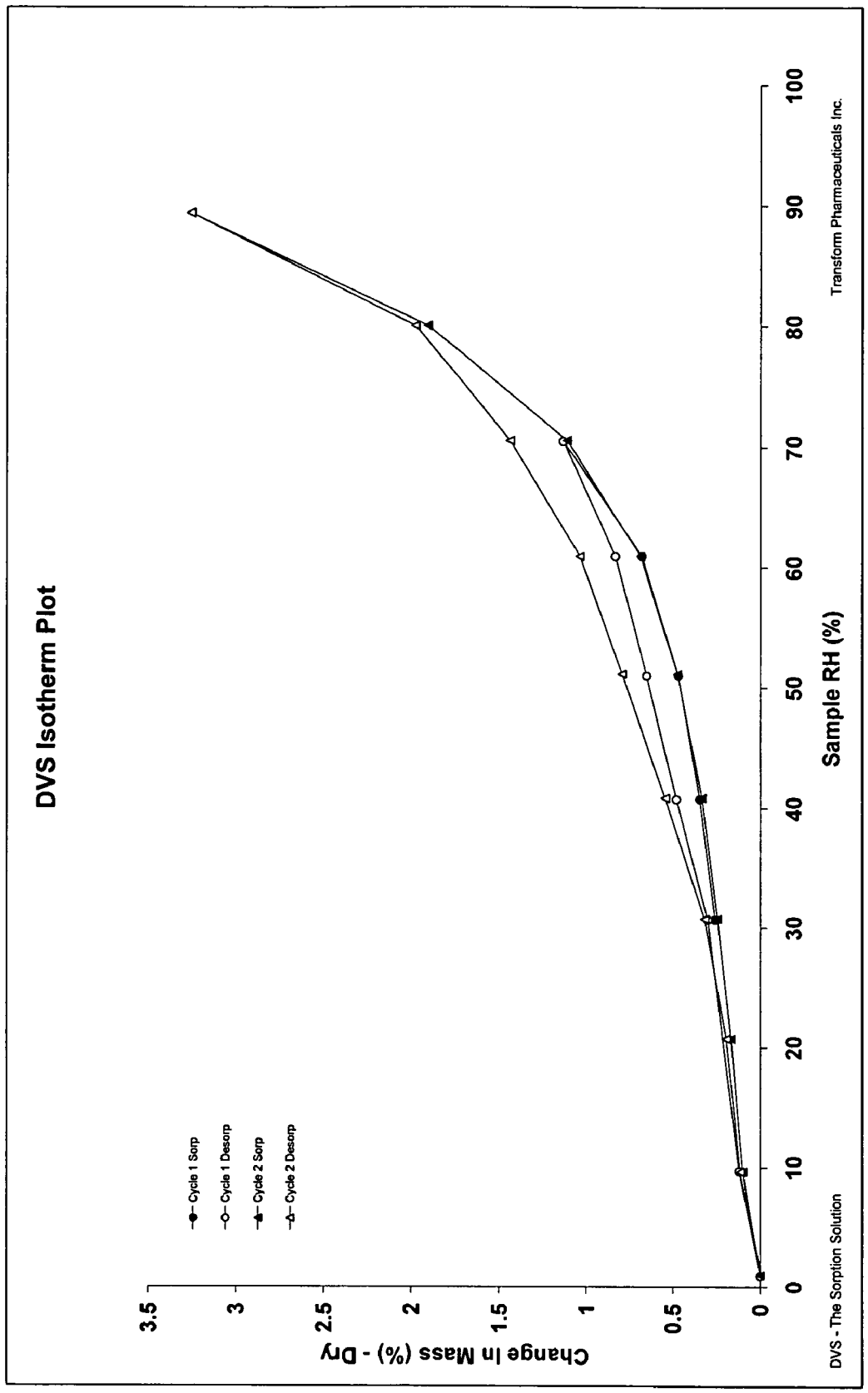
FIG. 30 shows a DVS moisture sorption isotherm plot of a pravastatin zinc salt.

FIG. 30 shows a dynamic vapor sorption (DVS) isotherm plot of the pravastatin zinc salt. This was completed at 25 degrees C. and the data show a gradual increase in moisture sorption.

The solubility of pravastatin zinc salt in water was measured (via UV detection, 20-25 degrees C.) to be 0.53 mg/mL.

EXAMPLE 8

12 Week Stability Data of Pravastatin Salts in E681010:Ethanol Mixture

Several salts of pravastatin were suspended in 87:13 E681010:ethanol mixtures and placed in capped glass vials. Each suspension of pravastatin calcium, pravastatin magnesium, pravastatin sodium, or pravastatin zinc in 87:13 E681010:ethanol was measured periodically for 12 weeks. HPLC was used to measure degradation of the pravastatin salts.

Figure 31:
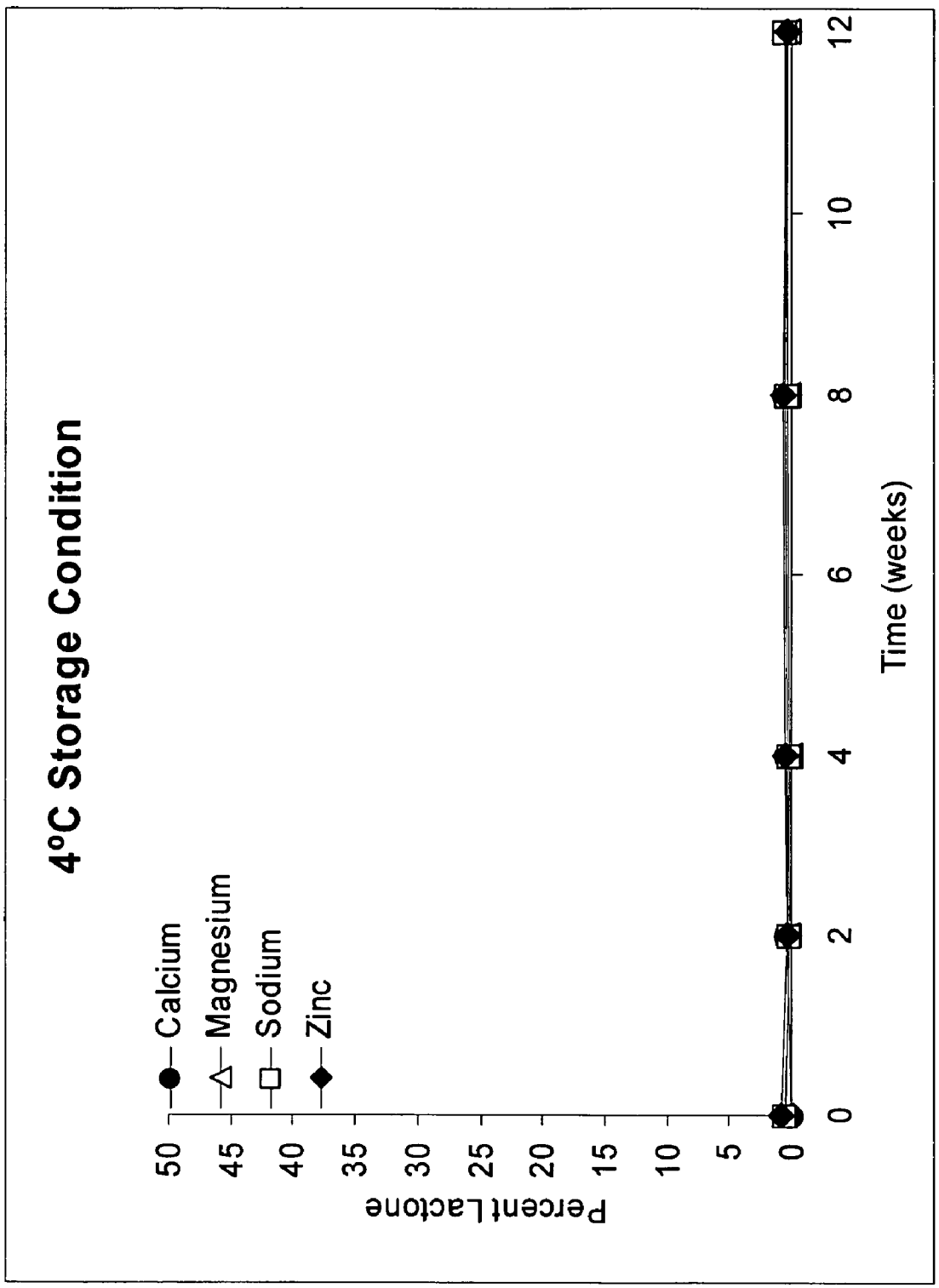
FIG. 31 shows the stability data (percent lactone) of several pravastatin salts at 4 degrees C.

FIG. 31 shows the stability data (percent lactone) at 4 degrees C.

Figure 32:
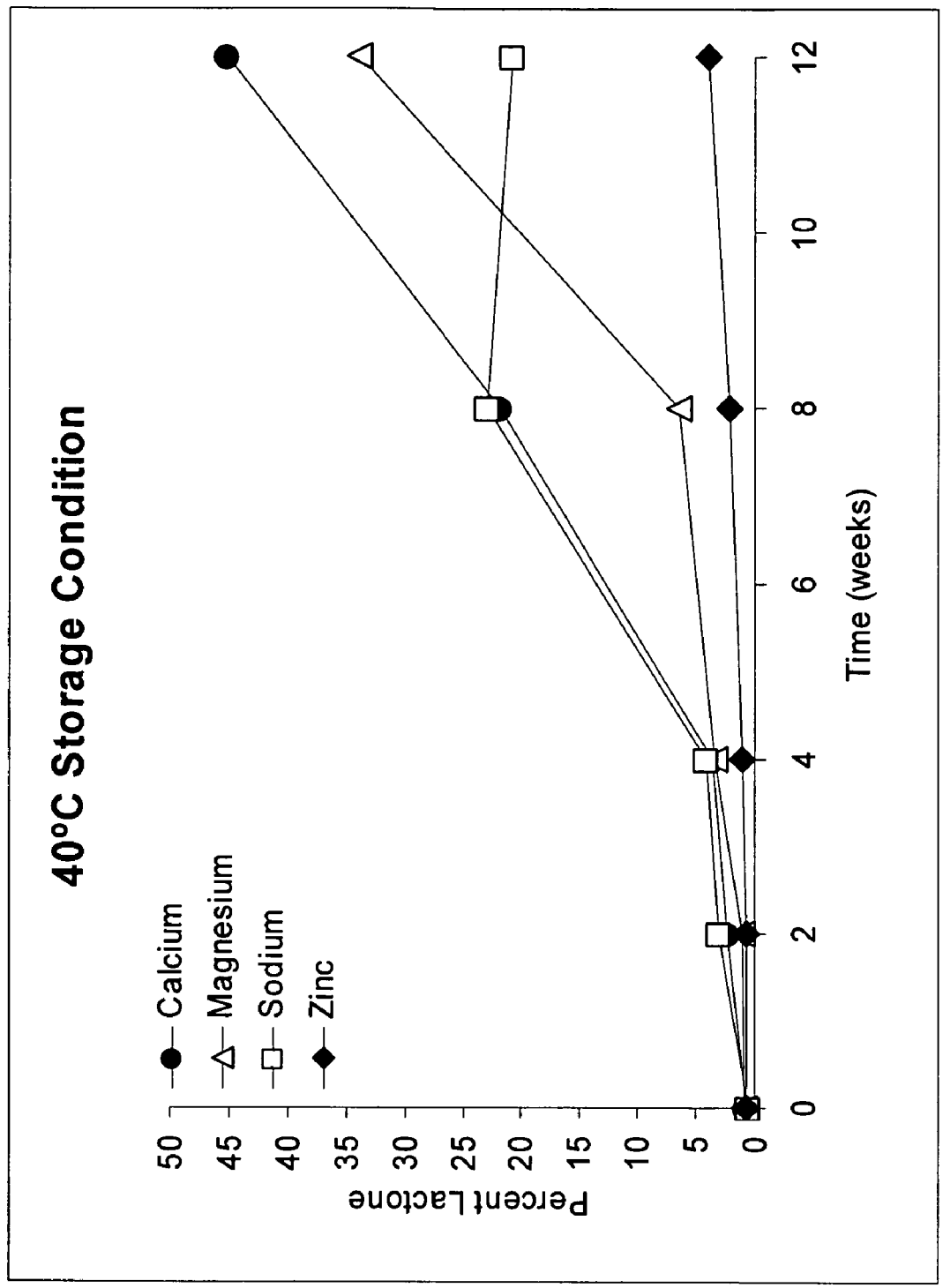
FIG. 32 shows the stability data (percent lactone) of several pravastatin salts at 40 degrees C.

FIG. 32 shows the stability data (percent lactone) at 40 degrees C. The zinc salt exhibits the least degradation to the lactone with about 3 percent after 12 weeks.

Figure 33:
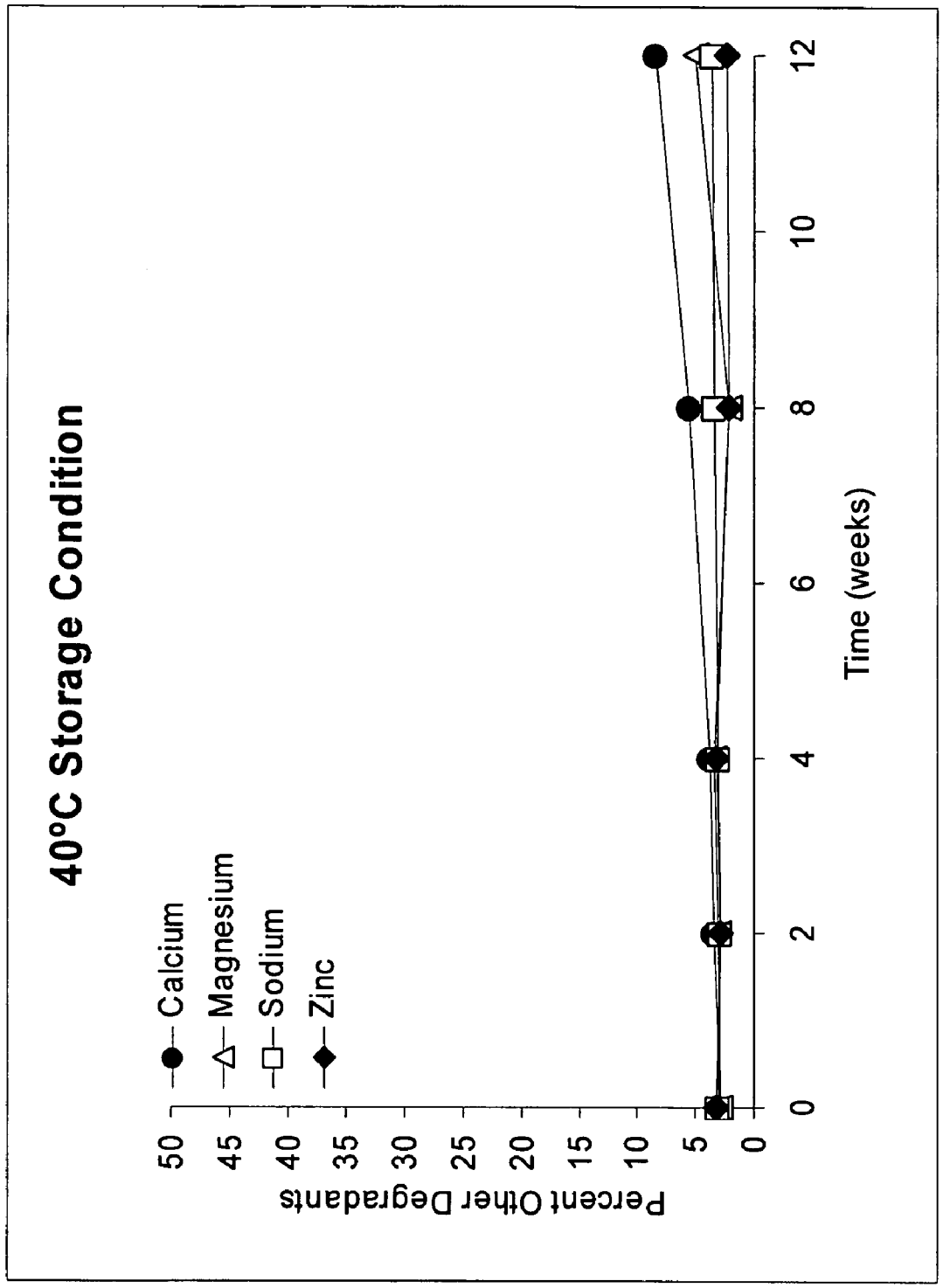
FIG. 33 shows the stability data (percent other degradants) of several pravastatin salts at 40 degrees C.

FIG. 33 shows the stability data (percent other degradants) at 40 degrees C. Again, the zinc salt appears to be the most stable.

What is claimed is:

1. A pharmaceutical composition comprising pravastatin calcium and an omega-3 oil, wherein the omega-3 oil comprises 46% (w/w) ethyl ester of eicosapentaenoic acid, 38% (w/w) ethyl ester of docosahexaenoic acid, and 8% (w/w) ethyl ester of other omega-3 oils, and wherein said composition exhibits a loss of potency of less than or equal to 3.0 percent after 26 weeks at 25 degrees C.

2. A method of reducing or treating elevated cholesterol levels, atherosclerosis, hyperlipidemia, cardiovascular disease, and coronary artery disease and/or cerebrovascular disease comprising administering the pharmaceutical composition of claim 1 to a mammal in need thereof.

3. The pharmaceutical composition of claim 1, wherein the pravastatin calcium is crystalline.

4. The pharmaceutical composition of claim 1, wherein the pravastatin calcium exhibits a powder X-ray diffraction pattern as shown in FIG. 1.

Figure 3:
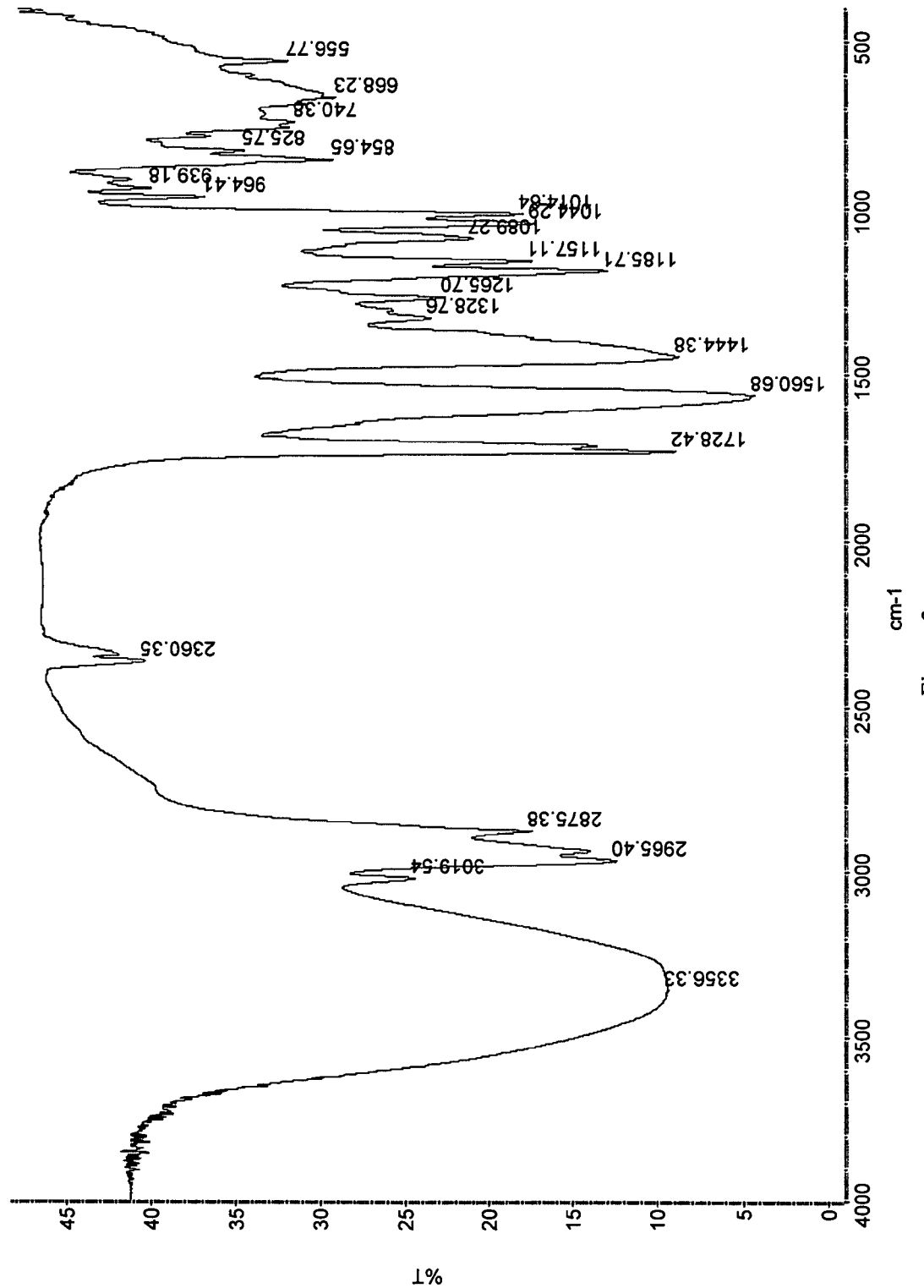
FIG. 3 shows an IR spectrum of a pravastatin calcium salt.

5. The pharmaceutical composition of claim 1, wherein the pravastatin calcium exhibits an IR spectrum as shown in FIG. 3.

* * * * *

UNITED STATES PATENT AND TRADEMARK OFFICE
CERTIFICATE OF CORRECTION

PATENT NO. : 7,642,287 B2  Page 1 of 1
APPLICATION NO. : 11/197880
DATED : January 5, 2010
INVENTOR(S) : Guzman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 333 days.

Signed and Sealed this

Sixteenth Day of November, 2010

David J. Kappos
*Director of the United States Patent and Trademark Office*